US009809856B2

(12) United States Patent
Harbour

(10) Patent No.: US 9,809,856 B2
(45) Date of Patent: Nov. 7, 2017

(54) METHOD FOR PREDICTING RISK OF METASTASIS

(71) Applicant: The Washington University, St. Louis, MO (US)

(72) Inventor: J. William Harbour, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 79 days.

(21) Appl. No.: 14/104,686

(22) Filed: Dec. 12, 2013

(65) Prior Publication Data
US 2014/0141441 A1 May 22, 2014

Related U.S. Application Data

(62) Division of application No. 12/989,272, filed as application No. PCT/US2009/041436 on Apr. 22, 2009, now Pat. No. 8,642,279.

(60) Provisional application No. 61/046,879, filed on Apr. 22, 2008.

(51) Int. Cl.
*C12Q 1/68* (2006.01)
(52) U.S. Cl.
CPC ..... *C12Q 1/6886* (2013.01); *C12Q 2600/158* (2013.01)
(58) Field of Classification Search
None
See application file for complete search history.

(56) References Cited

U.S. PATENT DOCUMENTS

| | | |
|---|---|---|
| 6,194,557 B1 | 2/2001 | Li et al. |
| 6,307,035 B1 | 10/2001 | Rauscher et al. |
| 6,566,495 B1 | 5/2003 | Fodor et al. |
| 8,642,279 B2 | 2/2014 | Harbour et al. |
| 9,133,523 B2 | 9/2015 | Bowcock et al. |
| 9,441,277 B2 | 9/2016 | Bowcock et al. |
| 2006/0275844 A1 | 12/2006 | Linke et al. |
| 2007/0105133 A1 | 5/2007 | Clarke et al. |
| 2007/0207479 A1 | 9/2007 | Wong et al. |
| 2009/0275633 A1 | 11/2009 | Esteller |
| 2011/0124525 A1 | 5/2011 | Harbour |
| 2012/0077682 A1 | 3/2012 | Bowcock et al. |
| 2016/0053330 A1 | 2/2016 | Bowcock et al. |
| 2016/0362750 A1 | 12/2016 | Bowcock et al. |

FOREIGN PATENT DOCUMENTS

| | | |
|---|---|---|
| GB | 2484003 | 3/2012 |
| WO | 2009132126 A2 | 10/2009 |
| WO | 2012040614 A1 | 3/2012 |

OTHER PUBLICATIONS

Onken, M. et al., "Oncogenic mutations in GNAQ occur early in uveal melanoma," Invest. Ophthalmol. Vis. Sci., Dec. 2008, pp. 5230-5234, vol. 49, No. 12 (with Author Manuscript, 12 pages).
Onken, M. et al., "An Accurate, Clinically Feasible Multi-Gene Expression Assay for Predicting Metastasis in Uveal Melanoma," J. Mol. Diagnostics, Jul. 2010, pp. 461-468, vol. 12, No. 4.
Onken, M. et al., "Gene Expression Profiling in Uveal Melanoma Reveals Two Molecular Classes and Predicts Metastatic Death," Cancer Res., Oct. 15, 2004, pp. 7205-7209, vol. 64.
Onken, M. et al., "Prognostic Testing in Uveal Melanoma by Transcriptomic Profiling of Fine Needle Biopsy Specimens," J. Mol. Diagnostics, Nov. 2006, pp. 567-573, vol. 8, No. 5.
Onken, M. et al., "Association Between Microarray Gene Expression Signature and Extravascular Matrix Patterns in Primary Uveal Melanomas," Am. J. Ophthalmol., Oct. 2005, pp. 748-749, vol. 140, No. 4.
Onken, M. et al., "Loss of Heterozygosity of Chromosome 3 Detected with Single Nucleotide Polymorphisms Is Superior to Monosomy 3 for Predicting Metastasis in Uveal Melanoma," Clin. Cancer Res., May 15, 2007, pp. 2923-2927, vol. 13, No. 10.
Patel, K. et al., "Prediction of prognosis in patients with uveal melanoma using fluorescence in situ hybridization," Br. Ophthalmol., 2001, pp. 1440-1444, vol. 85.
Peng, H. et al., "Feature Selection Based on Mutual Information: Criteria of Max-Dependency, Max-Relevance, and Min-Redundancy," IEEE Trans. Pattern. Anal. Mach. Intell., Aug. 2005, pp. 1226-1238, vol. 27, No. 8.
Perry, A. et al., "NF1 Deletions in S-100 Protein-Positive and Negative Cells of Sporadic and Neurofibromatosis 1 (NF1)-Associated Plexiform Neurofibromas and Malignant Peripheral Nerve Sheath Tumors," Am. J. Pathol., Jul. 2001, pp. 57-61, vol. 159, No. 1.
Petrausch, U. et al., "Significance of gene expression analysis in uveal melanoma in comparison to standard risk factors for risk assessment of subsequent metastases," Eye, 2007, pp. 1-11.
Pinkel, D. et al., "High resolution analysis of DNA copy number variation using comparative genomic hybridization to microarrays," Nat. Genet., Oct. 1998, pp. 207-211, vol. 20.
Prescher, G. et al., "Nonrandom Chromosomal Abnormalities in Primary Uveal Melanoma," J. Natl. Cancer Inst., 1990, pp. 1765-1769, vol. 82, No. 22.
Prescher, G. et al., "Prognostic implications of monosomy 3 in uveal melanoma," Lancet, May 4, 1996, pp. 1222-1225, vol. 347 (abstract only).
Pusztai L. et al., "Clinical trial design for microarray predictive marker discovery and assessment," Ann. Oncol., 2004, pp. 1731-1737, vol. 15.
Rockett, J. et al., "DNA arrays: technology, options and toxicological applications," Xenobiotica, 2000, pp. 155-177, vol. 30, No. 2.
Russell, N. et al., "Deubiquitinating enzyme purification, assay inhibitors, and characterization," Methods Mol. Biol., 2005, pp. 207-219, vol. 301 (abstract only).
Sandinha, M. et al., "Monosomy 3 Predicts Death but Not Time Until Death in Choroidal Melanoma," Invest. Ophthalmol. Vis. Sci., Oct. 2005, pp. 3497-3501, vol. 46, No. 10.

(Continued)

*Primary Examiner* — Celine Qian
(74) *Attorney, Agent, or Firm* — Polsinelli PC

(57) ABSTRACT

The invention encompasses methods and compositions for predicting the risk of metastasis. In particular, the invention encompasses a method for correlating the level of expression of one or more nucleic acid sequences with a risk of metastasis.

7 Claims, 18 Drawing Sheets
(14 of 18 Drawing Sheet(s) Filed in Color)

(56) References Cited

OTHER PUBLICATIONS

Scharer, C., "Identification of the Transformational Properties and Transcriptional Targets of the Oncogenic SRY Transcription Factor SOX4," Emory University, Award No. W81XWH-07-1-0044, Annual Summary, prepared for U.S. Army Medical Research and Material Command, Jan. 10, 2008; 14 pages.

Scheuermann, J. et al., "Histone H2A deubiquitinase activity of the Polycomb repressive complex PR-DUB," Nature, May 13, 2010, pp. 243-247, vol. 465, No. 7295.

Schouten, J. et al., "Relative quantification of 40 nucleic acid sequences by multiplex ligation-dependent probe amplification," Nucl. Acid Res., 2002, pp. 1-13, vol. 30, No. 12, e57.

Search Report and Written Opinion dated Feb. 9, 2012 for related Dutch Patent Application No. 2007467; 10 pages.

Sima, C. et al., "Superior feature-set ranking for small samples using bolstered error estimation," Bioinformatics, 2005, pp. 1046-1054, vol. 21, No. 7.

Sisley, K. et al., "Cytogenetic Findings in Six Posterior Uveal Melanomas: Involvement of Chromosomes 3, 6, and 8," Genes, Chromosomes & Cancer, Sep. 1990, pp. 205-209, vol. 2, No. 3.

Taylor, J. et al., "Individualized Predictions of Disease Progression Following Radiation Therapy for Prostate Cancer," J. Clin. Oncol., Feb. 1, 2005, pp. 816-825, vol. 23, No. 4.

Tschentscher, F. et al., "Tumor Classification Based on Gene Expression Profiling Shows That Uveal Melanomas with and without Monosomy 3 Represent Two Distinct Entities," Cancer Res., May 15, 2003, vol. 63, p. 2578-2584.

Tse, W. et al., "Genome-wide loss-of-function analysis of deubiquitylating enzymes for zebrafish development," BMC Genomics, Dec. 30, 2009, vol. 10, No. 637.

Tyagi, S. et al., "E2F activation of S phase promoters via association with HCF-1 and the MLL family of histone H3K4 methyltransferases," Mol. Cell, Jul. 6, 2007, pp. 107-119, vol. 27, No. 1 (abstract only).

Van Gils, W., Thesis entitled "Molecular Prognostic Markers in Unveal Melanoma: Expression Profiling and Genomic Studies," PrintPartners IpsKamp, Enschede, 2007, Erasmus MC, Rotterdam, Chapters 1-10, pp. 1-144 (128 total pages).

Van Raamsdonk, C. et al., "Frequent somatic mutations of GNAQ in uveal melanoma and blue nevi," Nature, Jan. 29, 2009, pp. 599-602, vol. 457, No. 7229.

Ventii, K. et al., "BAP1 is a tumor suppressor that requires deubiquitinating activity and nuclear localization," Cancer Res., Sep. 1, 2008, pp. 6953-6962, vol. 68, No. 17.

Wackerly, D. et al., "Mathematical Statistics with Applications," Belmont, CA, Duxbury Press, 1996, p. 107 [BOOK].

Wang, Y. et al., "MMDB: annotating protein sequences with Entrez's 3D-structure database," Nucleic Acids Res., Jan. 2007, pp. D298-D300, vol. 35, Database issue.

Watanabe, T. et al., "Gene Expression Signature and the Prediction of Lymph Node Metastasis in Colorectal Cancer by DNA Microarray," Dis. Colon Rectum, 2009, pp. 1941-1948, vol. 52, No. 12.

White, V. et al., "Acquired Homozygosity (Isodisomy) of Chromosome During Clonal Evolution of Uveal Melanoma: Association with Morphologic Heterogeneity," Genes, Chromosomes & Cancer, Feb. 1996, pp. 138-143, vol. 15, No. 2.

Wood, L. et al., "The Genomic Landscapes of Human Breast and Colorectal Cancers," Science, Nov. 16, 2007, pp. 1108-1113, vol. 318.

Worley, L. et al., "Transcriptomic versus Chromosomal Prognostic Markers and Clinical Outcome in Uveal Melanoma," Clin. Cancer Res., Mar. 1, 2007, pp. 1466-1471, vol. 13, No. 5.

Ye, H. et al., "Genomic assessments of the frequent loss of heterozygosity region on 8p21.3~p22 in head and neck squamous cell carcinoma," Cancer Genetics and Cytogenetics, 2007, pp. 100-106, vol. 176.

Zhang, D. et al., "Ramification Amplification: A novel Isothermal DNA Amplification Method," Mol. Diagnosis, Jun. 2001, pp. 141-150, vol. 6, No. 2.

Office Action from related U.S. Appl. No. 13/243,572, dated Sep. 24, 2014; 6 pgs.

Aalto, Y. et al., "Concomitant Loss of Chromosome 3 and Whole Arm Losses and Gains of Chromosome 1, 6, or 8 in Metastasizing Primary Uveal Melanoma," Investigative Ophthalmology & Visual Science, Feb. 2001, pp. 313-317, vol. 42, No. 2.

Altschul, S. et al., "Basic Local Alignment Search Tool," J. Mol. Biol., Oct. 5, 1990, pp. 403-410, vol. 215, No. 3.

Office Action dated Mar. 25, 2013 for related U.S. Appl. No. 12/989,272; 8 pages.

Office Action dated Jul. 21, 2014 for related European Patent Application No. 09735059.9; 8 pages.

Office Action dated Mar. 7, 2014 for related U.S. Appl. No. 13/243,572; 7 pages.

Onken, M. et al., "Functional Gene Expression Analysis Uncovers Phenotypic Switch in Aggressive Uveal Melanomas," Cancer Res., May 1, 2006, pp. 4602-4609, vol. 66, No. 9.

Office Action from related U.S. Appl. No. 13/243,572, dated Jan. 16, 2015; 5 pgs.

Notice of Allowance from related U.S. Appl. No. 13/243,572, dated Apr. 29, 2015; 5 pgs.

Notice of Allowance dated Mar. 22, 2016 from related U.S. Appl. No. 14/811,560; 5 pgs.

Office Action dated Nov. 24, 2015 from related U.S. Appl. No. 14/811,560; 6 pgs.

Office Action dated Oct. 3, 2016 from related U.S. Appl. No. 15/188,640; 7 pgs.

Altschul, S. et al., "Gapped BLAST and PSI-BLAST: a new generation of protein database search programs," Nucleic Acids Res., 1997, pp. 3389-3402, vol. 25, No. 17.

Bashiardes, S. et al., "Direct genomic selection," Nat. Methods, Jan. 2005, pp. 63-69, vol. 2, No. 1.

Bauer, J. et al., "Oncogenic GNAQ mutations are not correlated with disease-free survival in uveal melanoma," Br. J. Cancer, 2009, pp. 813-815, vol. 101.

Chang, S. et al., "Prognostic biomarkers in uveal melanoma: evidence for a stem cell-like phenotype associated with metastasis," Melanoma Res., Jun. 2008, pp. 191-200, vol. 18, No. 3 (abstract only).

Char, D. et al., "Cytomorphometry of Uveal Melanoma. Comparison of Fine Needle Aspiration Biopsy Samples with Histologic Sections," Anal. Quant. Cytol. Histol., 1991, pp. 293-299, vol. 13, No. 4.

Combined Search and Examination Report dated Oct. 4, 2011 for related British Patent Application No. 1116471.2; 6 pages.

Coupier, I. et al., "BAP1 and breast cancer risk," Familial Cancer, 2005, pp. 273-277, vol. 4.

Cross, N. et al., "Multiple locations on chromosome 3 are the targets of specific deletions in uveal melanoma," Eye, Apr. 2006, pp. 476-481, vol. 20, No. 4.

Demidov et al., Eds., DNA Amplification: Current technologies and applications, 2004. Pub. Horizon Bioscience, ISBN:0-9545232-9-6 [BOOK].

Edge, S. et al., Eds., "The AJCC Cancer Staging Manual," 7th edition, 2009, Springer, New York, pp. 547-559 [BOOK].

Efferth, T. et al., "Pharmacogenetics for individualized cancer chemotherapy," Pharmacol. Ther., 2005, pp. 155-176, vol. 107, No. 2.

European Search Report dated Jul. 22, 2011 for related European Patent Application No. 09735059.9; 10 pages.

Fang, Y. et al., "The potential role of ubiquitin c-terminal hydrolases in oncogenesis," Biochim. Biophys. Acta, Aug. 2010, ePub Mar. 17, 2010, pp. 1-6, vol. 1806, No. 1.

Faulkner-Jones, B. et al., "Fine Needle Aspiration Biopsy with Adjunct Immunohistochemistry in Intraocular Tumor Management," Acta Cytol., May-Jun. 2005, pp. 297-308, vol. 49, No. 3.

Finger, P., "The 7th Edition AJCC Staging System for Eye Cancer," Arch. Pathol. Lab. Med., Aug. 2009, pp. 1197-1198, vol. 133, No. 8.

Garraway, L. et al., "Integrative genomic analyses identify MITF as a lineage survival oncogene amplified malignant melanoma," Nature, Jul. 7, 2005, pp. 117-122, vol. 436.

(56) References Cited

OTHER PUBLICATIONS

Gaytan De Ayala Alonso, A. et al., "A Genetic Screen Identifies Novel Polycomb Group Genes in *Drosophilia*," Genetics, Aug. 2007, pp. 2099-2108, vol. 176.

Golub, T. et al., "Molecular Classification of Cancer: Class Discovery and Class Prediction by Gene Expression Monitoring," Science, Oct. 15, 1999, pp. 531-537, vol. 286.

Gordon, K. et al., "Comparative Genomic Hybridization in the Detection of DNA Copy Number Abnormalities in Uveal Melanoma," Cancer Res., Sep. 1, 1994, pp. 4764-4768, vol. 54.

Guenard, F. et al., "Genetic sequence variations of BRCA1-interacting genes AURKA, BAP1, BARD1, and DHX9 in French Canadian Families with high risk of breast cancer," J. Human Genet., 2009, pp. 152-161, vol. 54.

Harbour, J. et al., "Frequent Mutation of BAP1 in Metastasizing Uveal Melanomas," Science, Dec. 3, 2010, pp. 1410-1413, vol. 330, No. 6009.

Harbour, J., "Clinical overview of uveal melanoma: introduction to tumors of the eye," In: Ocular Oncology, Albert DM, Polans A, eds., Marcel Dekker, New York, 2003, pp. 1-18.

Hemesath, T. et al., "MAP kinase links the transcription factor Microphthalmia to c-Kit signalling in melanocytes," Nature, Jan. 15, 1998, pp. 298-301, vol. 391 (abstract only).

Horsman, D. et al., "Monosomy 3 and Isochromosome 8q in a Uveal Melanoma," Cancer Genet. Cytogenet., 1990, pp. 249-253, vol. 45, No. 2.

International Search Report and Written Opinion dated Aug. 13, 2009 for related International Patent Application No. PCT/US2009/041436; 9 pages.

International Search Report and Written Opinion date Jan. 20, 2012 for related International Patent Application No. PCT/US2011/053058; 8 pages.

Jensen, D. et al., "BAP1: a novel ubiquitin hydrolase which binds to the BRCA1 RING finger and enhances BRCA1—mediated cell growth suppression," Oncogene, Mar. 5, 1998, pp. 1097-1112, vol. 16, No. 9.

Karlin, S. et al., "Methods for assessing the statistical significance of molecular sequence features by using general scoring schemes," Proc. Natl. Acad. Sci. USA, Mar. 1990, pp. 2264-2268, vol. 87, No. 6.

Kilic, E. et al., "Clinical and Cytogenetic Analyses in Uveal Melanoma," Invest. Ophthalmol. Vis. Sci., Sep. 2006, pp. 3703-3707, vol. 47, No. 9.

Landreville S. et al., "Emerging insights into the molecular pathogenesis of uveal melanoma," Future Oncol., Oct. 2008, p. 629-636, vol. 4, No. 5 (abstract only).

Lang, D. et al., "Pax3 functions at a nodal point in melanocyte stem cell differentiation," Nature, Feb. 24, 2005, pp. 884-887, vol. 433.

Machida, Y. et al., "The Deubiquitinating Enzyme BAP1 Regulates Cell Growth via Interaction with HCF-1," J. Biol. Chem., Dec. 4, 2009, pp. 34179-34188, vol. 284, No. 49.

McNamara, M. et al., "Assessment of Chromosome Copy Number in Ocular Melanoma Using Fluorescence In Situ Hybridization," Cancer Genet. Cytogenet., 1997, pp. 4-8, vol. 98.

Midena, E. et al., "In vivo detection of monosomy in eyes with medium-sized uveal melanoma using transscleral fine needle aspiration biopsy," Eur. Ophthalmol., 2006, pp. 422-425, vol. 16, No. 3 (abstract only).

Misaghi, S. et al., "Structure of the Ubiquitin Hydrolase UCH-L3 Complexed with a Suicide Substrate," J. Biol. Chem., Jan. 14, 2005, pp. 1512-1520, vol. 280, No. 2.

Misaghi, S. et al., "Association of C-Terminal Ubiquitin Hydrolase BRCA1-Associated Protein 1 with Cell Cycle Regulator Host Cell Factor 1," Mol. Cell. Biol., Apr. 2009, pp. 2181-2192, vol. 29, No. 8.

Naus, N. et al., "Characterization of Complex Chromosomal Abnormalities in Uveal Melanoma by Fluorescence In Situ Hybridization, Spectral Karyotyping, and Comparative Genomic Hybridization," Genes, Chromosomes and Cancer, Mar. 2001, pp. 267-273, vol. 30, No. 3.

Ng, S. et al., "Exome sequencing identifies the cause of a mendelian disorder," Nat. Genet., Jan. 2010, pp. 30-36, vol. 42, No. 1.

Ng, S. et al., "Targeted capture and massively parallel sequencing of 12 human exomes," Nature, Sep. 10, 2009, pp. 272-276, vol. 461.

Nishikawa, H. et al., "BRCA1-Associated Protein 1 Interferes with BRCA1/BARD1 RING Heterodimer Activity," Cancer Res., Jan. 1, 2009, pp. 111-119, vol. 69, No. 1.

Notice of Allowance dated Sep. 6, 2013 for related U.S. Appl. No. 12/989,272; 10 pages.

Office Action dated Mar. 26, 2012 for related British Patent Application No. 1116471.2; 4 pages.

Office Action dated Sep. 25, 2012 for related U.S. Appl. No. 12/989,272; 7 pages.

Office Action dated Oct. 15, 2012 for related British Patent Application No. 1116471.2; 2 pages.

METHOD FOR PREDICTING RISK OF METASTASIS

GOVERNMENTAL RIGHTS

This invention was made with government support under EY013169 and CA125970 awarded by the National Institutes of Health. The government has certain rights in the invention.

FIELD OF THE INVENTION

The invention encompasses methods and compositions for predicting the risk of metastasis.

BACKGROUND OF THE INVENTION

Once a primary tumor has metastasized, treatment of the tumor becomes more complicated, and generally speaking, survival rates decrease. Consequently, it is advantageous to determine which tumors are more likely to metastasize, so that appropriate treatment may be started as soon as possible. Many different types of tumors are capable of metastasizing. Melanomas, in particular, are capable of aggressive metastasis.

Melanoma is a malignant tumor of melanocytes, and may occur in the eye (uveal melanoma) or on the skin. Uveal melanoma is the most common intraocular malignancy. The incidence of this tumor increases with age and reaches a maximum between the $6^{th}$ and $7^{th}$ decade of life. Approximately 50% of patients die of metastases, a proportion that, despite all efforts to improve treatment, has remained constant during the last century. The average life expectancy after diagnosis of metastases is 7 months.

Around 160,000 new cases of melanoma of the skin are diagnosed worldwide each year, and according to the WHO Report about 48,000 melanoma related deaths occur worldwide per annum, which accounts for 75 percent of all deaths associated with skin cancer. Similar to uveal melanoma, when there is distant metastasis, the cancer is generally considered incurable. The five-year survival rate is less than 10%, with a median survival time of 6 to 12 months.

Due to the aggressive nature of these malignancies, there is a need in the art for methods of predicting the risk of metastasis, so that treatment may begin as early as possible.

SUMMARY OF THE INVENTION

One aspect of the invention encompasses a method for predicting the risk of metastasis of a tumor in a subject. The method comprises determining the level of expression of at least three nucleic acid sequences in a tumor sample from the subject, wherein the three nucleic acid sequences are selected from the group consisting of CDH1, ECM1, EIF1B, FXR1, HTR2B, ID2, LMCD1, LTA4H, MTUS1, RAB31, ROBO1, and SATB1. The level of expression of the nucleic acid sequences is correlated to a risk of metastasis.

Another aspect of the invention encompasses a validated data set. The data set comprises the known occurrence of melanoma metastasis correlated with the gene expression data for at least three nucleic acid sequences. At least one nucleic acid sequence is selected from the group consisting of SATB1, ECM1, E1F1B, LTA4H, and RAB31.

Yet another aspect of the invention encompasses a nucleic acid array. The array consists of nucleic acid sequences capable of hybridizing to at least three nucleic acid sequences selected from the group of nucleic acids consisting of CDH1, ECM1, EIF1B, FXR1, HTR2B, ID2, LMCD1, LTA4H, MTUS1, RAB31, ROBO1, and SATB1.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 4 depicts a series of graphs showing a predictive model for classifying tumor samples for the indicated datasets.

DETAILED DESCRIPTION OF THE INVENTION

Figure 1:
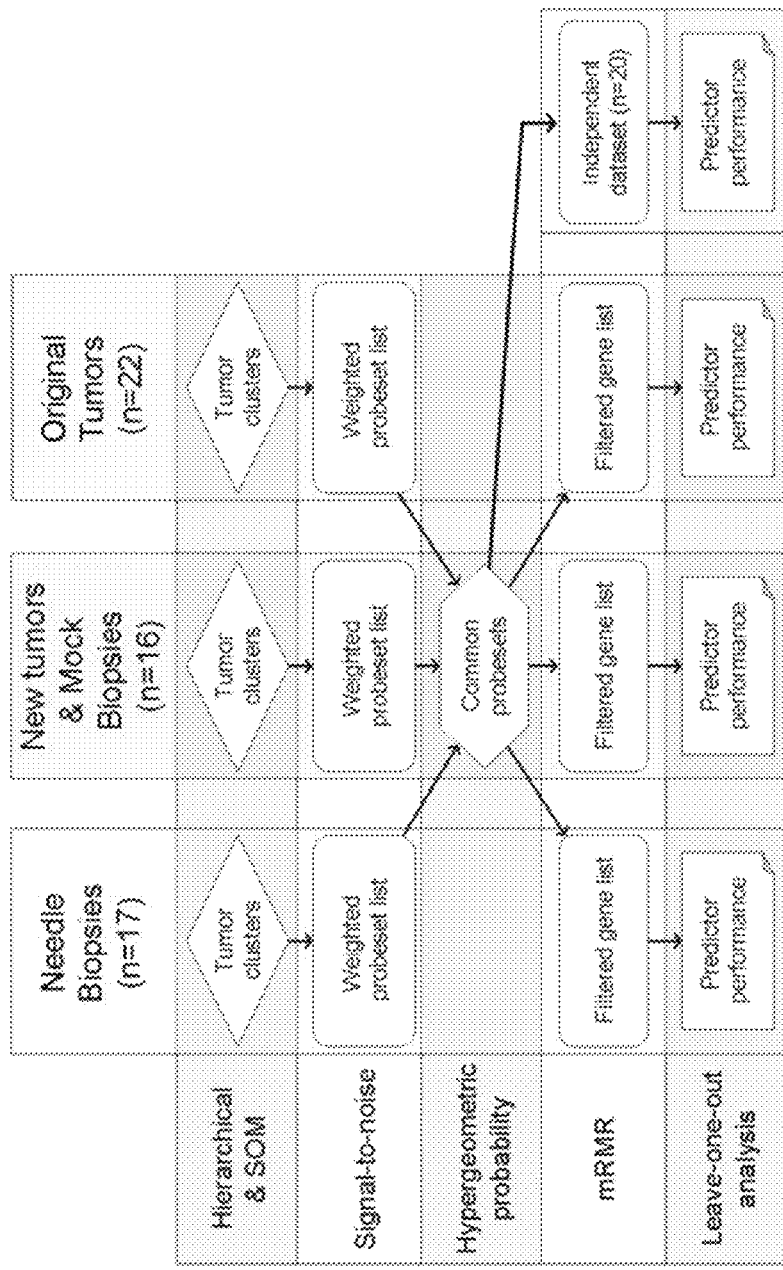
FIG. 1 depicts an illustration of the study design for Example 1.

The present invention provides a method for predicting the risk of metastasis of a tumor in a subject. In some embodiments, the tumor is a melanoma. In particular, the invention provides a method for predicting if a subject has a high risk or a low risk for metastasis. Advantageously, a subject that knows the risk for metastasis may make a more informed decision about treatment options. Additionally, the invention provides a validated data set and a nucleic acid array for use in the method.

I. Method

Generally speaking, the method comprises determining the level of expression of at least three genes selected from the group comprising cadherin 1, type 1, E-cadherin (epithelial) (CDH1); extracellular matrix protein 1 (ECM1); eukaryotic translation initiation factor 1B (E1F1B); fragile X mental retardation, autosomal homolog 1 (FXR1); 5-hydroxytryptamine (serotonin) receptor 2B (HTR2B); inhibitor of DNA binding 2 (ID2); LIM and cysteine-rich domains 1 (LMCD1); leukotriene A4 hydrolase (LTA4H); mitochondrial tumor suppressor 1 (MTUS1); RAB31; roundabout, axon guidance receptor, homolog 1 (ROBO1); and SATB homeobox 1 (SATB1) in a tumor sample from the subject, and correlating the level of expression with a risk of metastasis. In certain embodiments, the tumor is a melanoma. By way of non-limiting example, the tumor may be a uveal melanoma, a cutaneous melanoma, or a mucosal melanoma. In other embodiments, the tumor may be a sarcoma or a carcinoma.

(a) Tumor Sample

A tumor sample may be derived from a melanoma tumor, including uveal melanoma samples and cutaneous melanoma samples. Additionally, the tumor sample may be derived from a sarcoma or a carcinoma. For instance, non-limiting examples of carcinomas may include hepatocellular carcinoma and gastric carcinoma. The tumor sample may also be derived from inflammatory breast cancer.

Methods of collecting tumor samples are well known in the art. For instance, a tumor sample may be obtained from a surgically resected tumor. In uveal melanoma, for example, a tumor sample may be obtained from an enucleation procedure. Alternatively, the tumor sample may be obtained from a biopsy. This is advantageous when the tumor is small enough to not require resection. In an exemplary embodiment, the tumor sample may be obtained from a fine needle biopsy, also known as a needle aspiration biopsy (NAB), a fine needle aspiration cytology (FNAC), a fine needle aspiration biopsy (FNAB) or a fine needle aspiration (FNA). A tumor sample may be fresh or otherwise stored so as to reduce nucleic acid degradation. For instance, a tumor sample may be a fresh frozen tumor sample or a formalin-fixed paraffin embedded tumor sample.

In certain embodiments, the method of the invention may be performed with a tumor sample comprising about five cells or less. In one embodiment, the tumor sample may comprise about 1, 2, 3, 4, 5, 6, 7, 8, 9, 10, 11, 12, 13, 14, 15 or more cells. In another embodiment, the tumor sample may comprise 20, 25, 30, 35, 40 or more cells.

(b) Nucleic Acid Sequences

A method of the invention comprises determining the level of expression of at least three nucleic acid sequences selected from the group comprising CDH1, ECM1, EIF1B, FXR1, HTR2B, ID2, LMCD1, LTA4H, MTUS1, RAB31, ROBO1, and SATB1. In one embodiment, the method comprises determining the level of expression of at least four, at least five, at least six, at least seven, at least eight, at least nine, at least ten, at least eleven, or at least twelve nucleic acid sequences selected from the group comprising CDH1, ECM1, EIF1B, FXR1, HTR2B, ID2, LMCD1, LTA4H, MTUS1, RAB31, ROBO1, and SATB1.

In another embodiment, the method comprises determining the level of expression of at least three nucleic acid sequences selected from the group consisting of CDH1, ECM1, EIF1B, FXR1, HTR2B, ID2, LMCD1, LTA4H, MTUS1, RAB31, ROBO1, and SATB1. In yet another embodiment, the method comprises determining the level of expression of at least four, at least five, at least six, at least seven, at least eight, at least nine, at least ten, or at least eleven nucleic acid sequences selected from the group consisting of CDH1, ECM1, EIF1B, FXR1, HTR2B, ID2, LMCD1, LTA4H, MTUS1, RAB31, ROBO1, and SATB1. In yet another embodiment, the method comprises determining the level of expression of CDH1, ECM1, EIF1B, FXR1, HTR2B, ID2, LMCD1, LTA4H, MTUS1, RAB31, ROBO1, and SATB1.

In certain embodiments, the method comprises determining the level of expression of at least three or at least four nucleic acid sequences selected from the group consisting of HTR2B, LMCD1, MTUS1, ROBO1, and SATB1. In other embodiments, the method comprises determining the level of expression of HTR2B, LMCD1, MTUS1, ROBO1, and SATB1.

In further embodiments, the method comprises determining the level of expression of a combination of nucleic acid sequences listed in Table A. In still yet another embodiment, the method comprises determining the level of expression of a combination of nucleic acid sequences listed in Table A, and at least one, at least two, at least three, at least four, at least five, at least six, at least seven, at least eight, or at least nine additional nucleic acid sequences selected from the group comprising CDH1, ECM1, EIF1B, FXR1, HTR2B, ID2, LMCD1, LTA4H, MTUS1, RAB31, ROBO1, and SATB1.

TABLE A

| | | |
|---|---|---|
| CDH1 | ECM1 | EIF1B |
| CDH1 | ECM1 | FXR1 |
| CDH1 | ECM1 | HTR2B |
| CDH1 | ECM1 | ID2 |
| CDH1 | ECM1 | LMCD1 |
| CDH1 | ECM1 | LTA4H |
| CDH1 | ECM1 | MTUS1 |
| CDH1 | ECM1 | RAB31 |
| CDH1 | ECM1 | ROBO1 |
| CDH1 | ECM1 | SATB1 |
| CDH1 | EIF1B | FXR1 |
| CDH1 | EIF1B | HTR2B |
| CDH1 | EIF1B | ID2 |
| CDH1 | EIF1B | LMCD1 |
| CDH1 | EIF1B | LTA4H |
| CDH1 | EIF1B | MTUS1 |
| CDH1 | EIF1B | RAB31 |
| CDH1 | EIF1B | ROBO1 |
| CDH1 | EIF1B | SATB1 |
| CDH1 | FXR1 | HTR2B |
| CDH1 | FXR1 | ID2 |
| CDH1 | FXR1 | LMCD1 |
| CDH1 | FXR1 | LTA4H |
| CDH1 | FXR1 | MTUS1 |
| CDH1 | FXR1 | RAB31 |
| CDH1 | FXR1 | ROBO1 |
| CDH1 | FXR1 | SATB1 |
| CDH1 | HTR2B | ID2 |
| CDH1 | HTR2B | LMCD1 |
| CDH1 | HTR2B | LTA4H |
| CDH1 | HTR2B | MTUS1 |
| CDH1 | HTR2B | RAB31 |
| CDH1 | HTR2B | ROBO1 |
| CDH1 | HTR2B | SATB1 |
| CDH1 | ID2 | LMCD1 |
| CDH1 | ID2 | LTA4H |
| CDH1 | ID2 | MTUS1 |
| CDH1 | ID2 | RAB31 |
| CDH1 | ID2 | ROBO1 |
| CDH1 | ID2 | SATB1 |
| CDH1 | LMCD1 | LTA4H |
| CDH1 | LMCD1 | MTUS1 |
| CDH1 | LMCD1 | RAB31 |
| CDH1 | LMCD1 | ROBO1 |
| CDH1 | LMCD1 | SATB1 |
| CDH1 | LTA4H | MTUS1 |
| CDH1 | LTA4H | RAB31 |
| CDH1 | LTA4H | ROBO1 |
| CDH1 | LTA4H | SATB1 |
| CDH1 | MTUS1 | RAB31 |
| CDH1 | MTUS1 | ROBO1 |
| CDH1 | MTUS1 | SATB1 |
| CDH1 | RAB31 | ROBO1 |
| CDH1 | RAB31 | SATB1 |
| CDH1 | ROBO1 | SATB1 |
| ECM1 | EIF1B | FXR1 |
| ECM1 | EIF1B | HTR2B |
| ECM1 | EIF1B | ID2 |
| ECM1 | EIF1B | LMCD1 |
| ECM1 | EIF1B | LTA4H |
| ECM1 | EIF1B | MTUS1 |
| ECM1 | EIF1B | RAB31 |
| ECM1 | EIF1B | ROBO1 |
| ECM1 | EIF1B | SATB1 |
| ECM1 | FXR1 | HTR2B |
| ECM1 | FXR1 | ID2 |
| ECM1 | FXR1 | LMCD1 |
| ECM1 | FXR1 | LTA4H |
| ECM1 | FXR1 | MTUS1 |
| ECM1 | FXR1 | RAB31 |
| ECM1 | FXR1 | ROBO1 |

TABLE A-continued

| | | |
|---|---|---|
| ECM1 | FXR1 | SATB1 |
| ECM1 | HTR2B | ID2 |
| ECM1 | HTR2B | LMCD1 |
| ECM1 | HTR2B | LTA4H |
| ECM1 | HTR2B | MTUS1 |
| ECM1 | HTR2B | RAB31 |
| ECM1 | HTR2B | ROBO1 |
| ECM1 | HTR2B | SATB1 |
| ECM1 | ID2 | LMCD1 |
| ECM1 | ID2 | LTA4H |
| ECM1 | ID2 | MTUS1 |
| ECM1 | ID2 | RAB31 |
| ECM1 | ID2 | ROBO1 |
| ECM1 | ID2 | SATB1 |
| ECM1 | LMCD1 | LTA4H |
| ECM1 | LMCD1 | MTUS1 |
| ECM1 | LMCD1 | RAB31 |
| ECM1 | LMCD1 | ROBO1 |
| ECM1 | LMCD1 | SATB1 |
| ECM1 | LTA4H | MTUS1 |
| ECM1 | LTA4H | RAB31 |
| ECM1 | LTA4H | ROBO1 |
| ECM1 | LTA4H | SATB1 |
| ECM1 | MTUS1 | RAB31 |
| ECM1 | MTUS1 | ROBO1 |
| ECM1 | MTUS1 | SATB1 |
| ECM1 | RAB31 | ROBO1 |
| ECM1 | RAB31 | SATB1 |
| ECM1 | ROBO1 | SATB1 |
| EIF1B | FXR1 | HTR2B |
| EIF1B | FXR1 | ID2 |
| EIF1B | FXR1 | LMCD1 |
| EIF1B | FXR1 | LTA4H |
| EIF1B | FXR1 | MTUS1 |
| EIF1B | FXR1 | RAB31 |
| EIF1B | FXR1 | ROBO1 |
| EIF1B | FXR1 | SATB1 |
| EIF1B | HTR2B | ID2 |
| EIF1B | HTR2B | LMCD1 |
| EIF1B | HTR2B | LTA4H |
| EIF1B | HTR2B | MTUS1 |
| EIF1B | HTR2B | RAB31 |
| EIF1B | HTR2B | ROBO1 |
| EIF1B | HTR2B | SATB1 |
| EIF1B | ID2 | LMCD1 |
| EIF1B | ID2 | LTA4H |
| EIF1B | ID2 | MTUS1 |
| EIF1B | ID2 | RAB31 |
| EIF1B | ID2 | ROBO1 |
| EIF1B | ID2 | SATB1 |
| EIF1B | LMCD1 | LTA4H |
| EIF1B | LMCD1 | MTUS1 |
| EIF1B | LMCD1 | RAB31 |
| EIF1B | LMCD1 | ROBO1 |
| EIF1B | LMCD1 | SATB1 |
| EIF1B | LTA4H | MTUS1 |
| EIF1B | LTA4H | RAB31 |
| EIF1B | LTA4H | ROBO1 |
| EIF1B | LTA4H | SATB1 |
| EIF1B | MTUS1 | RAB31 |
| EIF1B | MTUS1 | ROBO1 |
| EIF1B | MTUS1 | SATB1 |
| EIF1B | RAB31 | ROBO1 |
| EIF1B | RAB31 | SATB1 |
| EIF1B | ROBO1 | SATB1 |
| FXR1 | HTR2B | ID2 |
| FXR1 | HTR2B | LMCD1 |
| FXR1 | HTR2B | LTA4H |
| FXR1 | HTR2B | MTUS1 |
| FXR1 | HTR2B | RAB31 |
| FXR1 | HTR2B | ROBO1 |
| FXR1 | HTR2B | SATB1 |
| FXR1 | ID2 | LMCD1 |
| FXR1 | ID2 | LTA4H |
| FXR1 | ID2 | MTUS1 |
| FXR1 | ID2 | RAB31 |
| FXR1 | ID2 | ROBO1 |
| FXR1 | ID2 | SATB1 |
| FXR1 | LMCD1 | LTA4H |
| FXR1 | LMCD1 | MTUS1 |

TABLE A-continued

| | | |
|---|---|---|
| FXR1 | LMCD1 | RAB31 |
| FXR1 | LMCD1 | ROBO1 |
| FXR1 | LMCD1 | SATB1 |
| FXR1 | LTA4H | MTUS1 |
| FXR1 | LTA4H | RAB31 |
| FXR1 | LTA4H | ROBO1 |
| FXR1 | LTA4H | SATB1 |
| FXR1 | MTUS1 | RAB31 |
| FXR1 | MTUS1 | ROBO1 |
| FXR1 | MTUS1 | SATB1 |
| FXR1 | RAB31 | ROBO1 |
| FXR1 | RAB31 | SATB1 |
| FXR1 | ROBO1 | SATB1 |
| HTR2B | ID2 | LMCD1 |
| HTR2B | ID2 | LTA4H |
| HTR2B | ID2 | MTUS1 |
| HTR2B | ID2 | RAB31 |
| HTR2B | ID2 | ROBO1 |
| HTR2B | ID2 | SATB1 |
| HTR2B | LMCD1 | LTA4H |
| HTR2B | LMCD1 | MTUS1 |
| HTR2B | LMCD1 | RAB31 |
| HTR2B | LMCD1 | ROBO1 |
| HTR2B | LMCD1 | SATB1 |
| HTR2B | LTA4H | MTUS1 |
| HTR2B | LTA4H | RAB31 |
| HTR2B | LTA4H | ROBO1 |
| HTR2B | LTA4H | SATB1 |
| HTR2B | MTUS1 | RAB31 |
| HTR2B | MTUS1 | ROBO1 |
| HTR2B | MTUS1 | SATB1 |
| HTR2B | RAB31 | ROBO1 |
| HTR2B | RAB31 | SATB1 |
| HTR2B | ROBO1 | SATB1 |
| ID2 | LMCD1 | LTA4H |
| ID2 | LMCD1 | MTUS1 |
| ID2 | LMCD1 | RAB31 |
| ID2 | LMCD1 | ROBO1 |
| ID2 | LMCD1 | SATB1 |
| ID2 | LTA4H | MTUS1 |
| ID2 | LTA4H | RAB31 |
| ID2 | LTA4H | ROBO1 |
| ID2 | LTA4H | SATB1 |
| ID2 | MTUS1 | RAB31 |
| ID2 | MTUS1 | ROBO1 |
| ID2 | MTUS1 | SATB1 |
| ID2 | RAB31 | ROBO1 |
| ID2 | RAB31 | SATB1 |
| ID2 | ROBO1 | SATB1 |
| LMCD1 | LTA4H | MTUS1 |
| LMCD1 | LTA4H | RAB31 |
| LMCD1 | LTA4H | ROBO1 |
| LMCD1 | LTA4H | SATB1 |
| LMCD1 | MTUS1 | RAB31 |
| LMCD1 | MTUS1 | ROBO1 |
| LMCD1 | MTUS1 | SATB1 |
| LMCD1 | RAB31 | ROBO1 |
| LMCD1 | RAB31 | SATB1 |
| LMCD1 | ROBO1 | SATB1 |
| LTA4H | MTUS1 | RAB31 |
| LTA4H | MTUS1 | ROBO1 |
| LTA4H | MTUS1 | SATB1 |
| LTA4H | RAB31 | ROBO1 |
| LTA4H | RAB31 | SATB1 |
| LTA4H | ROBO1 | SATB1 |
| MTUS1 | RAB31 | ROBO1 |
| MTUS1 | RAB31 | SATB1 |
| MTUS1 | ROBO1 | SATB1 |
| RAB31 | ROBO1 | SATB1 |

(c) Level of Expression

Determining the level of expression of a nucleic acid sequence, comprises, in part, measuring the level of mRNA expression for a nucleic acid sequence in a tumor sample. Methods of measuring the level of mRNA in a tumor sample for a particular nucleic acid sequence, or several sequences, are known in the art. For instance, in one embodiment, the level of mRNA expression may be determined using a nucleic acid microarray. Methods of using a nucleic acid microarray are well and widely known in the art. For instance, see the Examples. In another embodiment, the level of mRNA expression may be determined using PCR. In these embodiments, the mRNA is typically reverse transcribed into cDNA using methods known in the art. Methods of PCR are well and widely known in the art, and may include quantitative PCR, semi-quantitative PCR, multiplex PCR, or any combination thereof. In yet another embodiment, the level of mRNA expression may be determined using a TDLA (TaqMan low density array) card manufactured by Applied Biosciences, or a similar assay.

The level of mRNA expression may be measured by measuring an entire mRNA transcript for a nucleic acid sequence, or measuring a portion of the mRNA transcript for a nucleic acid sequence. For instance, if a nucleic acid array is utilized to measure the level of mRNA expression, the array may comprise a probe for a portion of the mRNA of the nucleic acid sequence of interest, or the array may comprise a probe for the full mRNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art.

Methods of extracting RNA from a tumor sample are known in the art, and detailed in Example 1 and 2 below.

The level of expression may or may not be normalized to the level of a control gene. Such a control gene should have a constant expression in a tumor sample, regardless of the risk for metastasis of the tumor. This allows comparisons between assays that are performed on difference occasions. For instance, the control gene may be mitochondrial ribosomal protein S21 (MRPS21), Sin3A-associated protein, 130 kDa (SAP130), RNA binding motif protein 23 (RBM23), or any combination thereof.

(d) Correlating the Level of Expression with a Risk of Metastasis

A method of the invention comprises correlating the level of expression of at least three genes, as detailed above, with a risk of metastasis. In one embodiment, the risk of metastasis is high. For instance, the risk may be greater than about 50%, 55%, 60%, 65%, 70%, 75%, 80%, 85%, 90%, or 95%. In particular embodiments, the risk may continue to increase over time. For example, the risk may be about 50% at five years and 90% for ten years.

In another embodiment, the risk of metastasis is low. For instance, the risk may be less than about 20%, 15%, 10%, or 5%. In particular embodiments, the risk may be low, but may still increase over time. For example, the risk may be about 5% at five years and 10% at ten years.

The level of expression for at least three nucleic acid sequences may be used in an algorithm to determine if the risk of metastasis is high or low for a particular tumor sample. Suitable algorithms may include a support vector machine (SVM) algorithm, a weighted-voting (WV) algorithm, a regularized discriminant analysis (RDA), or prediction analysis of microarrays (PAM). Generally speaking, these algorithms compare the level of expression to a validated data set, and determine whether the levels of expression correlate with a high risk of metastasis or a low risk of metastasis. Generally speaking, these algorithms compare the level of expression to a validated data set, and determine whether the levels of expression correlate with a high risk of metastasis or a low risk of metastasis. A "validated data set," as used herein, refers to a set of nucleic acid sequence expression data wherein the correlation between the expression level of one or more nucleic acid sequences and the occurrence of metastasis is already known for the nucleic acid sequences within the set. For more details, see the Examples. In particular, Example 3 details a validated data set for nucleic acid sequences selected from the group CDH1, ECM1, EIF1B, FXR1, HTR2B, ID2, LMCD1, LTA4H, MTUS1, RAB31, ROBO1, and SATB1.

The level of expression of one or more control nucleic acid sequences may also be used in such algorithms. As stated above, such a control nucleic acid sequence should have a constant expression in a tumor sample, regardless of the risk for metastasis of the tumor. In one embodiment, the level of expression of two, three, or more than three control nucleic acid sequences may be used. For instance, the level of expression of MRPS21, SAP130, and RBM23 may be used as a control.

The correlation between the level of expression and the risk of metastasis derived from an algorithm should typically be statistically significant. For instance, for a given tumor sample, if two different algorithms predicted a discordant risk of metastasis, the preferred prediction is the one that is statistically significant, or if both are statistically significant, the algorithm that provides the most statistically significant determination is usually used.

Generally speaking, a high risk of metastasis may be correlated with increased expression of CDH1, ECM1, HTR2B, and RAB31, and decreased expression of E1F1B, FXR1, ID2, LMCD1, LTA4H, MTUS1, ROBO1, and SATB1.

II. Validated Data Set

Another aspect of the present invention encompasses a validated data set. As detailed above, a validated data set encompasses the nucleic acid sequence expression data for at least three of the nucleic acid sequences comprising the group CDH1, ECM1, EIF1B, FXR1, HTR2B, ID2, LMCD1, LTA4H, MTUS1, RAB31, ROBO1, and SATB1 for a given tumor sample, correlated with the known occurrence of metastasis for that tumor sample. In another embodiment, a validated data set may encompass the nucleic acid sequence expression data for at least five nucleic acid sequences selected from the group consisting of CDH1, ECM1, EIF1B, FXR1, HTR2B, ID2, LMCD1, LTA4H, MTUS1, RAB31, ROBO1, and SATB1. In yet another embodiment, a validated data set may encompass the nucleic acid sequence expression data for HTR2B, LMCD1, MTUS1, ROBO1, and SATB1. In still another embodiment, a validated data set may encompass the nucleic acid sequence expression data for CDH1, ECM1, EIF1B, FXR1, HTR2B, ID2, LMCD1, LTA4H, MTUS1, RAB31, ROBO1, and SATB1.

A validated data set may be digitally-encoded on a computer-readable medium. The term "computer-readable medium" as used herein refers to a medium that participates in providing instructions to a processor for execution. Such a medium may take many forms, including but not limited to non-volatile media, volatile media, and transmission media. Non-volatile media may include, for example, optical or magnetic disks. Volatile media may include dynamic memory. Transmission media may include coaxial cables, copper wire and fiber optics. Transmission media may also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, or other magnetic medium, a CD-ROM, CDRW, DVD, or other optical medium, punch cards, paper tape, optical mark sheets, or other physical medium with patterns of holes or other optically recognizable indicia, a RAM, a PROM, and EPROM, a FLASH-EPROM, or other memory chip or cartridge, a carrier wave, or other medium from which a computer can read.

III. Nucleic Acid Array

Yet another aspect of the invention encompasses a nucleic acid array. Such an array may be used to determine the expression level of a nucleic acid in a tumor sample. An array may be comprised of a substrate having disposed thereon nucleic acid sequences capable of hybridizing to at least three nucleic acid sequences selected from the group of nucleic acids consisting of CDH1, ECM1, EIF1B, FXR1, HTR2B, ID2, LMCD1, LTA4H, MTUS1, RAB31, ROBO1, and SATB1. For instance, the array may consist of nucleic acid sequences capable of hybridizing to a group of three nucleic acid sequences depicted in Table A. In one embodiment, the array may consist of nucleic acid sequences capable of hybridizing to at least five nucleic acid sequences selected from the group consisting of CDH1, ECM1, EIF1B, FXR1, HTR2B, ID2, LMCD1, LTA4H, MTUS1, RAB31, ROBO1, and SATB1. In another embodiment, the array may consist of nucleic acid sequences capable of hybridizing to HTR2B, LMCD1, MTUS1, ROBO1, and SATB1. In yet another embodiment, the array may consist of nucleic acid sequences capable of hybridizing to CDH1, ECM1, E1F1B, FXR1, HTR2B, ID2, LMCD1, LTA4H, MTUS1, RAB31, ROBO1, and SATB1. In each of the above embodiments, the methods for selecting nucleic acid sequences capable of hybridizing to at least three nucleic acid sequences selected from the group of nucleic acids consisting of CDH1, ECM1, E1F1B, FXR1, HTR2B, ID2, LMCD1, LTA4H, MTUS1, RAB31, ROBO1, and SATB1 are known in the art.

Several substrates suitable for the construction of arrays are known in the art. The substrate may be a material that may be modified to contain discrete individual sites appropriate for the attachment or association of the nucleic acid and is amenable to at least one detection method. Alternatively, the substrate may be a material that may be modified for the bulk attachment or association of the nucleic acid and is amenable to at least one detection method. Non-limiting examples of substrate materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. In an exemplary embodiment, the substrates may allow optical detection without appreciably fluorescing.

A substrate may be planar, a substrate may be a well, i.e. a 1534-, 384-, or 96-well plate, or alternatively, a substrate may be a bead. Additionally, the substrate may be the inner surface of a tube for flow-through sample analysis to minimize sample volume. Similarly, the substrate may be flexible, such as a flexible foam, including closed cell foams made of particular plastics. Other suitable substrates are known in the art.

The nucleic acid or biomolecules may be attached to the substrate in a wide variety of ways, as will be appreciated by those in the art. The nucleic acid may either be synthesized first, with subsequent attachment to the substrate, or may be directly synthesized on the substrate. The substrate and the nucleic acid may both be derivatized with chemical functional groups for subsequent attachment of the two. For example, the substrate may be derivatized with a chemical functional group including, but not limited to, amino groups, carboxyl groups, oxo groups or thiol groups. Using these functional groups, the nucleic acid may be attached using functional groups on the biomolecule either directly or indirectly using linkers.

The nucleic acid may also be attached to the substrate non-covalently. For example, a biotinylated nucleic acid can be prepared, which may bind to surfaces covalently coated with streptavidin, resulting in attachment. Alternatively, a nucleic acid or nucleic acid s may be synthesized on the surface using techniques such as photopolymerization and photolithography. Additional methods of attaching biomolecules to arrays and methods of synthesizing biomolecules on substrates are well known in the art, i.e. VLSIPS technology from Affymetrix (e.g., see U.S. Pat. No. 6,566,495, and Rockett and Dix, Xenobiotica 30(2):155-177, each of which is hereby incorporated by reference in its entirety).

In one embodiment, the nucleic acid or nucleic acid s attached to the substrate are located at a spatially defined address of the array. Arrays may comprise from about 1 to about several hundred thousand addresses. A nucleic acid may be represented more than once on a given array. In other words, more than one address of an array may be comprised of the same nucleic acid. In some embodiments, two, three, or more than three addresses of the array may be comprised of the same nucleic acid. In certain embodiments, the array may comprise control nucleic acids and/or control addresses. The controls may be internal controls, positive controls, negative controls, or background controls.

Furthermore, the nucleic acids used for the array may be labeled. One skilled in the art understands that the type of label selected depends in part on how the array is being used. Suitable labels may include fluorescent labels, chromagraphic labels, chemi-luminescent labels, FRET labels, etc. Such labels are well known in the art.

Definitions

As used herein, "carcinoma" refers to a malignant tumor derived from an epithelial cell.

As used herein, "melanoma" refers to a malignant tumor of a melanocyte. In one embodiment, the melanoma may be a uveal melanoma. In another embodiment, the melanoma may be a cutaneous melanoma.

As used herein, "sarcoma" refers to a malignant tumor derived from connective tissue.

As used herein, "subject" refers to a mammal capable of being afflicted with a carcinoma, melanoma, or sarcoma, and that expresses homologs to at least three nucleic acid sequences selected from the group comprising CDH1, ECM1, EIF1B, FXR1, HTR2B, ID2, LMCD1, LTA4H, MTUS1, RAB31, ROBO1, and SATB1. In addition to having a substantially similar biological function, a homolog of an above listed nucleic acid sequence will also typically share substantial sequence similarity with the nucleic acid sequence. For example, suitable homologs preferably share at least 30% sequence homology, more preferably, 50%, and even more preferably, are greater than about 75% homologous in sequence. In determining whether a sequence is homologous to an above listed nucleic acid sequence, sequence similarity may be determined by conventional algorithms, which typically allow introduction of a small number of gaps in order to achieve the best fit. In particular, "percent homology" of two polypeptides or two nucleic acid sequences may be determined using the algorithm of Karlin and Altschul [(Proc. Natl. Acad. Sci. USA 87, 2264 (1993)]. Such an algorithm is incorporated into the NBLAST and XBLAST programs of Altschul, et al. (J. Mol. Biol. 215, 403 (1990)). BLAST nucleotide searches may be performed with the NBLAST program to obtain nucleotide sequences homologous to a nucleic acid molecule of the invention. Equally, BLAST protein searches may be performed with the XBLAST program to obtain amino acid sequences that are homologous to a polypeptide of the invention. To obtain gapped alignments for comparison purposes, Gapped BLAST is utilized as described in Altschul, et al. (Nucleic Acids Res. 25, 3389 (1997)). When utilizing BLAST and Gapped BLAST programs, the default parameters of the respective programs (e.g., XBLAST and NBLAST) are employed. See http://www.ncbi.nlm.nih.gov for more details. In an exemplary embodiment, the subject is human. In certain embodiments, the subject may have a carcinoma, sarcoma, or melanoma. In other embodiments, the subject may be suspected of having a carcinoma, sarcoma, or melanoma.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1

Fine Needle Biopsy Tumor Samples

Transcriptomic profiling has previously been reported only on larger pieces of uveal melanoma tissue obtained at enucleation. Enucleation is performed in only approximately 10% of uveal melanoma patients. For the remaining ~90% of patients who are treated with globe-sparing modalities, such as radiotherapy (1), transcriptomic profiling would be more useful if it could be performed on fine needle aspirates before eye-sparing treatments.

There were a number of possible obstacles to the successful transfer of transcription-based classifications to a biopsy platform. Because intraocular biopsy requires a very small needle size (25-gauge) (6), it was unclear whether the material obtained would be sufficient for microarray-based transcriptomic profiling. In addition, the effects of the small needle size on sampling errors were unknown. Furthermore, the methodological differences in the preparation of RNA from solid tumor tissue versus fine needle aspirates could affect the measurement of RNA transcripts. The purpose of this study was to explore the feasibility of transcription-based classification of uveal melanomas using fine needle aspirates.

Preparation of RNA Samples

All studies were approved by the Human Studies Committee at Washington University, and informed consent was obtained from each subject. Fine needle biopsies were performed using a 25-gauge needle on uveal melanomas before radiotherapy as previously described. (6) Fine needle aspirates were divided into samples for cytologic diagnosis and RNA analysis. The samples for RNA analysis were expelled into an empty RNase-free tube in the operating room. The empty syringe was filled with 200 µl of extraction buffer from the PicoPure RNA isolation kit (Arcturus, Mountain View, Calif.), which was then transferred to the same tube to collect any additional tumor cells lodged in the needle hub. The contents of the tube were incubated at 42° C. for 30 minutes. Immediately following enucleation, and before opening the eye, mock biopsies were obtained through the sclera in a fashion identical to the actual biopsies. The eye was then opened, and a large piece of matching tumor tissue was obtained, snap frozen, and prepared for RNA analysis as previously described. (2) RNA was isolated using the Pico-Pure kit (including the optional DNase step), which yielded about 100 ng to 1.5 µg of total RNA per aspirate using the NanoDrop 1000 system (Wilmington, Del.). RNA samples were stored at −80° C. until sent to the Siteman Cancer Center Gene Chip Facility for amplification using the Affymetrix Genechip 3' Amplification 2-Cycle cDNA Synthesis Kit (Affymetrix, Santa Clara, Calif.). Amplified cDNA samples were hybridized overnight to Hu133Av2 chips in the Genechip Hybridization Oven Model 640. Chips were washed using the GeneChip Fluidics station 450, and gene expression measured on the Affymetrix Genechip Scanner. For specimens sent to St. Louis from San Francisco, tubes were placed on dry ice and mailed by overnight courier, after which they were incubated at 42° C. for 30 minutes and handled as described for the other biopsy samples. No RNA degradation was observed for these samples.

Analysis of Microarray Expression Profiles

All new transcriptomic profiles obtained on Hu133Av2 chips and our previous profiles obtained on Hu133A chips (2) were normalized by Robust Multiarray Averaging using RMAexpress (http://rmaexpress.bmbolstad.com). The Tschentscher dataset obtained on HG-U95Av2 chips (3) was kindly provided by the authors and was not normalized with RMA. For all analyses except minimal redundancy/maximal relevance (mRMR), expression data were log 2 transformed. Probe sets were filtered for a median significance P value<0.05 and gene expression variance>1 across all specimens (to eliminate genes that did not vary substantially between tumors). Hierarchical clustering was performed with Dchip (http://biosun1.harvard.edu/complab/dchip/) using 1-correlation for the distance metric, centroid linkage method, and gene ordering by cluster tightness. Probe sets were ranked for ability to discriminate tumor classes by signal-to-noise algorithm using GeneCluster2 software (http://www.broad.mit.edu/cancer/software/genecluster2/gc2.html), which was also used to generate a predictive test using a weighted voting algorithm. Class predictions were analyzed by leave-one-out cross validation. Confidence scores were calculated by GeneCluster software as described.(7) Rank order of discriminating probe sets to be entered stepwise into the predictive test for cross validation were determined with mRMR software (http://miracle.lbl.gov/proj/mRMR/), using mutual information difference as the feature selection scheme and ±0.5 standard deviations as a threshold for discretizing expression values. Significance of discriminating probe set overlap was determined using hypergeometric probability using the PROBHYBR function of SAS 9.0 statistical software (SAS Institute, Cary, N.C.) as previously described. (8)

Analysis of RNA from Ocular Biopsy Specimens

The study goal was to evaluate the feasibility of molecular prognostic testing in uveal melanomas using transcriptomic profiles from fine needle biopsy specimens. We used a series of statistical techniques to analyze four independent transcriptomic profile datasets derived from 1) eight uveal melanomas obtained at eye removal (denoted by the prefix MM) and eight mock needle biopsy samples from the same tumors (denoted MB), 2) 17 fine needle biopsies of uveal melanomas before radiotherapy (denoted NB), 3) 22 uveal melanomas from our original published dataset (denoted OrigMM),[2] and 4) 20 uveal melanomas published by another laboratory (denoted Tschentscher). (3) The study design is summarized in FIG. 1. Clinical and pathological features are summarized in Table 1. To conserve the small amounts of RNA obtained from the needle aspirates, RNA concentrations were not measured directly, but rather, the RNA quality and hybridization characteristics were assessed by the background score and scaling factor supplied by the Affymetrix software. The background score, an indicator of nonspecific binding to the array, was only slightly higher for the NB group (mean, 2.3 units±0.1 SE) compared with the MB group (mean, 1.7 units±0.04 SE) and the MM group (mean, 1.6 units±0.07 SE). The scaling factor, a multiplication function that is inversely proportional to the overall chip hybridization signal intensity, was lower for the NB group (mean, 9.6 units±2.2 SE) compared with the MB group (mean, 17.5 units±4.9 SE) and the MM group (mean, 13.1 units±0.8 SE). Therefore, the NB chips exhibited good hybridization characteristics with acceptable background, indicating that the fine needle aspirates yielded RNA of adequate quantity and quality for direct transcriptomic profiling. Of note, eight specimens obtained from the San Francisco location and shipped to St. Louis showed no decrease in RNA quality or hybridization characteristics compared with the St. Louis specimens.

TABLE 1

| | Datasets | | |
| --- | --- | --- | --- |
| Feature | OrigMM | MM-MB | NB |
| Mean age (range) | 61 (25-82) | 59 (37-74) | 60 (25-88) |
| Mean largest tumor diameter, millimeters (range) | 18 (10-26) | 17 (10-22) | 13 (5-18) |
| Mean tumor thickness, millimeters (range) | 10 (4-16) | 10 (5-14) | 9 (3-18) |
| Tumor location | Anterior, 9 (41%) Posterior, 13 (59%) | Anterior, 5 (63%) Posterior, 3 (37%) | Anterior, 8 (47%) Posterior, 9 (53%) |
| Cytology | Spindle, 8 (36%) Mixed, 8 (36%) | Spindle, 2 (25%) Mixed, 2 (25%) | Spindle, 6 (35%) Mixed, 4 (24%) |

TABLE 1-continued

| Feature | Datasets | | |
|---|---|---|---|
| | OrigMM | MM-MB | NB |
| | Epithelioid, 6 (27%) | Epithelioid, 4 (50%) | Epithelioid, 4 (24%) |
| | | | Not available, 3 (17%) |
| Molecular class | Class 1, 14 (64%) | Class 1, 3 (37%) | Class 1, 9 (53%) |
| | Class 2, 8 (36%) | Class 2, 5 (63%) | Class 2, 8 (47%) |

Assessment of Sampling Error Using Postenucleation Mock Biopsy Specimens

The possibility that tumor cells obtained in a biopsy specimen may not be representative of the entire tumor is a concern with the small amount of material obtained from intraocular biopsies. (9) We evaluated the similarity of transcriptomic profiles between the 16 MM and MB samples using unsupervised hierarchical clustering. Because the MM samples represented about 25% of the total tumor volume, they were assumed to represent adequately the overall transcriptomic profile of the tumor. Probe sets were filtered for a median significance P value<0.05 and gene expression variance>1 across all specimens (to eliminate genes that did not vary substantially between tumors), which resulted in 806 probe sets. For each MB specimen, the matching MM specimen demonstrated the shortest linkage distance (ie, the most similar transcriptomic profile) (FIG. 2), indicating that each MB was more similar to its paired MM than to any of the other MB or MM specimens (P<0.0001). This similarity was remarkable, considering the relative homogeneity in gene expression between allogeneic uveal melanomas and the methodological differences in RNA preparation for the MM versus the MB samples. These results show that transcriptomic profiles obtained from fine needle aspirates closely approximate larger tumor samples from which they originate and that sampling error is unlikely to represent an obstacle to biopsy-based transcriptomic profiling in uveal melanoma.

Supervised Analysis of Matched Mock Biopsy/Solid Tumor Samples

Figure 2:
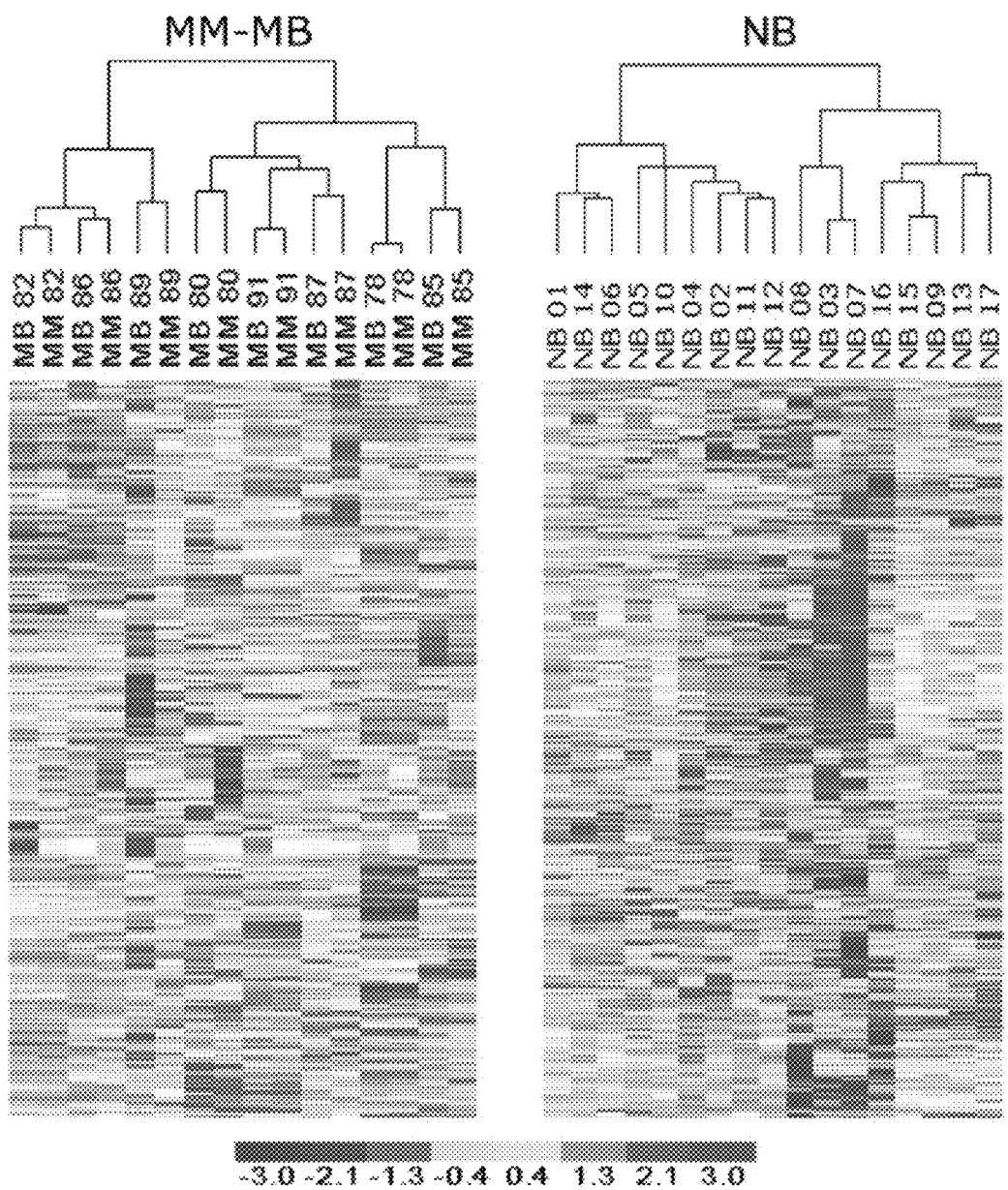
FIG. 2 depicts heat maps showing unsupervised hierarchical clustering of uveal malignant melanomas (MM), matching mock biopsy specimens (MB), and needle biopsy specimens (NB) using 806 probe sets filtered for a median significance P value <0.05 and gene expression variance >1.

Hierarchical clustering of the MM and MB samples also revealed a higher order of tumor aggregation into two groups of six and 10 specimens each (FIG. 2). Self-organizing maps, another unsupervised analytical technique, grouped the specimens into the same clusters. To determine whether the dichotomous clustering of MM-MB specimens may correspond to the prognostically validated class 1 and class 2 designations previously described in the OrigMM dataset (2), we compared the discriminating probe sets for the two datasets. For this analysis, we filtered the probe sets for a median significance P value<0.05 and included the top 5000 most variable probe sets. Discriminating probe sets were generated for both datasets using the Marker Selection algorithm of the GeneCluster2 software.(7) The distance function was prescribed by the signal-to-noise metric and the class estimate by median gene expression. The 400 top-ranked probe sets from each dataset were compared with each other for overlap. A highly significant overlap of 118 concordant probe sets was observed between the MM-MB and origMM lists (P<0.00001) (FIG. 3A). These findings suggest that the transcriptomic profiles obtained from the MM-MB dataset correspond to the prognostically significant tumor classes identified with the origMM dataset, and they demonstrate the feasibility of molecular prognostic testing in uveal melanoma based on fine needle aspirates.

Analysis of Needle Biopsy Samples

Needle biopsy (NB) specimens were obtained at two locations (nine from St. Louis and eight from San Francisco) and processed at the Washington University site. The 17 samples were normalized together using RMA and then filtered for median significance P value<0.05 and gene expression variance>1 across all specimens. Hierarchical clustering identified two tumor groups of eight and nine specimens (FIG. 2). The same dichotomous clustering was observed with self-organizing maps. These results were consistent with those obtained with the origMM, MM, and MB datasets, and they suggested that the NB specimens segregated into prognostically significant classes based on transcriptomic profile. To support this interpretation, we compared the discriminating gene list with those from the MM-MB and origMM datasets. As described above for the MM-MB dataset, we filtered the NB dataset for probe sets with median significance P value<0.05, included the top 5000 most variable probe sets, and performed Marker Selection using the signal-to-noise metric and the class estimate by median gene expression. The 400 top-ranked probe sets were then compared with the MM-MB and origMM datasets. There was a highly significant overlap of 100 concordant probe sets between the NB and MM-MB datasets and an even more significant overlap of 124 probe sets between the NB and origMM data-sets (for both comparisons, P<0.00001) (FIG. 3A). Importantly, epithelioid cytology was strongly associated with the class 2 molecular profile in the OrigMM and MM-MB datasets, where enucleation specimens were available for histopathological assessment (P<0.0001), but this association was less evident when cytology was assessed from biopsy specimens alone in the NB dataset (P=0.24). In fact, three cases where the biopsy sample was insufficient for accurate cytologic diagnosis (NB3, NB4, and NB16) nevertheless provided sufficient material for accurate molecular profiling. This ability to use extremely small amounts of tumor material highlights a potential advantage of molecular profiling.

Development of a Predictive Model

Figure 3:
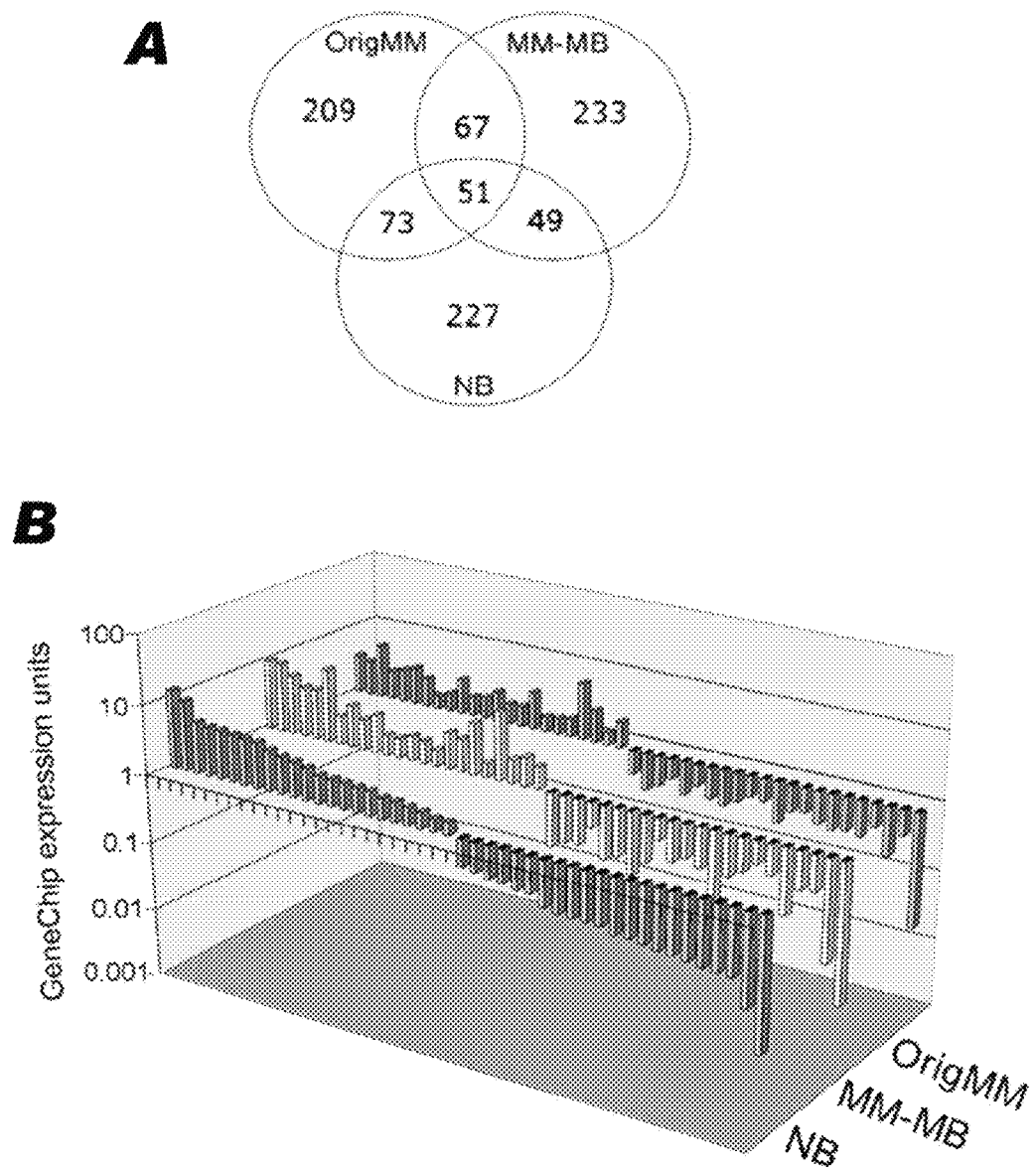
FIG. 3 depicts illustrations of the probe sets used in Example 1. A: Venn diagram showing concordant probe sets between the NB, MM-MB, and origMM datasets. B: Comparison of GenChip expression units for the 45-probe set list in the indicated datasets. C: Hierarchical clustering and (D) principal component analysis of the indicated datasets using the 45-probe-set list (blue spheres, class 1 tumors; red spheres, class 2 tumors). The two classes indicated in the Tschentscher dataset refer to monosomy versus disomy for chromosome 3.
Figure 3C:
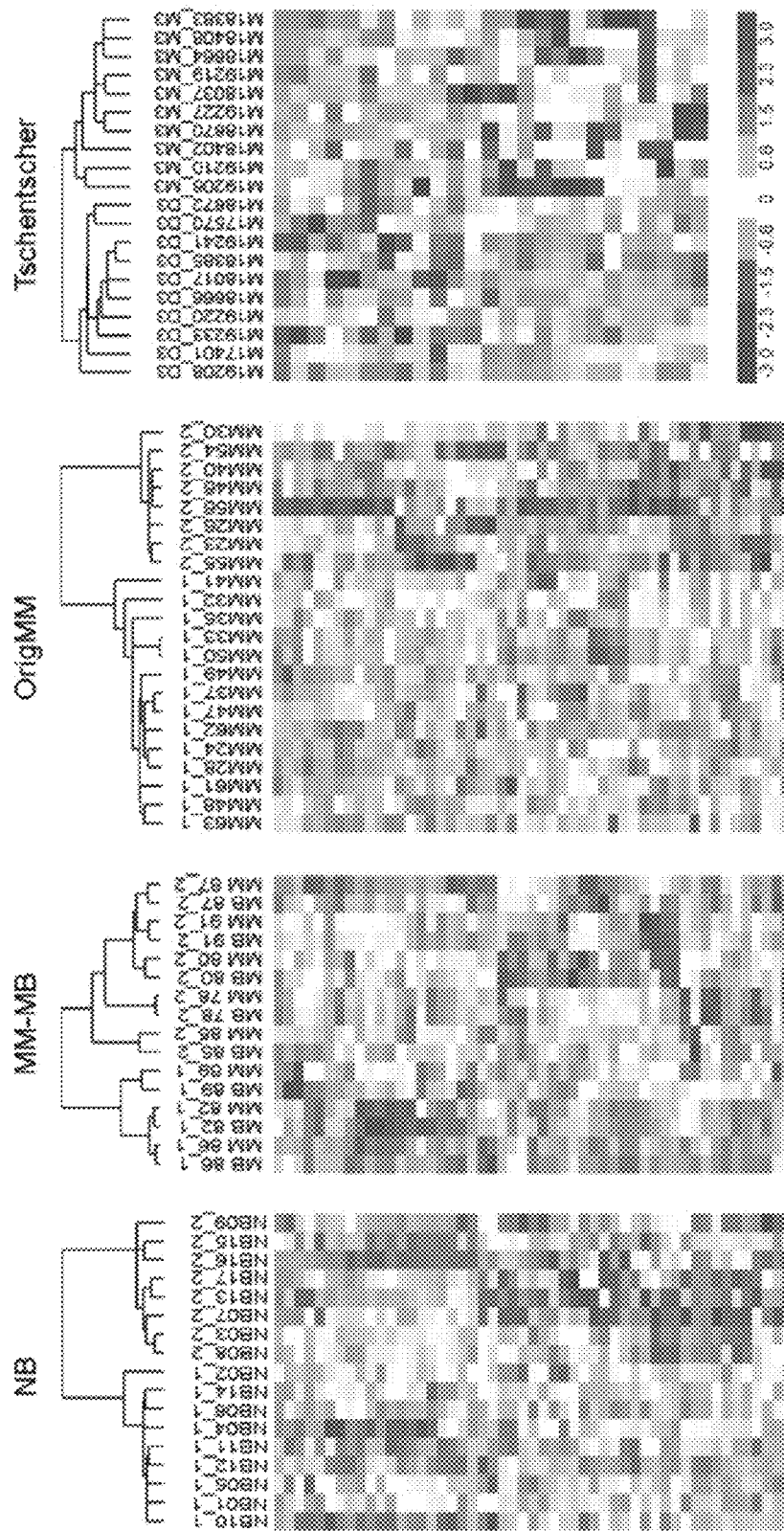
Figure 3D:
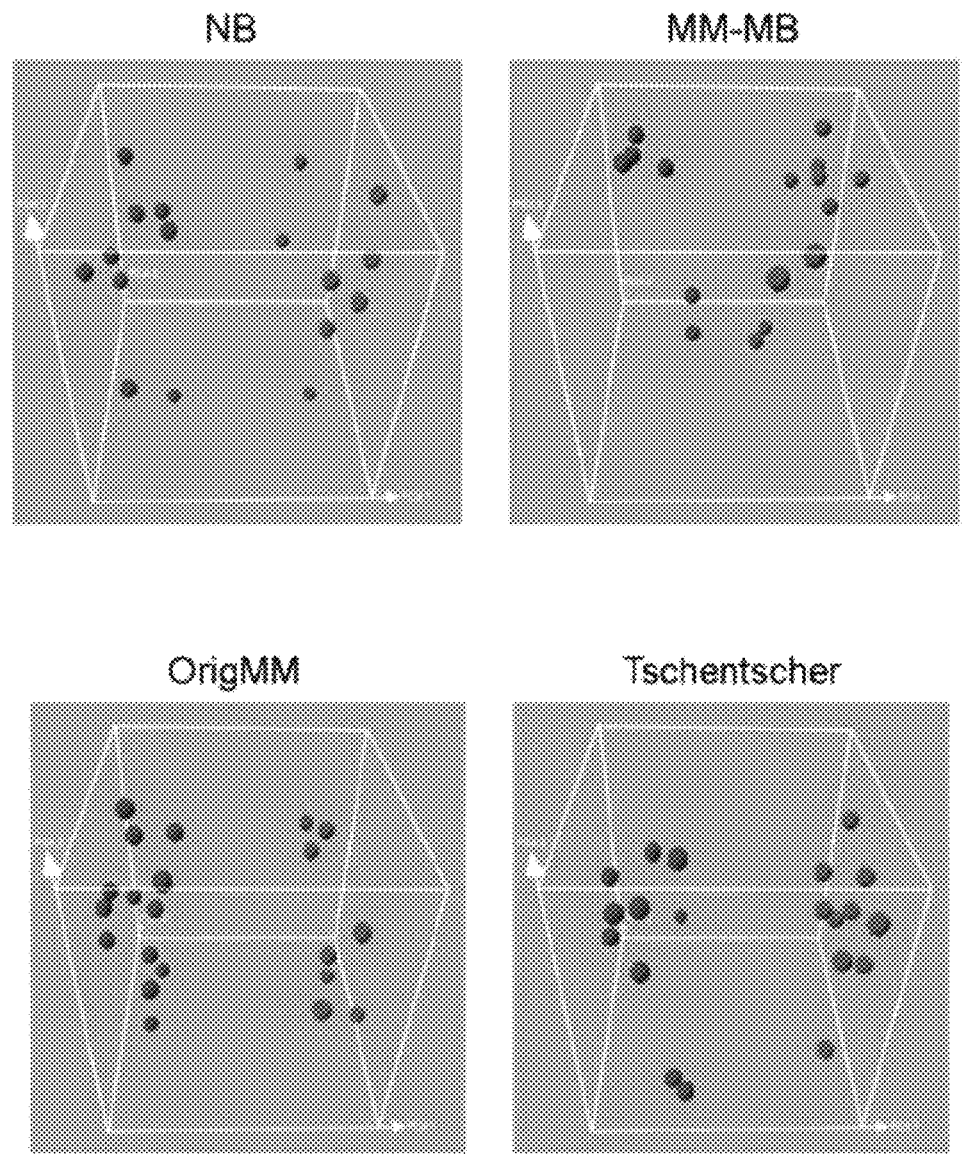

To identify a feature set (group of probe sets) that was sufficiently robust to classify individual tumors accurately from any of our datasets (OrigMM, MM-MB, and NB), we took the intersection of the three discriminating probe set lists, which resulted in 51 probe sets, which was further reduced to 45 probe sets after eliminating six that had a fold change<1.5 in one or more datasets (FIG. 3, A and B, and Table 2). All tumors from all three datasets were grouped correctly by hierarchical clustering and principal component analysis using only the information contained in the 45-probe set list (FIG. 3, C and D).

TABLE 2

| Gene Symbol | Gene Title | Up-regulated class | Fold change NB | Fold change MM-MB | Fold change OrigMM |
|---|---|---|---|---|---|
| HPGD | hydroxyprostaglandin dehydrogenase 15-(NAD) | class 1 | 13.17 | 9.84 | 3.56 |
| HPGD | hydroxyprostaglandin dehydrogenase 15-(NAD) | class 1 | 9.96 | 9.61 | 3.08 |
| CHL1 | cell adhesion molecule with homology to L1CAM (close homolog of L1) | class 1 | 5.41 | 7.11 | 5.68 |
| ALDH1L1 | aldehyde dehydrogenase 1 family, member L1 | class 1 | 5.05 | 5.18 | 2.59 |
| AZGP1 | alpha-2-glycoprotein 1, zinc | class 1 | 4.99 | 5.24 | 2.96 |
| ROBO1 | roundabout, axon guidance receptor, homolog 1 (*Drosophila*) | class 1 | 4.78 | 11.18 | 3.39 |
| — | *Homo sapiens*, clone IMAGE: 5538654, mRNA | class 1 | 4.59 | 2.51 | 2.64 |
| ZNF415 | zinc finger protein 415 | class 1 | 4.46 | 3.99 | 1.53 |
| SLC6A15 | solute carrier family 6, member 15 | class 1 | 3.83 | 2.70 | 1.85 |
| DCT | dopachrome tautomerase | class 1 | 3.39 | 3.43 | 3.26 |
| LMCD1 | LIM and cysteine-rich domains 1 | class 1 | 3.14 | 1.94 | 1.96 |
| FLJ20551 | hypothetical protein FLJ20551 | class 1 | 2.85 | 1.90 | 2.08 |
| RYR1 | ryanodine receptor 1 (skeletal) | class 1 | 2.43 | 2.24 | 2.78 |
| LPIN1 | lipin 1 | class 1 | 2.38 | 2.12 | 1.98 |
| LZTFL1 | leucine zipper transcription factor-like 1 | class 1 | 2.33 | 1.70 | 1.99 |
| ROPN1B | ropporin, rhophilin associated protein 1B | class 1 | 2.26 | 3.33 | 3.53 |
| HRASLS | HRAS-like suppressor | class 1 | 2.23 | 2.97 | 1.64 |
| DLC1 | deleted in liver cancer 1 | class 1 | 1.96 | 5.58 | 1.70 |
| CADPS2 | Ca2+-dependent activator protein for secretion 2 | class 1 | 1.95 | 1.60 | 1.84 |
| ENPP2 | ectonucleotide pyrophosphatase/phosphodiesterase 2 (autotaxin) | class 1 | 1.83 | 9.76 | 6.78 |
| SCRN1 | secernin 1 | class 1 | 1.71 | 2.18 | 2.95 |
| NFIB | Nuclear factor I/B | class 1 | 1.52 | 2.62 | 1.53 |
| MID1 | midline 1 (Opitz/BBB syndrome) | class 1 | 1.52 | 2.09 | 2.39 |
| HTR2B | 5-hydroxytryptamine (serotonin) receptor 2B | class 2 | 73.09 | 104.54 | 45.76 |
| RGS1 | regulator of G-protein signalling 1 | class 2 | 19.89 | 29.87 | 2.38 |
| IGSF4 | Immunoglobulin superfamily, member 4 | class 2 | 8.53 | 3.33 | 5.15 |
| DOCK10 | dedicator of cytokinesis 10 | class 2 | 8.30 | 3.45 | 2.25 |
| FAM70A | family with sequence similarity 70, member A | class 2 | 8.15 | 8.74 | 3.37 |
| CUGBP2 | CUG triplet repeat, RNA binding protein 2 | class 2 | 7.53 | 2.74 | 3.09 |
| CUGBP2 | CUG triplet repeat, RNA binding protein 2 | class 2 | 6.98 | 2.17 | 3.36 |
| C1QB | complement component 1, q subcomponent, beta polypeptide | class 2 | 6.88 | 3.07 | 2.98 |
| RAB31 | RAB31, member RAS oncogene family | class 2 | 6.38 | 4.03 | 2.28 |
| LYZ | lysozyme (renal amyloidosis) | class 2 | 6.07 | 12.10 | 2.45 |
| RAB31 | RAB31, member RAS oncogene family | class 2 | 6.04 | 3.82 | 3.90 |
| ME1 | malic enzyme 1, NADP(+)-dependent, cytosolic | class 2 | 5.26 | 3.02 | 2.10 |
| CXCR4 | chemokine (C-X-C motif) receptor 4 | class 2 | 5.13 | 3.82 | 2.02 |
| CUGBP2 | CUG triplet repeat, RNA binding protein 2 | class 2 | 5.10 | 2.10 | 2.61 |
| HLA-DQA1 | major histocompatibility complex, class II, DQ alpha 1 | class 2 | 5.00 | 4.92 | 3.25 |
| HLA-DPA1 | major histocompatibility complex, class II, DP alpha 1 | class 2 | 4.50 | 8.07 | 2.89 |
| FLJ20647 | hypothetical protein FLJ20647 | class 2 | 3.30 | 4.97 | 2.06 |
| RPS6KA2 | ribosomal protein S6 kinase, 90 kDa, polypeptide 2 | class 2 | 3.29 | 6.08 | 3.11 |
| PXDN | peroxidasin homolog (*Drosophila*) | class 2 | 3.02 | 2.40 | 2.01 |
| HTATIP2 | HIV-1 Tat interactive protein 2, 30 kDa | class 2 | 2.88 | 4.63 | 2.76 |
| PHLDA2 | pleckstrin homology-like domain, family A, member 2 | class 2 | 2.67 | 4.74 | 3.55 |
| KLF4 | Kruppel-like factor 4 (gut) | class 2 | 2.49 | 6.05 | 2.26 |

To validate further this feature set, we analyzed an independent dataset published by Tschentscher et al, in which an association was shown between transcriptomic profile and monosomy 3, a strong predictor of metastasis. (3) Using the Affymetrix "Best Match" file, we were able to identify matches for 25 of our 45 probe sets from this dataset, which was generated using the HG-U95Av2 chip. The expression data, which were presented as fold change, were normalized to mean=0 and unit variance. Unsupervised hierarchical clustering and principal component analysis using these 25 probe sets correctly grouped all tumors according to chromosome 3 status (FIG. 3, C and D). Thus, a small feature set can accurately classify a broad range of uveal melanomas from whole-tissue and biopsy specimens.

Figure 4A:
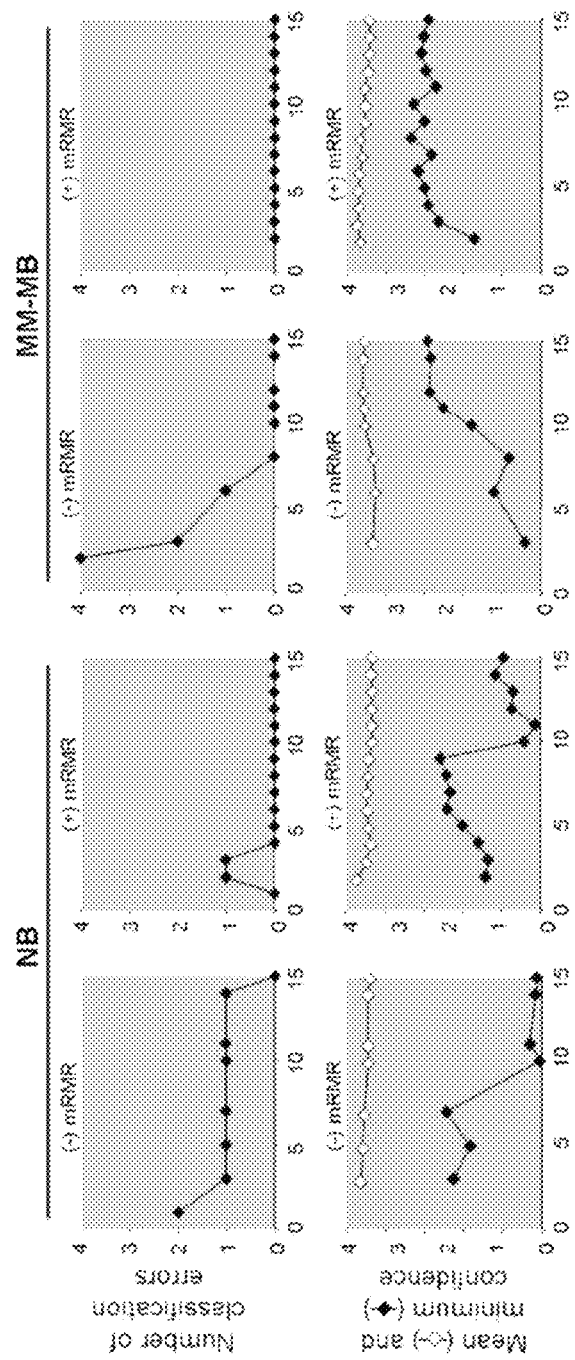
FIG. 4A depicts datasets NB and MM-MB.
Figure 4B:
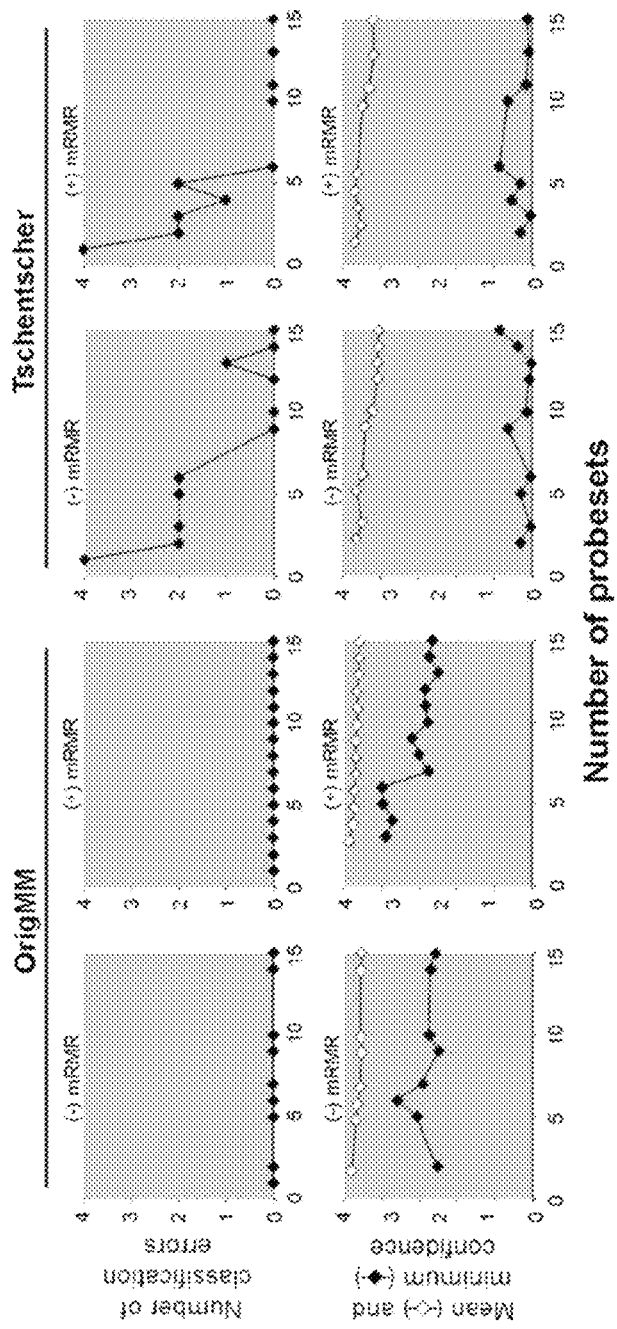
FIG. 4B depicts datasets OrigMM and Tschentscher. The predictive model was evaluated for class assignment by transcriptome signature in all datasets except the Tschentscher dataset, which was evaluated for monosomy 3. Probe sets were entered randomly (−mRMR) or by minimum redundancy and maximum relevance (+mRMR) into a weighted voting algorithm. Classification errors calculated by leave-one-out cross-validation are plotted on the upper graph. The mean and minimum confidence scores are plotted on the lower graph.

We then tested the performance of this feature set in a predictive model by entering the probe sets stepwise in a random fashion into a weighted voting algorithm and evaluating class assignment by leave-one-out cross-validation using GeneCluster software. The predictor correctly classified all tumors with 15 probe sets for the NB dataset, eight for the MM-MB dataset, one for the OrigMM dataset, and nine for the Tschentscher dataset (FIG. 4). The number of probe sets required for class assignment was reduced even further by ranking them for minimal redundancy and maximal relevance using the mRMR algorithm (10) and entering them stepwise into the predictor. Using this technique, all of the tumors were classified correctly with as few as one probe set for the NB dataset, two for the MM-MB dataset, one for the OrigMM dataset, and six for the Tschentscher dataset (FIG. 4).

Discussion

This study supports the feasibility of prognostic testing in uveal melanoma by transcriptomic profiling of fine needle biopsy specimens. These results show that RNA of sufficient quantity and quality can be obtained from fine needle ocular aspirates to generate microarray-based transcriptomic profiles that closely resemble those obtained from large tissue sections from the same tumor. Furthermore, it is shown that accurate molecular profiles can be obtained from extremely small biopsy samples that cannot be assessed confidently by cytologic examination alone. These studies also demonstrate that RNA from fine needle aspirates can be shipped safely to distant locations before processing, which would be required for large-scale clinical testing and multicenter trials.

This study also demonstrates effective strategies for reducing three sources of error in transcriptome-based machine learning and predictive testing: overfitting, redundancy, and instability of predictive feature sets. (10,11) The impact of overfitting (the degree to which a predictive model is representative of the tumors used to train the model but not of all tumors on which the predictor may be applied), can be reduced by applying the predictor to multiple independent datasets.(11) Hence, we have filtered and cross-validated our feature set and predictive model through four independent datasets (NB, MM-MB, OrigMM, and Tschentscher). Classification accuracy can also be affected adversely by feature set redundancy (the tendency for multiple genes in a feature set to provide overlapping predictive information), which can be addressed using algorithms such as mRMR to eliminate redundant features and to retain those with maximal predictive power.(10) In each of our four datasets, mRMR allowed us to reduce substantially the number of probe sets in the predictive model without sacrificing accuracy.

References for Example 1

1. Harbour J W: Clinical overview of uveal melanoma: introduction to tumors of the eye. Ocular Oncology. Edited by D M Albert, A Polans. New York, Marcel Dekker, 2003, pp 1-18
2. Onken M D, Worley L A, Ehlers J P, Harbour J W: Gene expression profiling in uveal melanoma reveals two molecular classes and predicts metastatic death. Cancer Res 2004, 64:7205-7209
3. Tschentscher F, Husing J, Holter T, Kruse E, Dresen I G, Jockel K H, Anastassiou G, Schilling H, Bornfeld N, Horsthemke B, Lohmann D R, Zeschnigk M: Tumor classification based on gene expression profiling shows that uveal melanomas with and without monosomy 3 represent two distinct entities. Cancer Res 2003, 63:2578-2584
4. Onken M D, Lin A Y, Worley L A, Folberg R, Harbour J W: Association between microarray gene expression signature and extravascular matrix patterns in primary uveal melanomas. Am J Ophthalmol 2005, 140:748-749
5. Onken M D, Ehlers J P, Worley L A, Makita J, Yokota Y, Harbour J W: Functional gene expression analysis uncovers phenotypic switch in aggressive uveal melanomas. Cancer Res 2006, 66:4602-4609
6. Faulkner-Jones B E, Foster W J, Harbour J W, Smith M E, Davila R M: Fine needle aspiration biopsy with adjunct immunohistochemistry in intraocular tumor management. Acta Cytol 2005, 49:297-308
7. Golub T R, Slonim D K, Tamayo P, Huard C, Gaasenbeek M, Mesirov J P, Coller H, Loh M L, Downing J R, Caligiuri M A, Bloomfield C D, Lander E S: Molecular classification of cancer: class discovery and class prediction by gene expression monitoring. Science 1999, 286:531-537
8. Wackerly D, Mendenhall W, Scheaffer R L: Mathematical Statistics with Applications. Belmont, C A, Duxbury Press, 1996, 107 p
9. Char D H, Kroll S M, Stoloff A, Kaleta-Michaels S, Crawford J B, Miller T R, Howes Jr E L, Ljung B M: Cytomorphometry of uveal melanoma. Comparison of fine needle aspiration biopsy samples with histologic sections. Anal Quant Cytol Histol 1991, 13:293-299
10. Peng H, Long F, Ding C: Feature selection based on mutual information: criteria of max-dependency, max-relevance, and minredundancy. IEEE Trans Pattern Anal Mach Intell 2005, 27:1226-1238
11. Pusztai L, Hess K R: Clinical trial design for microarray predictive marker discovery and assessment. Ann Oncol 2004, 15:1731-1737
12. Sima C, Braga-Neto U, Dougherty E R: Superior feature-set ranking for small samples using bolstered error estimation. Bioinformatics 2005, 21:1046-1054

Example 2

Transcriptomic Versus Chromosomal Prognostic Risk Analysis

In recent years, there has been increasing interest in individualize management of cancer patients based on predictive molecular testing (1,2). Uveal (ocular) melanoma represents an ideal cancer for applying the strategy. Uveal melanoma is the most common primary cancer of the eye and has a strong predilection for hematogenous metastasis, particularly to the liver (3). Investigators have searched for clinical and pathologic prognostic factors for over a century and have identified several that are statistically associated with metastasis, including advanced patient age, anterior tumor location, increased tumor size, epithelioid cell type, and local tumor invasion through the sclera. However, predictive accuracy of these factors has not been adequate for making individualized clinical decisions, such as whether a given patient is at sufficiently high risk for metastasis to necessitate more intense and frequent metastatic surveillance or whether prophylactic systemic therapy may be appropriate. More recently, investigators have identified genetic alterations, such as monosomy 3, which are significantly associated with metastasis (4-6). With the development of more precise techniques for detecting chromosomal alterations, such as spectral karyotyping, fluorescence in situ hybridization (FISH), and comparative genomic hybridization (CGH), monosomy 3 has shown predictive accuracy superior to previous clinical and pathologic features (7-11).

Consequently, detection of monosomy 3 has now been adopted by most centers around the world as the gold standard for metastatic prediction in uveal melanoma (11-14). Indeed, prospective clinical trials are in the planning stages around the world that intend to use monosomy 3 as an entry criterion for preemptive antimetastatic interventions in high-risk uveal melanoma patients. However, the sensitivity and specificity of monosomy 3, essential indicators of its utility as a clinical marker of metastatic risk, have not been reported, and it is possible that other available molecular classifiers may be superior to monosomy 3 for individualized patient management.

A molecular classification of uveal melanomas based on gene expression profile has recently been reported that strongly predicts metastasis (15,16). Tumors with the class 1 gene expression signature have a low risk of metastasis, and those with the class 2 signature have a high risk of metastasis (15). The initial study was done on tumor tissue obtained after eye removal, but it has also been shown that gene expression profiling can be done accurately on fine-needle biopsy specimens obtained before radiotherapy in uveal melanoma patients who do not require eye removal (17). Although these initial studies showed a strong association between the class 2 signature and monosomy 3, the former seemed to be superior in prognostic accuracy (15).

In this study of 67 uveal melanoma patients, the largest outcome study of its kind to date in uveal melanoma, the prognostic accuracy of the gene expression-based classifier is compared to monosomy 3 detected by FISH and CGH.

Preparation of RNA and DNA.

This study was approved by the Human Studies Committee at Washington University (St. Louis, Mo.), and informed consent was obtained from each subject. Tumor tissue was obtained immediately after eye removal, snap frozen, and prepared for RNA and DNA analysis as described previously (15). Genomic DNA was prepared using the Wizard Genomic DNA Purification kit (Promega, Madison, Wis.). RNA was isolated using PicoPure kits (Arcturus, Sunnyvale, Calif.). Complementary DNA was generated from total RNA by reverse transcription, linear amplification, and in vitro transcription to generate biotinylated cRNA targets that were hybridized to Affymetrix Hu133A and Av2 GeneChips according to the manufacturer's protocols with the assistance of the Siteman Cancer Center GeneChip Facility. Alternatively, some RNA samples were hybridized to Illumina Human Ref8 BeadChip arrays with the assistance of the Microarray Facility of the Washington University Genome Sequencing Center.

Microarray Expression Profiling.

Microarray gene expression values were obtained on Affymetrix U133A, U133Av2, and Illumina Ref8 chips. Analysis of Affymetrix data was described previously (15, 17, 18). Illumina data were normalized by the rank invariant method using BeadStation software (www.illumina.com), log 2 transformed, and analyzed by principal component analysis using Spotfire software (www.spotfire.com). Assignment of tumors to class 1 and class 2 was done by a weighted voting algorithm using GeneCluster2 software (www.broad.mit.edu/cancer/software) as described previously (15, 17).

Fluorescence In Situ Hybridization.

Dual-color FISH was done as described previously (19). Briefly, paraffin-embedded tissue sections were deparaffinized with Citrisolv (Fisher Scientific, Pittsburgh, Pa.), dehydrated in 100% ethanol, subjected to target retrieval by steam heating in citrate buffer (pH 6.0) for 20 min, digested in pepsin solution (4 mg/mL in 0.9% NaCl) for 20 min at 37° C., rinsed in 2×SSC (300 mmol/L sodium chloride and 30 mmol/L sodium citrate) at room temperature for 5 min, and air dried. A Spectrum Green-labeled chromosome 7 centromeric DNA probe, CEP7(D7Z1) (Vysis, Inc., Downers Grove, Ill.), was paired with a Spectrum Orange-labeled chromosome 3 centromeric probe, CEP3(D3Z1) (Vysis). Probes were diluted 1:50 in t-DenHyb buffer (Insitus Laboratories, Albuquerque, N. Mex.). Hybridization mix was applied to sections followed by denaturation in a 90° C. slide moat (Boekel Scientific, Feasterville, Pa.) for 13 min. Hybridization was done overnight at 37° C. in a humidified chamber. Slides were then washed in 50% formamide/1× SSC for 5 min and then twice in 2×SSC for 10 min each at room temperature. Slides were allowed to air dry, and then, nuclei were counterstained with 4,6-diamidino-2-phenylindole (Insitus Laboratories). Sections were visualized on an Olympus BX60 fluorescent microscope (Olympus, Melville, N.Y.). At least 100 nuclei were analyzed for each tumor. A threshold of 30% nuclei with one chromosome 3 signal and two chromosome 7 signals was established for making the call of monosomy 3.

Array CGH.

Array CGH (aCGH) was done using human bacterial artificial chromosome arrays. Previously published samples were analyzed by the Microarray Shared Resource at the Comprehensive Cancer Center, University of California (San Francisco, Calif.) using a microarray-based platform containing a genome-wide collection of genomic contigs as described previously (15, 20). Newer, previously unpublished samples were analyzed by the Microarray and Genomics Facility of the Roswell Park Cancer Institute (Buffalo, N.Y.) using an array platform containing ~6,000 bacterial artificial chromosome clones (microarrays.roswellpark.org). One microgram of reference and test sample genomic DNA were individually fluorescently labeled using the BioArray CGH Labeling System (Enzo Life Sciences, Farmingdale, N.Y.). DNA was hybridized to the arrays for 16 h at 55° C. using a GeneTAC hybridization station (Genomic Solutions, Inc., Ann Arbor, Mich.). The hybridized aCGH slides were then scanned using a GenePix 4200A Scanner (Molecular Devices, Sunnyvale, Calif.) to generate high-resolution (5 μm) images for both Cy3 (test) and Cy5 (control) channels. Image analysis was done using the ImaGene (version 6.0.1) software from BioDiscovery, Inc. (El Segundo, Calif.). A loess-corrected log 2 ratio of the background-subtracted test/control was calculated for each clone to compensate for nonlinear raw aCGH profiles in each sample. A log 2 average raw ratio of >0.5 was used as the threshold for significant DNA copy number deviations.

Statistical Analysis.

Fisher's exact test was used to assess the significance of association between two categorical variables. Cox univariate proportional hazards was used to assess time-dependent association with metastasis for categorical and continuous variables. Kaplan-Meier analysis was used to assess time-dependent association with metastasis for categorical variables. Continuous variables were dichotomously categorized by the value that maximized sensitivity and specificity by receiver operating characteristics analysis. Variables that exhibited a significant association with metastasis were further analyzed by Cox multivariate proportional hazards modeling to assess their relative contribution to metastasis. Sensitivity, specificity, likelihood ratios, and predictive values were assessed for all clinical, pathologic, and molecular factors. In analysis A, metastasis was used as the end point. In analysis B, class 2 gene expression profile was used as a surrogate end point in metastasis-free patients. All statistical analyses were done using MedCalc software version 9.0.0.1.

Results

Figure 5A:
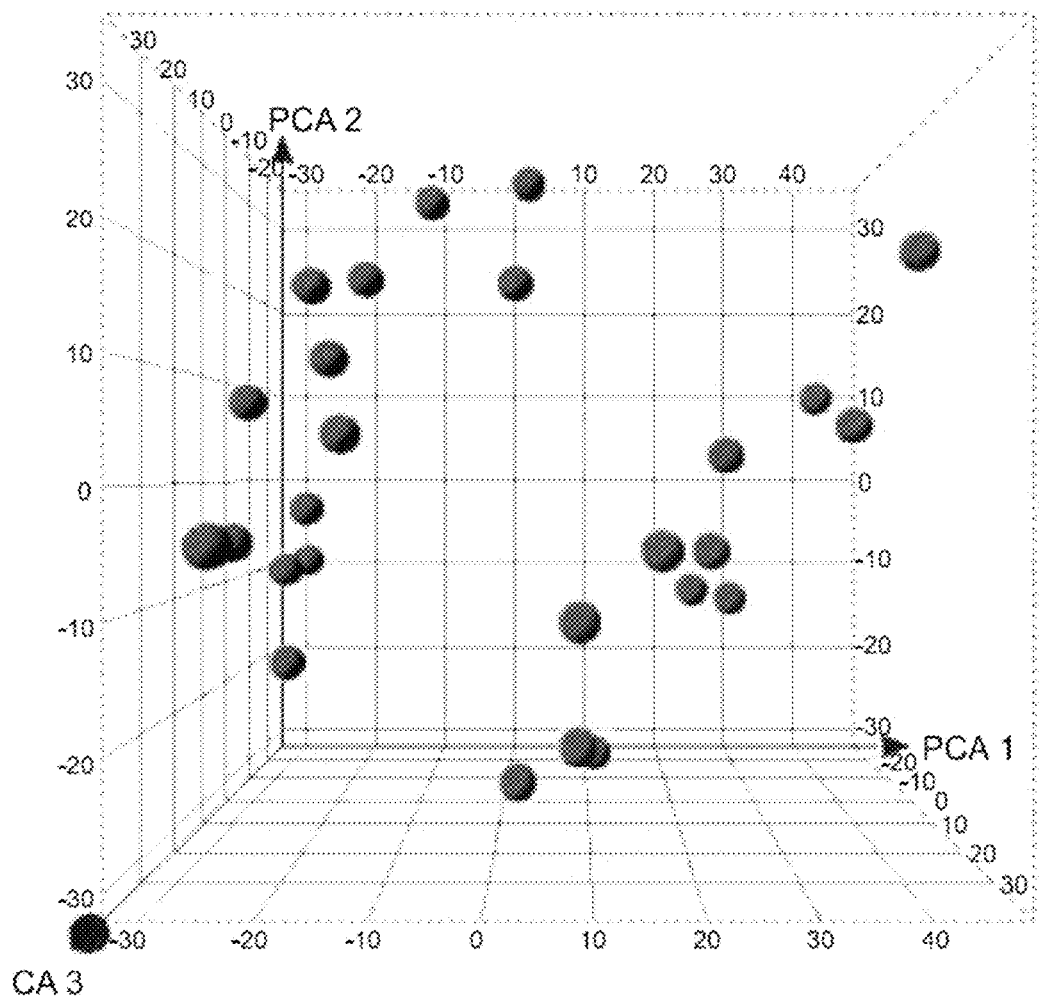
FIG. 5 depicts a series of graphs showing gene expression profiling of 26 uveal melanomas using the Illumina Human Ref8 platform. A: gene expression profiles of 26 primary uveal melanomas (spheres) displayed in three-dimensional space by principal component analysis to show the clustering of tumors into class 1 (blue) and class 2 (red) tumors. B: performance of a weighting voting classifier using 4-fold cross-validation. Percentage classification errors are a function of the number of features (genes) in the predictor. Maximum accuracy was achieved with seven genes. C: mean RNA expression of the seven genes in the weighted voting predictor in 14 class 1 tumors and 12 class 2 tumors.
Figure 5:
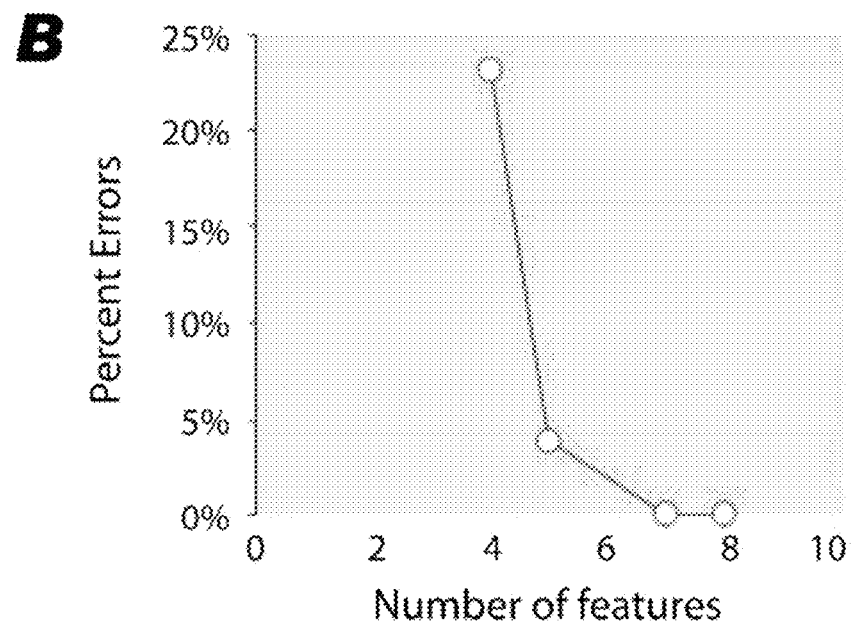
Figure 5:
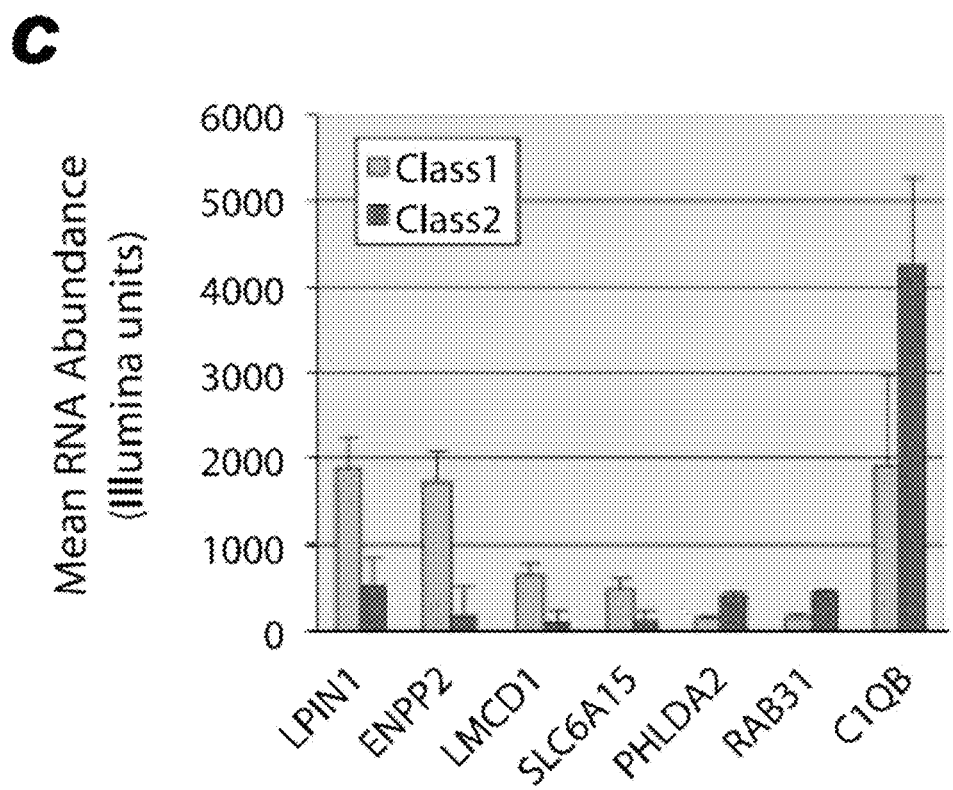
Figure 6A:
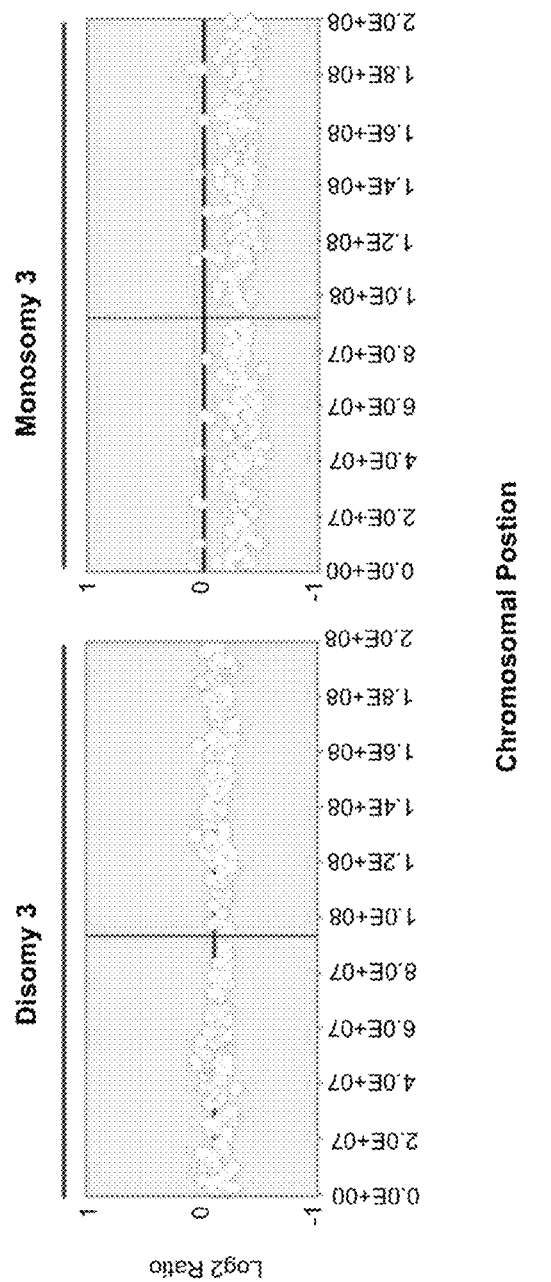
FIG. 6 depicts a series of graphs and photographs showing assays for detecting monosomy 3. A: representative examples of tumors analyzed by aCGH exhibiting disomy 3 and monosomy 3. X axis, distribution of chromosome 3 fragments (represented in bacterial artificial chromosomes) distributed along the chromosome; Y axis, relative proportion of tumor DNA compared with normal control DNA, expressed as the log 2 ratio, where 0 indicates [tumor DNA]=[normal DNA], a negative value indicates [tumor DNA]<[normal DNA], and a positive value indicates [tumor DNA]>[normal DNA]. Normal DNA was derived from peripheral blood lymphocytes from the same patient. B: left, summary of FISH results. The graph plots the percentage of nuclei exhibiting one chromosome 3 signal (red) and two chromosome 7 signals (green). The 30% threshold for monosomy 3 is indicated. right, representative photomicrographs of FISH analysis in disomy 3 and monosomy 3 tumors. Note that some tumor nuclei in the monosomy 3 tumor exhibit two red signals (arrow), indicating heterogeneity for monosomy 3.

The study included 67 uveal melanoma patients treated by enucleation. Table 3 summarizes the clinical and pathologic features. Gene expression profiling was done on 52 tumors, including 26 analyzed with the Affymetrix GeneChip array, 16 with the Illumina Ref8 BeadChip array, and 10 with both platforms. Tumors analyzed on the Affymetrix platform were previously assigned to class 1 or class 2 (15, 17). In a similar manner, the 26 tumors analyzed on the Illumina platform were assigned to one of the two classes (FIG. 5A). Using a weighted voting predictive algorithm and 4-fold cross-validation, accurate class assignment was achieved with as few as 7 genes from a 40-gene signature that we previously validated on four independent data sets (FIG. 5B and C). Altogether, 27 tumors were assigned to class 1 and 25 tumors were assigned to class 2. In the 10 tumors analyzed by both the Affymetrix and Illumina platforms, there was 100% agreement in class assignments between the two platforms (P=0.004, Fisher's exact test). Chromosome 3 status was assessed by FISH and aCGH. Monosomy 3 was detected in 21 of 49 (43%) tumors by aCGH and in 13 of 36 (36%) tumors by FISH (FIG. 6). The gene expression classifier results were significantly associated with monosomy 3 by both aCGH (P=4.1×10$^{-6}$, Fisher's exact test) and FISH (P=0.009).

TABLE 3

| Clinicopathologic factors (N = 67 patients) | | |
|---|---|---|
| Age at diagnosis, mean (range) | | 60.6 (24-87) |
| Gender, n (%) | Male | 44 (66) |
| | Female | 23 (34) |
| Eye, n (%) | Right | 36 (54) |
| | Left | 31 (46) |
| Tumor location, n (%) | Posterior | 40 (59) |
| | Anterior | 27 (41) |
| Largest tumor diameter (mm), mean (range) | | 17.4 (5.4-24) |
| Tumor thickness (mm), mean (range) | | 9.7 (2.2-22) |
| Histopathologic cell type, n (%) | Spindle | 23 (34) |
| | Mixed | 21 (31) |
| | Epithelioid | 23 (34) |
| Histopathologic local invasion, n (%) | None | 31 (46) |
| | Intrascleral | 19 (28) |
| | Extrascleral | 17 (25) |
| | Metastasis | 18 (27) |
| Months from diagnosis to end point, mean (range) | | 28.4 (1-90) |

By Cox univariate proportional hazards, class 2 gene expression profile (P=0.0001), advanced patient age (P=0.01), and scleral invasion (P=0.007) were significantly associated with metastasis (Table 4). By Cox univariate proportional hazards, monosomy 3 (aCGH), monosomy 3 (FISH), histopathologic cell type, tumor thickness, gender, largest tumor diameter, and anterior tumor location were not significantly associated with metastasis. Kaplan-Meier analysis rendered similar results. When all three significant variables were entered into a Cox multivariate model, only class 2 gene expression profile exhibited significant association with metastasis.

TABLE 4

| | Cox univariate | Cox multivariate | Kaplan-Meier |
|---|---|---|---|
| Class 2 gene expression profile | 0.0001 | 0.0449 | 0.0001 |
| Monosomy 3 (aCGH) | 0.0762 | — | 0.0856 |
| Monosomy 3 (FISH) | 0.1275 | — | 0.1482 |
| Age | 0.0144 | 0.4703 | 0.007 |
| Scleral invasion | 0.0071 | 0.2372 | 0.0119 |
| Histopathologic cell type | 0.2802 | — | 0.1126 |
| Tumor thickness | 0.1085 | — | 0.1096 |
| Gender | 0.4184 | — | 0.4086 |
| Largest tumor diameter | 0.5867 | — | 0.5899 |
| Anterior tumor location | 0.4939 | — | 0.5018 |

Sensitivity, specificity, likelihood ratios, and predictive values were calculated for each clinical, pathologic, and molecular prognostic factor (Table 5). In analysis A, the metastasis group consisted of all 18 patients who had developed metastasis, and the nonmetastasis group contained all 16 patients without metastasis who had at least 3-year follow-up after ocular tumor treatment. The class 2 gene expression profile outperformed all other prognostic variables, with 84.6% sensitivity and 92.9% specificity (Table 6). Similar results were obtained when the nonmetastasis group was limited to metastasis-free patients with at least 4-year follow-up. The other predictive indices for gene expression profiling were also greatly superior to those for other clinical, pathologic, and molecular features, with positive and negative predictive values of 91.7% and 86.7%, respectively, and positive and negative likelihood ratios of 11.9 and 0.2, respectively.

TABLE 5

| MM# | Age at ocular diag. | M/F | Eye | Tumor location | Largest tumor diameter (mm) | Tumor thick. (mm) | Path. cell type | Scleral Invasion | Months to end-point | Metast. | Gene exp. profile | Chr 3 status (aCGH) | Chr 3 status (FISH) |
|---|---|---|---|---|---|---|---|---|---|---|---|---|---|
| 6 | 44 | M | Right | Posterior | 19 | 12.2 | Mixed | None | 81.0 | No | ND | ND | Disomy |
| 10 | 41 | M | Right | Posterior | 17 | 10.0 | Mixed | None | 89.7 | No | Class 1 | Disomy | ND |
| 13 | 75 | M | Right | Anterior | 18 | 11.0 | Mixed | Intrascleral | 26.2 | Yes | ND | Monosomy | ND |
| 16 | 24 | F | Left | Posterior | 24 | 12.6 | Spindle | Intrascleral | 59.6 | No | ND | Disomy | ND |
| 18 | 55 | M | Left | Posterior | 12 | 9.2 | Epithelioid | None | 67.4 | No | Class 1 | Disomy | ND |
| 23 | 74 | M | Right | Posterior | 20 | 11.0 | Spindle | None | 22.1 | Yes | Class 2 | ND | Monosomy |
| 24 | 63 | F | Right | Posterior | 20 | 12.0 | Spindle | None | 68.1 | No | Class 1 | ND | Disomy |
| 26 | 67 | F | Right | Posterior | 18 | 16.4 | Mixed | None | 45.2 | Yes | Class 2 | ND | ND |
| 27 | 77 | F | Right | Anterior | 14 | 7.0 | Epithelioid | Extrascleral | 14.1 | Yes | Class 2 | Disomy | ND |
| 28 | 47 | M | Left | Anterior | 20 | 12.2 | Epithelioid | None | 66.3 | No | Class 1 | Disomy | Disomy |
| 30 | 74 | M | Left | Anterior | 20 | 7.7 | Spindle | Extrascleral | 27.5 | Yes | Class 2 | ND | ND |
| 31 | 69 | F | Left | Posterior | 19 | 3.1 | Epithelioid | None | 7.0 | No | ND | Disomy | Disomy |
| 32 | 63 | F | Right | Posterior | 22 | 10.9 | Spindle | None | 66.2 | No | Class 1 | Disomy | Disomy |
| 33 | 30 | M | Left | Anterior | 22 | 4.6 | Spindle | Extrascleral | 31.9 | No | Class 1 | Disomy | Disomy |
| 35 | 74 | M | Left | Anterior | 14 | 11.9 | Spindle | Intrascleral | 59.6 | No | Class 1 | Disomy | Monosomy |
| 37 | 25 | F | Left | Anterior | 20 | 15.0 | Spindle | Intrascleral | 56.5 | No | Class 1 | Disomy | Monosomy |
| 38 | 87 | M | Left | Posterior | 15 | 6.4 | Epithelioid | Intrascleral | 33.7 | Yes | Class 1 | Disomy | Disomy |
| 39 | 29 | M | Right | Posterior | 12 | 6.3 | Spindle | None | 32.8 | No | ND | ND | Disomy |
| 40 | 76 | M | Left | Posterior | 24 | 12.0 | Mixed | None | 13.5 | Yes | Class 2 | ND | Monosomy |
| 41 | 75 | M | Right | Posterior | 12.39 | 13.0 | Mixed | None | 54.8 | No | Class 1 | Monosomy | Monosomy |
| 46 | 69 | F | Left | Posterior | 22 | 9.0 | Epithelioid | Intrascleral | 31.8 | Yes | Class 2 | Monosomy | Monosomy |
| 47 | 41 | M | Right | Anterior | 9.5 | 8.0 | Spindle | None | 31.6 | No | Class 1 | ND | ND |
| 48 | 50 | M | Left | Anterior | 24 | 9.0 | Spindle | Intrascleral | 49.7 | No | Class 1 | Disomy | Disomy |
| 49 | 65 | F | Right | Posterior | 20 | 12.0 | Spindle | None | 50.1 | No | Class 1 | Disomy | Disomy |
| 50 | 50 | F | Right | Posterior | 18.9 | 8.9 | Epithelioid | None | 26.0 | No | Class 1 | ND | Disomy |
| 51 | 62 | F | Right | Posterior | 16 | 6.6 | Mixed | Intrascleral | 27.7 | No | Class 2 | Monosomy | Disomy |
| 52 | 84 | M | Right | Anterior | NA | NA | Mixed | Extrascleral | 43.3 | Yes | ND | ND | ND |

TABLE 5-continued

| MM# | Age at ocular diag. | M/F | Eye | Tumor location | Largest tumor diameter (mm) | Tumor thick. (mm) | Path. cell type | Scleral Invasion | Months to end-point | Metast. | Gene exp. profile | Chr 3 status (aCGH) | Chr 3 status (FISH) |
|---|---|---|---|---|---|---|---|---|---|---|---|---|---|
| 53 | 47 | F | Right | Anterior | 15 | 7.8 | Mixed | Intrascleral | 10.1 | No | Class 1 | Disomy | ND |
| 54 | 80 | F | Right | Anterior | 15 | 6.7 | Mixed | Extrascleral | 34.6 | Yes | Class 2 | Monosomy | Monosomy |
| 55 | 82 | F | Right | Posterior | 19 | 8.6 | Epithelioid | Extrascleral | 46.0 | No | Class 2 | Monosomy | Monosomy |
| 56 | 63 | M | Left | Posterior | 18 | 11.7 | Mixed | None | 16.3 | No | Class 2 | Monosomy | ND |
| 57 | 53 | M | Left | Posterior | 22 | 11.6 | Epithelioid | Intrascleral | 39.6 | No | Class 1 | Disomy | ND |
| 60 | 67 | M | Left | Posterior | 14 | 9.5 | Epithelioid | None | 37.4 | Yes | Class 2 | Monosomy | Disomy |
| 61 | 67 | M | Left | Posterior | 11 | 4.2 | Mixed | Intrascleral | 36.8 | No | Class 1 | Disomy | Disomy |
| 62 | 70 | M | Right | Posterior | 18 | 7.2 | Spindle | None | 7.3 | No | Class 1 | ND | ND |
| 63 | 42 | M | Right | Posterior | 16 | 15.9 | Spindle | None | 39.5 | No | Class 1 | Disomy | ND |
| 64 | 62 | F | Right | Posterior | 18 | 6.1 | Spindle | Intrascleral | 11.4 | No | Class 1 | Monosomy | Disomy |
| 65 | 45 | F | Right | Anterior | 24 | 6.9 | Spindle | Intrascleral | 31.5 | Yes | ND | Disomy | ND |
| 66 | 47 | M | Right | Posterior | 22 | 9.2 | Mixed | Intrascleral | 33.6 | No | Class 2 | Monosomy | ND |
| 68 | 54 | M | Right | Posterior | 15 | 6.7 | Spindle | None | 0.0 | No | Class 1 | ND | ND |
| 70 | 62 | M | Left | Posterior | 24 | 15.6 | Epithelioid | Extrascleral | 27.4 | Yes | Class 2 | Monosomy | Disomy |
| 71 | 63 | F | Left | Posterior | NA | 12.5 | Spindle | Intrascleral | 0.6 | No | Class 2 | Monosomy | Monosomy |
| 72 | 48 | M | Left | Anterior | 20 | 15.0 | Spindle | Intrascleral | 5.8 | No | Class 2 | Disomy | Disomy |
| 74 | 77 | M | Right | Posterior | NA | 22.0 | Mixed | Intrascleral | 24.4 | No | Class 1 | Disomy | Disomy |
| 75 | 76 | F | Left | Posterior | 8 | 5.3 | Mixed | None | 24.3 | No | ND | ND | ND |
| 76 | 62 | M | Left | Posterior | 16 | 7.3 | Epithelioid | Extrascleral | 22.2 | Yes | Class 2 | Monosomy | ND |
| 77 | 51 | M | Right | Posterior | 24 | 7.9 | Mixed | None | 25.0 | No | ND | Disomy | ND |
| 78 | 67 | M | Left | Anterior | 21 | 10.5 | Epithelioid | None | 21.4 | No | Class 2 | Monosomy | Monosomy |
| 79 | 70 | M | Left | Anterior | 7 | 2.2 | Mixed | None | 15.8 | No | Class 2 | Monosomy | ND |
| 80 | 37 | M | Left | Anterior | NA | 11.3 | Epithelioid | Extrascleral | 21.3 | No | Class 2 | Monosomy | ND |
| 81 | 65 | M | Left | Anterior | 18.9 | 11.3 | Epithelioid | Extrascleral | 2.0 | Yes | Class 2 | Disomy | Disomy |
| 82 | 63 | F | Right | Posterior | 10 | 5.2 | Mixed | Intrascleral | 11.6 | No | Class 1 | Disomy | ND |
| 83 | 43 | M | Right | Anterior | 5.4 | 3.7 | Epithelioid | Extrascleral | 11.4 | No | Class 2 | Monosomy | ND |
| 85 | 67 | M | Right | Anterior | 21 | 13.4 | Epithelioid | Extrascleral | 13.1 | No | Class 1 | Monosomy | Disomy |
| 86 | 47 | M | Right | Posterior | 13.76 | 14.0 | Spindle | None | 8.4 | No | Class 1 | Disomy | ND |
| 87 | 53 | F | Left | Posterior | 16 | 5.9 | Epithelioid | Extrascleral | 13.7 | Yes | Class 2 | Monosomy | Monosomy |
| 88 | 60 | M | Left | Anterior | 16 | 10.6 | Epithelioid | None | 9.7 | No | Class 2 | Monosomy | Monosomy |
| 89 | 74 | M | Right | Anterior | 18 | 8.1 | Spindle | Extrascleral | 8.1 | Yes | Class 1 | Disomy | ND |
| 90 | 72 | F | Right | Posterior | 19 | 14.0 | Mixed | Extrascleral | 9.5 | No | Class 2 | Monosomy | ND |
| 91 | 64 | M | Right | Anterior | 17 | 10.2 | Mixed | None | 7.2 | No | Class 2 | Disomy | Disomy |
| 92 | 61 | M | Right | Anterior | 20 | 13.4 | Epithelioid | Intrascleral | 8.0 | No | Class 1 | Disomy | ND |
| 93 | 57 | M | Left | Anterior | 17 | 10.5 | Epithelioid | Extrascleral | 1.1 | No | Class 2 | Monosomy | Monosomy |
| 94 | 63 | M | Left | Posterior | 18 | 9.7 | Spindle | None | 1.3 | No | Class 1 | Disomy | ND |
| 97 | 79 | F | Right | Posterior | 22.2 | 11.2 | Epithelioid | None | 1.4 | No | ND | ND | Monosomy |
| 98 | 74 | F | Right | Anterior | 18 | 5.5 | Epithelioid | Extrascleral | 2.9 | No | ND | ND | ND |
| 100 | 68 | M | Right | Anterior | 18.4 | 12.3 | Epithelioid | None | 1.3 | No | ND | ND | ND |
| 101 | 66 | F | Left | Posterior | 15 | 6.4 | Spindle | None | 1.4 | No | ND | ND | ND |
| Y | 64 | M | Left | Posterior | 8 | 3.1 | Mixed | None | 42.4 | Yes | ND | ND | Disomy |

ND = not done
NA = not applicable

TABLE 6

| Prognostic factor | Sensitivity | Specificity | Positive likelihood ratio | Negative likelihood ratio | Positive predictive value | Negative predictive value |
|---|---|---|---|---|---|---|
| Analysis A (n = 35) | | | | | | |
| Class 2 gene expression profile | 84.6 | 92.9 | 11.9 | 0.2 | 91.7 | 86.7 |
| Monosomy 3 (aCGH) | 58.3 | 85.7 | 4.1 | 0.5 | 77.8 | 70.6 |
| Monosomy 3 (FISH) | 50.0 | 72.7 | 1.8 | 0.7 | 62.5 | 61.5 |
| Scleral invasion | 44.4 | 93.7 | 7.1 | 0.6 | 88.9 | 60.0 |
| Age | 72.2 | 68.7 | 2.3 | 0.4 | 72.2 | 68.8 |
| Anterior tumor location | 38.9 | 75.0 | 1.6 | 0.8 | 63.6 | 52.2 |
| Mixed or epithelioid cell type | 77.8 | 50.0 | 1.6 | 0.4 | 63.6 | 66.7 |
| Largest tumor diameter <18.9 mm | 58.8 | 62.5 | 1.6 | 0.7 | 62.5 | 58.8 |

TABLE 6-continued

| Prognostic factor | Sensitivity | Specificity | Positive likelihood ratio | Negative likelihood ratio | Positive predictive value | Negative predictive value |
|---|---|---|---|---|---|---|
| Gender | 72.2 | 37.5 | 1.2 | 0.7 | 56.5 | 54.5 |
| Tumor thickness <8.1 mm | 52.9 | 93.7 | 8.5 | 0.5 | 90.0 | 65.2 |
| Analysis B (n = 59) | | | | | | |
| Monosomy 3 (aCGH) | 73.1 | 85.7 | 5.1 | 0.3 | 86.4 | 72.0 |
| Monosomy 3 (FISH) | 55.6 | 85.7 | 3.9 | 0.5 | 83.3 | 60.0 |
| Scleral invasion | 40.6 | 92.3 | 5.3 | 0.6 | 86.7 | 55.8 |
| Age | 56.2 | 73.1 | 2.1 | 0.6 | 72.0 | 57.6 |
| Mixed or epithelioid cell type | 81.2 | 53.8 | 1.8 | 0.4 | 68.4 | 70.0 |
| Tumor thickness <11.3 mm | 77.4 | 46.2 | 1.4 | 0.5 | 63.2 | 63.2 |
| Gender | 46.9 | 65.4 | 1.4 | 0.8 | 62.5 | 50.0 |
| Anterior tumor location | 79.3 | 36.0 | 1.2 | 0.6 | 59.0 | 60.0 |
| Largest tumor diameter >15 mm | 71.9 | 30.8 | 1.0 | 0.9 | 56.1 | 47.1 |

In analysis B, the number of patients available for evaluation was expanded to 59 by using the gene expression profile as a surrogate end point in metastasis-free patients with less than 3-year follow-up (i.e., class 1 tumors were assigned to the "nonmetastasis" group and class 2 tumors to the "metastasis" group). The most accurate predictive factors were monosomy 3 detected by aCGH (73.1% sensitivity, 85.7% specificity), monosomy 3 detected by FISH (55.6% sensitivity, 85.7% specificity), and scleral invasion (40.6% sensitivity, 92.3% specificity).

In this study, the gene expression-based classifier predicted metastasis more accurately than clinicopathologic features and monosomy 3, assessed either by the widely used FISH method or by the more quantitative aCGH technique. This finding has important implications for patient care and future research because the vast majority of investigators currently use monosomy 3 as the standard for molecular prediction in uveal melanoma (12, 13). Gene expression profiling in uveal melanoma is extremely robust and reproducible on independent data sets and different analytic platforms, including Affymetrix and Illumina microarray chips and quantitative PCR (15-18, 21). As few as 7 genes from our 40-gene signature, which previously was validated on four independent Affymetrix data sets (17), were sufficient for accurately classifying all 26 tumors analyzed on the Illumina platform. The binary classifier has been verified independently by other investigators (16) and can be done accurately and reproducibly on fine-needle biopsy specimens (17). Thus, gene expression profiling is clinically feasible not only for the ~10% of cases that require enucleation but also for the vast majority that are treated with radiotherapy and other globe-sparing methods.

Figure 6B:
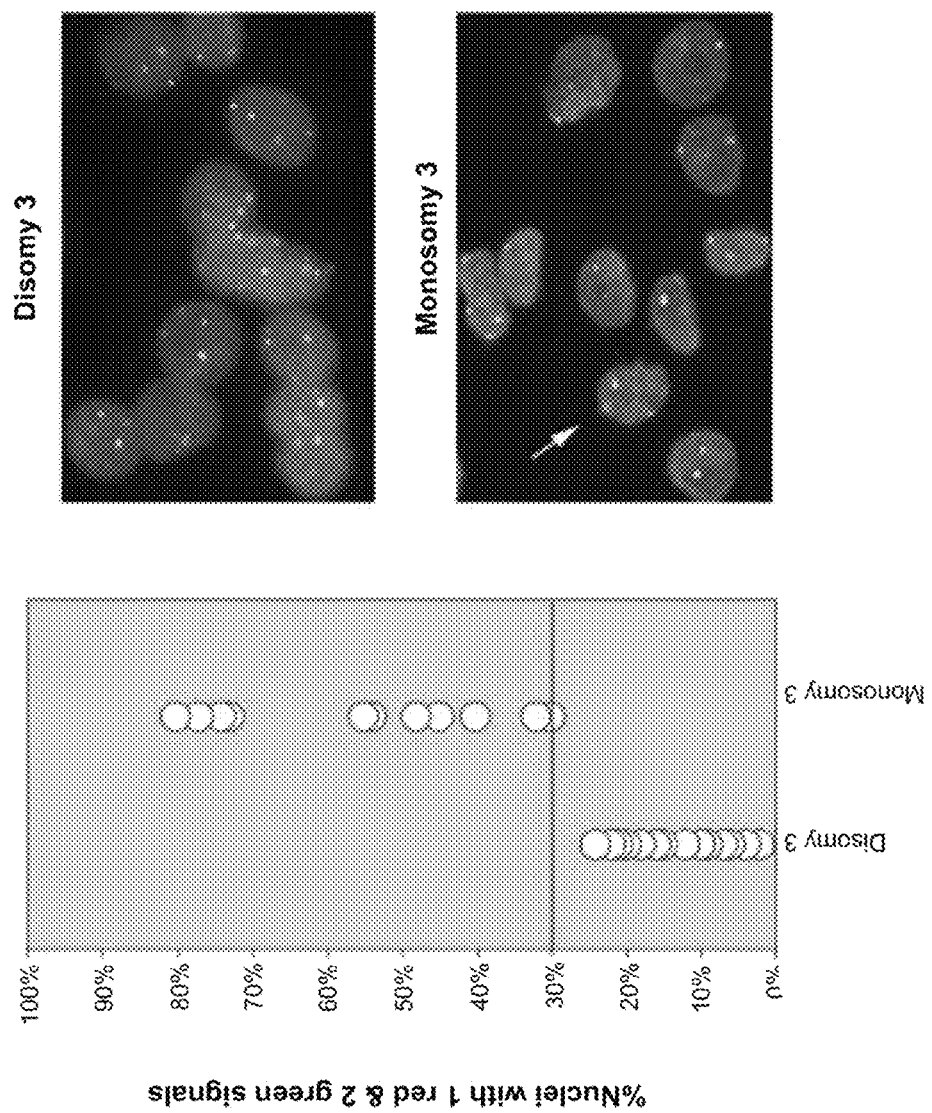
Figure 7A:
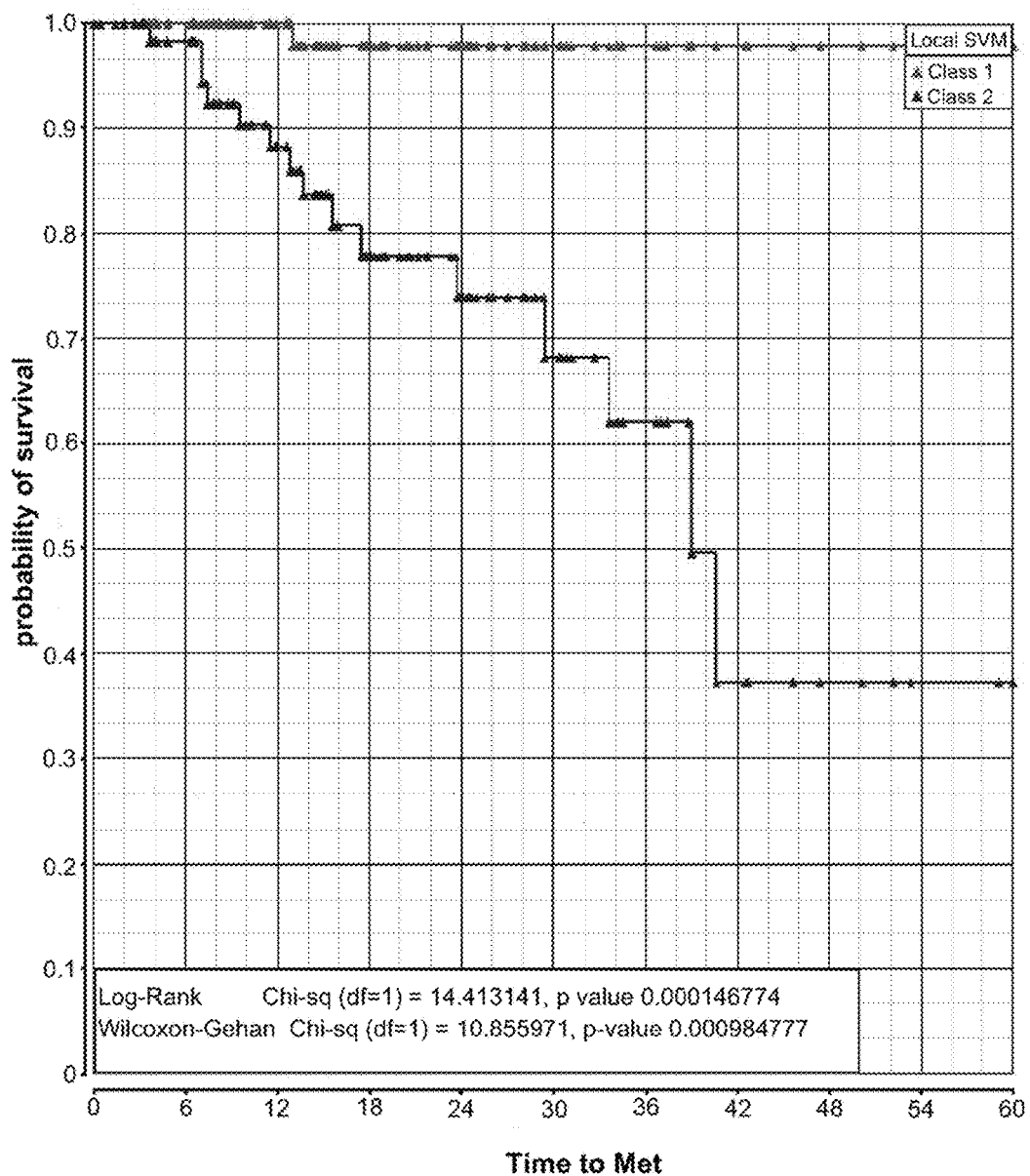
FIG. 7 depicts prospectively obtained survival data from patients whose tumor was sampled by fine needle biopsy and analyzed by (A) SVM, (B) WV, (C) RDA, and (D) PAM. The graphs represent Kaplan-Meier survival plots and show a striking difference in survival between class 1 and class 2 patients, thereby validating prospectively the earlier retrospective datasets. All four algorithms performed extremely well, as indicated by the Log-Rank p values, with SVM and WV having the best p values.
Figure 7B:
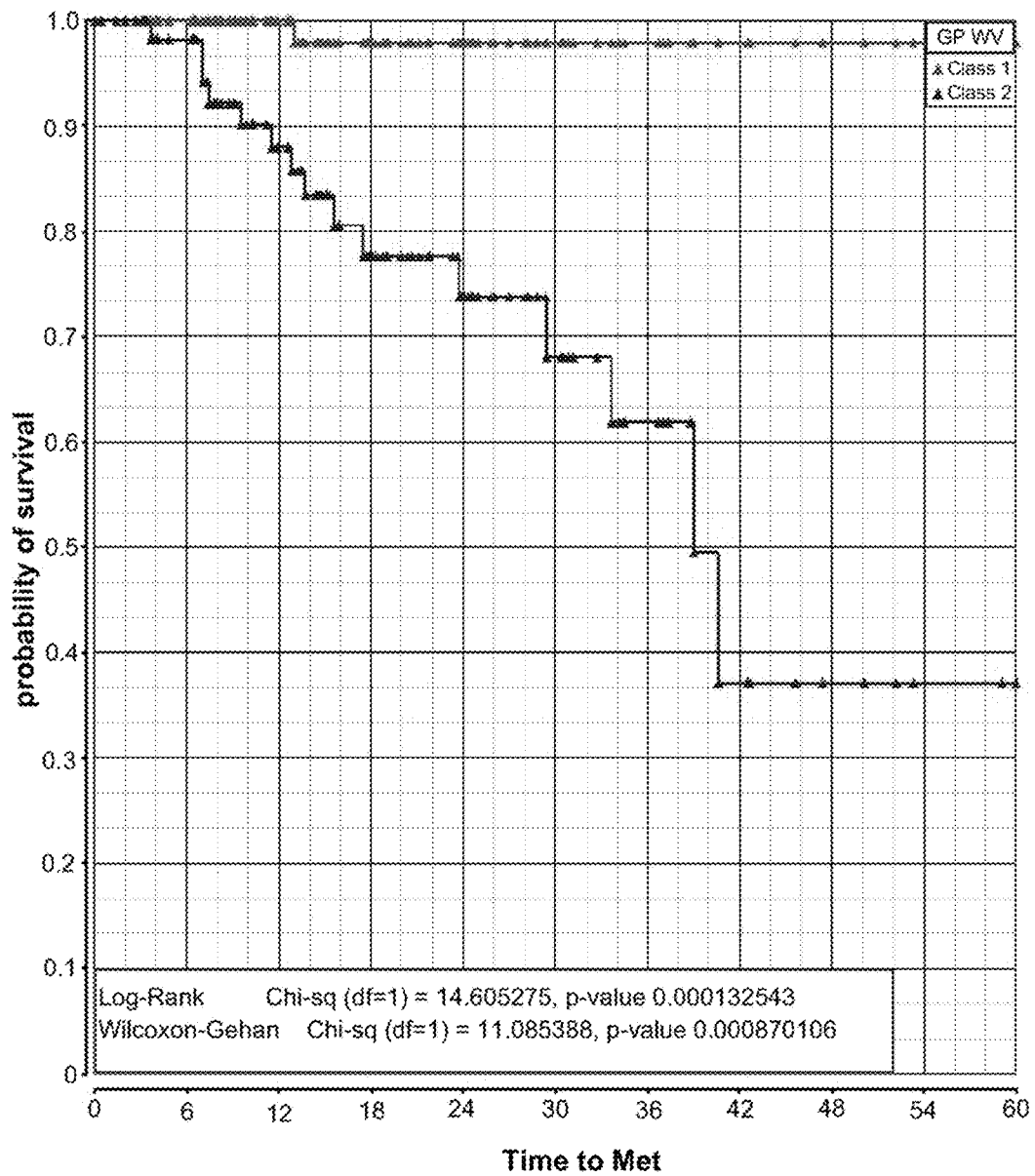
Figure 7C:
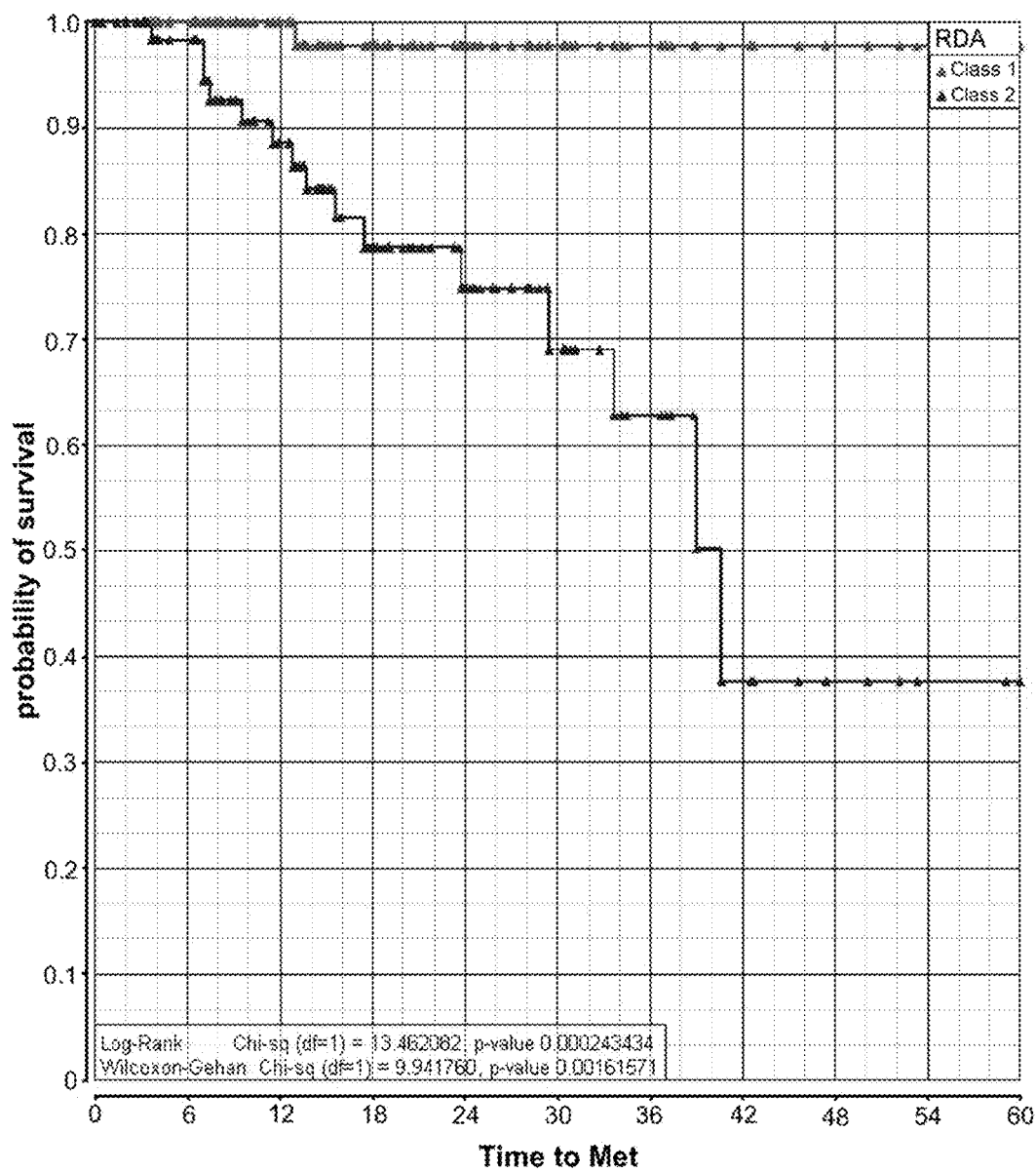
Figure 7D:
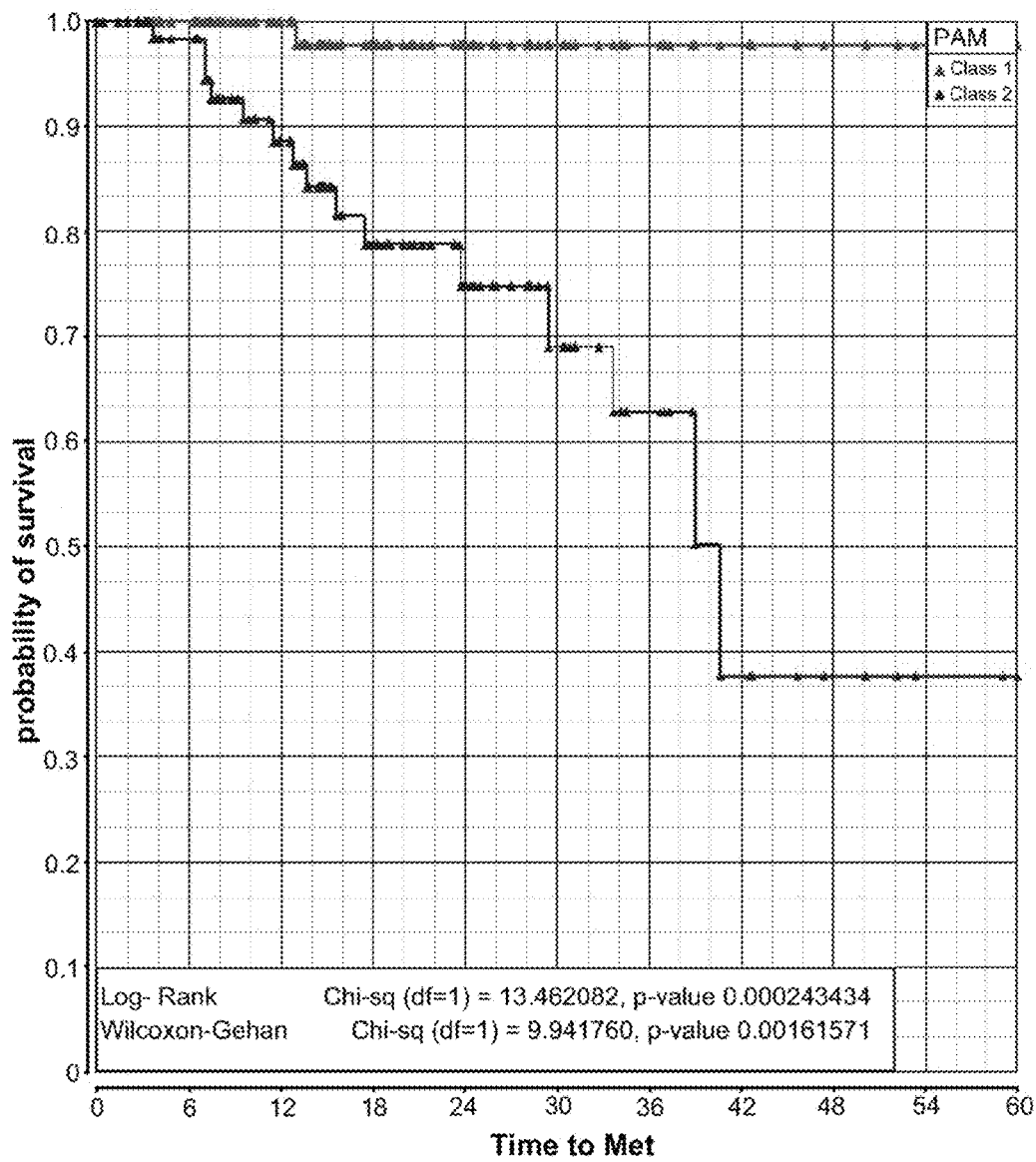

There are several potential explanations for the superiority of gene expression profiling over monosomy 3. From a technical standpoint, FISH is more challenging in uveal melanoma than in some other cancers due to its dense cellularity and elongated nuclei that weave in and out of the plane of section. The former makes it difficult to establish which signals belong to which cells, whereas the latter increases the likelihood of underestimating signal counts (false negatives). To complicate this problem, monosomy 3 is usually heterogeneous within a given tumor (FIG. 6B). Consequently, the percentage of nuclei with one chromosome 3 that is set as a threshold for calling the tumor monosomy 3 is somewhat arbitrary and may lead to false negatives or false positives. This heterogeneity for monosomy 3 can also lead to sampling error. In contrast, heterogeneity in the gene expression profile has not been found when multiple areas of the same tumor are sampled. Although these pitfalls are partially overcome by using fresh cytologic preparations rather than paraffin-embedded tissue, there are still artifacts that hinder interpretation. Most notable is the tendency for signal splitting (appearance of two closely positioned signals at the site of a single centromere), which is common with the chromosome 3 probe. For reasons that are unclear, this phenomenon is variable and is more prominent in some specimens than others, leading to potential overestimation of centromere numbers. In addition to these problems, some tumors sustain interstitial deletions on chromosome 3 rather than loss of the whole chromosome (22), which likely would be undetected by FISH, leading to false-negative calls.

Because of these shortcomings of FISH, chromosome 3 status was also assessed by aCGH, which is a quantitative technique that overcomes many of the technical obstacles of FISH. Nevertheless, the performance of aCGH was still inferior to gene expression profiling. This may be due, at least in part, to the inability of aCGH to detect isodisomy 3, which occurs in some uveal melanomas when there is loss of one chromosome 3 and duplication of the remaining, presumably abnormal chromosome 3 (23). In addition, it seems likely that gene expression profiling represents a "snapshot" that captures more of the functional complexity of the tumor visa'-vis metastatic potential than does a simple chromosomal marker, such as monosomy 3. Consistent with this idea, we recently showed that the gene expression pattern exhibited by the class 2 tumors was consistent with a primordial, epithelial-like phenotype, which may indicate that class 2 tumors contain more stem-like cancer cells with increased metastatic capacity (18).

Based on these results, plans are under way to optimize and validate the molecular classifier on a larger patient population. Ultimately, this classifier could be used to individualize the intensity and frequency of metastatic surveillance and to guide entry of high-risk patients into clinical trials of preemptive antimetastatic therapies, such as vaccines and targeted molecular agents.

References for Example 2

1. Taylor J M, Yu M, Sandler H M. Individualized predictions of disease progression following radiation therapy forprostate cancer. JClinOnco 12005; 23:816-25.
2. Efferth T, Volm M. Pharmacogenetics for individualized cancer chemotherapy. Pharmacol Ther 2005; 107:155-76.
3. Harbour J W. Clinical overview of uveal melanoma: introduction to tumors of the eye. In: Albert D M, Polans A, editors. Ocular oncology. New York: Marcel Dekker; 2003. p. 1-18.
4. Sisley K, Rennie I G, Cottam D W, Potter A M, Potter C W, Rees R C. Cytogenetic findings in six posterior uveal melanomas: involvement of chromosomes 3, 6, and 8. Genes Chromosomes Cancer 1990; 2:205-9.
5. Prescher G, Bornfeld N, Becher R. Nonrandom chromosomal abnormalities in primary uveal melanoma. J Natl Cancer Inst 1990; 82:1765-9.
6. Horsman D E, Sroka H, Rootman J, White V A. Monosomy 3 and isochromosome 8q in a uveal melanoma. Cancer Genet Cytogenet 1990; 45:249-53.
7. McNamara M, Felix C, Davison E V, Fenton M, Kennedy S M. Assessment of chromosome copy number in ocular melanoma using fluorescence in situ hybridization. Cancer Genet Cytogenet 1997; 98:4-8.
8. Gordon K B, Thompson C T, Char D H, et al. Comparative genomic hybridization in the detection of DNA copy number abnormalities in uveal melanoma. Cancer Res 1994; 54:4764-8.
9. Naus N C, van Drunen E, de Klein A, et al. Characterization of complex chromosomal abnormalities in uveal melanoma by fluorescence in situ hybridization, spectral karyotyping, and comparative genomic hybridization. Genes Chromosomes Cancer 2001; 30: 267-73.
10. Prescher G, Bornfeld N, Hirche H, Horsthemke B, Jockel K H, Becher R. Prognostic implications of monosomy in uveal melanoma. Lancet 1996; 347: 1222^5. 1. Kilic E, van Gils W, Lodder E, et al. Clinical and cytogenetic analyses in uveal melanoma. Invest Ophthalmol Vis Sci 2006; 47:3703-7.
12. Patel K A, Edmondson N D, Talbot F, Parsons M A, Rennie I G, Sisley K. Prediction of prognosis in patients with uveal melanoma using fluorescence in situ hybridisation. Br Ophthalmol 2001; 85:1440-4.
13. Midena E, Bonaldi L, Parrozzani R, Tebaldi E, Boccassini B, Vujosevic S. In vivo detection of monosomy in eyes with medium-sized uveal melanoma using transscleral fine needle aspiration biopsy. Eur Ophthalmol 2006; 16:422-5.
14. Sandinha M T, Farquharson M A, McKay I C, Roberts F. Monosomy predicts death but not time until death in choroidal melanoma. Invest Ophthalmol Vis Sci 2005; 46:3497-501.
15. Onken M D, Worley L A, Ehlers J P, Harbour J W. Gene expression profiling in uveal melanoma reveals two molecular classes and predicts metastatic death. Cancer Res 2004; 64:7205-9.
16. Tschentscher F, Husing J, Holter T, et al. Tumor classification based on gene expression profiling shows that uveal melanomas with and without monosomy represent two distinct entities. Cancer Res 2003; 63:2578-84.
17. Onken M D, Worley L A, Davila R M, Char D H, Harbour J W. Prognostic testing in uveal melanoma by transcriptomic profiling of fine needle biopsy specimens. Mol Diagn 2006; 8:567-73.
18. Onken M D, Ehlers J P, Worley L A, Makita J, Yokota Y, Harbour J W. Functional gene expression analysis uncovers phenotypic switch in aggressive uveal melanomas. Cancer Res 2006; 66:4602-9.
19. Perry A, Roth K A, Banerjee R, Fuller C E, Gutmann D H. NF1 deletions in S-100 protein-positive and negative cells of sporadic and neurofibromatosis 1 (NF1) associated plexiform neurofibromas and malignant peripheral nerve sheath tumors. Am Pathol 2001; 159:57-61.
20. Pinkel D, Segraves R, Sudar D, et al. High resolution analysis of DNA copy number variation using comparative genomic hybridization to microarrays. Nat Genet 1998; 20:207-11.
21. Onken M D, Lin A Y, Worley L A, Folberg R, Harbour J W. Association between microarray gene expression signature and extravascular matrix patterns in primary uveal melanomas. Am Ophthalmol 2005; 140:748-9.
22. Cross N A, Ganesh A, Parpia M, Murray A K, Rennie I G, Sisley K. Multiple locations on chromosome are the targets of specific deletions in uveal melanoma. Eye 2006; 20:476-81.
23. White V A, McNeil B K, Thiberville L, Horsman D E. Acquired homozygosity (isodisomy) of chromosome during clonal evolution of uveal melanoma: association with morphologic heterogeneity. Genes Chromosomes Cancer 1996; 15:138-43.

Example 3

Risk Analysis Using Twelve Nucleic Acid Sequences

RNA was extracted from fine needle biopsy samples from three different groups of subjects. The RNA was reverse transcribed and the level of expression of each of the genes CDH1, ECM1, EIF1B, FXR1, HTR2B, ID2, LMCD1, LTA4H, MTUS1, RAB31, ROBO1, and SATB1 was determined using a TLDA card from Applied Biosystems. Assay IDs are as follows: CDH1 Hs00170423_m1; ECM1 Hs00189435_m1; EIF1B Hs00271856_m1; FXR1 Hs01096865_m1; HTR2B Hs00168362_m1; ID2 Hs00747379_m1; LMCD1 Hs00205871_m1; LTA4H Hs00168505_m1; MRPS21 Hs00230458_m1; MTUS1 Hs00368183_m1; RAB31 Hs00199313_m1; RBM23 Hs00216503_m1; ROBO1 Hs00268049_m1; SAP130 Hs00368617_m1; and SATB1 Hs00161515_m1.

The level of expression was correlated with a risk of metastasis using a SVM and a WV algorithm.

The data is presented in Table 7, Table 8, and Table 9 below. The classification of the shaded subjects differed depending on the algorithm used.

TABLE 7

| Sample | SVM | Discriminant | WV | Confidence | PAM | PAM Prob | RDA | WV v SVM | PAM v SVM | RDA v SVM |
|---|---|---|---|---|---|---|---|---|---|---|
| DCNB 001A | Class1 | −0.834906 | Class1 | 0.863 | Class1 | 0.992917762 | Class1 | 1 | 1 | 1 |
| DCNB 001B | Class1 | −1.10213 | Class1 | 0.7358 | Class1 | 0.999790922 | Class1 | 1 | 1 | 1 |
| DCNB 002 | Class1 | −0.811529 | Class1 | 0.7856 | Class1 | 0.998950572 | Class1 | 1 | 1 | 1 |
| DCNB 003 | Class1 | −1.07985 | Class1 | 1 | Class1 | 0.999951103 | Class1 | 1 | 1 | 1 |
| DCNB 004 | Class2 | 0.269152 | Class2 | 0.28 | Class2 | 0.9839243 | Class2 | 1 | 1 | 1 |
| DCNB 005 | Class1 | −0.946388 | Class1 | 0.9387 | Class1 | 0.999744855 | Class1 | 1 | 1 | 1 |
| DCNB 006 | Class2 | 0.306368 | Class2 | 0.2343 | Class2 | 0.970731511 | Class2 | 1 | 1 | 1 |
| DCNB 007 | Class2 | 0.260768 | Class1 | 0.0146 | Class2 | 0.9771316 | Class2 | 0 | 1 | 1 |
| DCNB 009 | Class1 | −0.17107 | Class1 | 0.2958 | Class1 | 0.810402539 | Class1 | 1 | 1 | 1 |
| DCNB 010 | Class1 | −0.767964 | Class1 | 0.831 | Class1 | 0.999963431 | Class1 | 1 | 1 | 1 |
| DCNB 011 | Class1 | −1.09743 | Class1 | 0.9777 | Class1 | 0.99989001 | Class1 | 1 | 1 | 1 |
| DCNB 012 | Class2 | 0.912663 | Class2 | 0.9653 | Class2 | 0.999228838 | Class2 | 1 | 1 | 1 |
| DCNB 013 | Class1 | −0.854329 | Class1 | 0.9146 | Class1 | 0.999924203 | Class1 | 1 | 1 | 1 |
| DCNB 014 | Class1 | −1.03811 | Class1 | 0.9891 | Class1 | 0.999819473 | Class1 | 1 | 1 | 1 |
| DCNB 015 | Class2 | 0.131821 | Class2 | 0.0469 | Class2 | 0.944354396 | Class2 | 1 | 1 | 1 |
| DCNB 016 | Class1 | −0.884284 | Class1 | 1 | Class1 | 0.999205833 | Class1 | 1 | 1 | 1 |
| DCNB 017 | Class2 | 0.127442 | Class2 | 0.2256 | Class2 | 0.918969127 | Class2 | 1 | 1 | 1 |
| DCNB 018 | Class1 | −0.182921 | Class1 | 0.0453 | Class1 | 0.620818339 | Class1 | 1 | 1 | 1 |
| DCNB 019 | Class1 | −0.846266 | Class1 | 0.8027 | Class1 | 0.999985466 | Class1 | 1 | 1 | 1 |
| DCNB 020 | Class2 | 0.50709 | Class2 | 0.5149 | Class2 | 0.854218984 | Class2 | 1 | 1 | 1 |
| DCNB 021 | Class1 | −0.791213 | Class1 | 0.7498 | Class1 | 0.997838782 | Class1 | 1 | 1 | 1 |
| DCNB 022 | Class2 | 0.473096 | Class2 | 0.3511 | Class2 | 0.9854374 | Class2 | 1 | 1 | 1 |
| DCNB 023 | Class1 | −1.29095 | Class1 | 1 | Class1 | 0.999988519 | Class1 | 1 | 1 | 1 |
| DCNB 024 | Class2 | 1.02672 | Class2 | 0.5768 | Class2 | 0.999276611 | Class2 | 1 | 1 | 1 |
| DCNB 024P | Class2 | 1.26011 | Class2 | 0.7109 | Class2 | 0.99994223 | Class2 | 1 | 1 | 1 |
| DCNB 025 | Class1 | −1.01636 | Class1 | 0.6177 | Class1 | 0.999406667 | Class1 | 1 | 1 | 1 |
| DCNB 027 | Class2 | 0.818827 | Class2 | 0.5571 | Class2 | 0.999686511 | Class2 | 1 | 1 | 1 |
| DCNB 028 | Class2 | 0.526428 | Class2 | 0.0678 | Class2 | 0.98781153 | Class2 | 1 | 1 | 1 |
| DCNB 029 | Class2 | 0.595274 | Class2 | 0.6049 | Class2 | 0.998348172 | Class2 | 1 | 1 | 1 |
| DCNB 030 | Class2 | 0.0049423 | Class2 | 0.2373 | Class2 | 0.703925879 | Class2 | 1 | 1 | 1 |
| DCNB 031 | Class1 | −0.422871 | Class1 | 0.5551 | Class1 | 0.966678893 | Class1 | 1 | 1 | 1 |
| DCNB 032 | Class1 | −1.06789 | Class1 | 0.9911 | Class1 | 0.999960844 | Class1 | 1 | 1 | 1 |
| DCNB 033 | Class1 | −1.01256 | Class1 | 0.6267 | Class1 | 0.988279673 | Class1 | 1 | 1 | 1 |
| DCNB 034 | Class1 | −1.08637 | Class1 | 1 | Class1 | 0.999939977 | Class1 | 1 | 1 | 1 |
| DCNB 035 | Class2 | 0.257113 | Class2 | 0.4203 | Class2 | 0.995068601 | Class2 | 1 | 1 | 1 |
| DCNB 036 | Class1 | −1.04394 | Class1 | 0.8672 | Class1 | 0.999623965 | Class1 | 1 | 1 | 1 |
| DCNB 037 | Class1 | −0.988384 | Class1 | 1 | Class1 | 0.999878124 | Class1 | 1 | 1 | 1 |
| DCNB 038 | Class2 | 0.215198 | Class2 | 0.2835 | Class1 | 0.690244822 | Class1 | 1 | 0 | 0 |
| DCNB 039 | Class1 | −1.25691 | Class1 | 0.9535 | Class1 | 0.99996467 | Class1 | 1 | 1 | 1 |
| DCNB 040 | Class1 | −1.05095 | Class1 | 0.9649 | Class1 | 0.999693782 | Class1 | 1 | 1 | 1 |
| DCNB 041 | Class1 | −1.09812 | Class1 | 0.993 | Class1 | 0.999989836 | Class1 | 1 | 1 | 1 |
| DCNB 042 | Class2 | 0.252717 | Class2 | 0.1576 | Class2 | 0.980149117 | Class2 | 1 | 1 | 1 |
| DCNB 043 | Class1 | −0.410187 | Class1 | 0.4588 | Class1 | 0.886358157 | Class1 | 1 | 1 | 1 |
| DCNB 044 | Class1 | −0.239479 | Class1 | 0.3773 | Class2 | 0.783182424 | Class2 | 1 | 0 | 0 |
| DCNB 045 | Class1 | −0.89104 | Class1 | 0.8581 | Class1 | 0.999849012 | Class1 | 1 | 1 | 1 |
| DCNB 046 | Class1 | −0.817603 | Class1 | 0.7719 | Class1 | 0.993125493 | Class1 | 1 | 1 | 1 |
| DCNB 047 | Class1 | −0.412904 | Class1 | 0.6353 | Class1 | 0.99472291 | Class1 | 1 | 1 | 1 |
| DCNB 048 | Class1 | −1.05567 | Class1 | 1 | Class1 | 0.999975174 | Class1 | 1 | 1 | 1 |
| DCNB 049 | Class1 | −0.881715 | Class1 | 1 | Class1 | 0.998869217 | Class1 | 1 | 1 | 1 |
| DCNB 050 | Class1 | −1.12425 | Class1 | 1 | Class1 | 0.999882801 | Class1 | 1 | 1 | 1 |
| DCNB 051 | Class2 | 1.12167 | Class2 | 0.974 | Class2 | 0.999958349 | Class2 | 1 | 1 | 1 |
| DCNB 052 | Class2 | 0.444106 | Class2 | 0.5057 | Class2 | 0.995738284 | Class2 | 1 | 1 | 1 |
| DCNB 053 | Class2 | 0.889831 | Class2 | 0.7359 | Class2 | 0.99871448 | Class2 | 1 | 1 | 1 |
| DCNB 054 | Class1 | −0.728827 | Class1 | 0.5407 | Class1 | 0.975419152 | Class1 | 1 | 1 | 1 |
| DCNB 055 | Class1 | −0.854032 | Class1 | 0.6764 | Class1 | 0.996949146 | Class1 | 1 | 1 | 1 |
| DCNB 056 | Class2 | 1.34399 | Class2 | 0.8728 | Class2 | 0.998961862 | Class2 | 1 | 1 | 1 |
| DCNB 057 | Class1 | −0.753907 | Class1 | 0.6708 | Class1 | 0.998746399 | Class1 | 1 | 1 | 1 |
| DCNB 058 | Class2 | 1.11675 | Class2 | 0.8249 | Class2 | 0.998566762 | Class2 | 1 | 1 | 1 |
| DCNB 059 | Class1 | −0.449974 | Class1 | 0.4901 | Class1 | 0.752470212 | Class1 | 1 | 1 | 1 |
| DCNB 060 | Class1 | −0.838262 | Class1 | 0.7013 | Class1 | 0.67469684 | Class1 | 1 | 1 | 1 |
| DCNB 061 | Class1 | −0.316938 | Class1 | 0.6148 | Class1 | 0.969617595 | Class1 | 1 | 1 | 1 |
| DCNB 062 | Class1 | −1.132 | Class1 | 0.8709 | Class1 | 0.999649746 | Class1 | 1 | 1 | 1 |
| DCNB 063 | Class1 | −1.17657 | Class1 | 1 | Class1 | 0.999850494 | Class1 | 1 | 1 | 1 |
| DCNB 064 | Class1 | −1.03074 | Class1 | 0.9066 | Class1 | 0.999060671 | Class1 | 1 | 1 | 1 |
| DCNB 065 | Class2 | 0.785433 | Class2 | 0.9009 | Class2 | 0.999687435 | Class2 | 1 | 1 | 1 |
| DCNB 066 | Class1 | −0.843793 | Class1 | 0.9128 | Class1 | 0.999817781 | Class1 | 1 | 1 | 1 |
| DCNB 067 | Class2 | 1.58146 | Class2 | 0.9066 | Class2 | 0.999997721 | Class2 | 1 | 1 | 1 |
| DCNB 068A | Class2 | 1.00654 | Class2 | 0.979 | Class2 | 0.99984105 | Class2 | 1 | 1 | 1 |
| DCNB 068b | Class2 | 1.58812 | Class2 | 1 | Class2 | 0.999966385 | Class2 | 1 | 1 | 1 |
| DCNB 069 | Class1 | −1.03875 | Class1 | 0.8742 | Class1 | 0.997673762 | Class1 | 1 | 1 | 1 |
| DCNB 070 | Class2 | 0.65472 | Class2 | 0.5171 | Class2 | 0.999964245 | Class2 | 1 | 1 | 1 |
| DCNB 071 | Class1 | −1.13635 | Class1 | 0.9057 | Class1 | 0.999052155 | Class1 | 1 | 1 | 1 |
| DCNB 072 | Class1 | −1.02766 | Class1 | 1 | Class1 | 0.999318501 | Class1 | 1 | 1 | 1 |
| DCNB 073 | Class1 | −1.28117 | Class1 | 0.8219 | Class1 | 0.99934508 | Class1 | 1 | 1 | 1 |
| DCNB 074 | Class2 | 1.21446 | Class2 | 1 | Class2 | 0.999059765 | Class2 | 1 | 1 | 1 |
| DCNB 076 | Class2 | 0.0830351 | Class1 | 0.3792 | Class2 | 0.61629143 | Class1 | 0 | 1 | 0 |
| DCNB 077 | Class1 | −1.0197 | Class1 | 0.5292 | Class1 | 0.822822223 | Class1 | 1 | 1 | 1 |

TABLE 7-continued

| Sample | SVM | Discriminant | WV | Confidence | PAM | PAM Prob | RDA | WV v SVM | PAM v SVM | RDA v SVM |
|---|---|---|---|---|---|---|---|---|---|---|
| DCNB 078 | Class2 | 1.12338 | Class2 | 0.9939 | Class2 | 0.999771014 | Class2 | 1 | 1 | 1 |
| DCNB 079 | Class1 | −0.198461 | Class1 | 0.4598 | Class1 | 0.78895831 | Class1 | 1 | 1 | 1 |
| DCNB 080 | Class2 | 0.515802 | Class2 | 0.6011 | Class2 | 0.98590354 | Class2 | 1 | 1 | 1 |
| DCNB 081 | Class2 | −0.476246 | Class2 | 0.1396 | Class2 | 0.988900151 | Class2 | 1 | 1 | 1 |
| DCNB 082 | Class1 | −0.895757 | Class1 | 0.9349 | Class1 | 0.999884638 | Class1 | 1 | 1 | 1 |
| DCNB 083 | Class1 | −0.989095 | Class1 | 0.9769 | Class1 | 0.999966484 | Class1 | 1 | 1 | 1 |
| DCNB 084 | Class1 | −0.693627 | Class1 | 0.6994 | Class1 | 0.996926638 | Class1 | 1 | 1 | 1 |
| DCNB 085 | Class1 | −0.417019 | Class1 | 0.6136 | Class1 | 0.999805982 | Class1 | 1 | 1 | 1 |
| DCNB 086 | Class1 | −0.41017 | Class1 | 0.3641 | Class1 | 0.708658943 | Class1 | 1 | 1 | 1 |
| DCNB 087 | Class2 | 0.0947372 | Class2 | 0.2552 | Class1 | 0.952628901 | Class2 | 1 | 0 | 0 |
| DCNB 088 | Class2 | 1.31915 | Class2 | 0.9902 | Class2 | 0.999486677 | Class2 | 1 | 1 | 1 |
| DCNB 089 | Class1 | −0.782728 | Class1 | 0.7499 | Class1 | 0.999043311 | Class1 | 1 | 1 | 1 |
| DCNB 090 | Class2 | 0.619917 | Class2 | 0.6979 | Class2 | 0.98399188 | Class2 | 1 | 1 | 1 |
| DCNB 091 | Class1 | −0.723238 | Class1 | 0.9276 | Class1 | 0.999938079 | Class1 | 1 | 1 | 1 |
| DCNB 092 | Class2 | 0.41794 | Class2 | 0.7447 | Class2 | 0.978484468 | Class2 | 1 | 1 | 1 |
| DCNB 093 | Class2 | 0.246177 | Class2 | 0.0933 | Class1 | 0.738088532 | Class1 | 1 | 0 | 0 |
| DCNB 094 | Class2 | 1.24354 | Class2 | 0.9957 | Class2 | 0.999776216 | Class2 | 1 | 1 | 1 |
| DCNB 095 | Class1 | −0.557555 | Class1 | 0.7944 | Class1 | 0.997808465 | Class1 | 1 | 1 | 1 |
| DCNB 096 | Class2 | 1.27331 | Class2 | 1 | Class2 | 0.998339224 | Class2 | 1 | 1 | 1 |
| DCNB 097 | Class1 | −0.017905 | Class2 | 0.0387 | Class2 | 0.765601712 | Class2 | 0 | 0 | 0 |
| DCNB 098 | Class2 | 0.075674 | Class2 | 0.0138 | Class2 | 0.931377571 | Class1 | 1 | 0 | 0 |
| DCNB 099 | Class1 | −0.512568 | Class1 | 0.4062 | Class1 | 0.926348199 | Class1 | 1 | 1 | 1 |
| DCNB 100 | Class1 | −1.00625 | Class1 | 0.915 | Class1 | 0.999887681 | Class1 | 1 | 1 | 1 |
| DCNB 101 | Class1 | −1.07581 | Class1 | 0.9934 | Class1 | 0.999946137 | Class1 | 1 | 1 | 1 |
| DCNB 102 | Class1 | −0.486707 | Class1 | 0.664 | Class1 | 0.999235531 | Class1 | 1 | 1 | 1 |
| DCNB 103 | Class1 | −1.24279 | Class1 | 0.9954 | Class1 | 0.999650744 | Class1 | 1 | 1 | 1 |
| DCNB 104 | Class2 | 0.603008 | Class2 | 0.5676 | Class2 | 0.699695054 | Class2 | 1 | 1 | 1 |
| DCNB 105 | Class2 | 1.14711 | Class2 | 0.5914 | Class2 | 0.985911426 | Class2 | 1 | 1 | 1 |
| DCNB 106 | Class1 | −0.404487 | Class1 | 0.596 | Class1 | 0.990799358 | Class1 | 1 | 1 | 1 |
| DCNB 108 | Class2 | 0.368669 | Class2 | 0.0287 | Class2 | 0.615131663 | Class2 | 1 | 1 | 1 |
| DCNB 110 | Class1 | −0.968472 | Class1 | 0.6858 | Class1 | 0.99829909 | Class1 | 1 | 1 | 1 |
| DCNB 111 | Class1 | −0.903505 | Class1 | 0.6373 | Class1 | 0.994164881 | Class1 | 1 | 1 | 1 |
| DCNB 112 | Class2 | 1.22494 | Class2 | 1 | Class2 | 0.998778011 | Class2 | 1 | 1 | 1 |
| DCNB 113 | Class2 | 0.792139 | Class2 | 0.9852 | Class2 | 0.98502535 | Class2 | 1 | 1 | 1 |
| DCNB 114 | Class1 | −0.76473 | Class1 | 0.9537 | Class1 | 0.999901691 | Class1 | 1 | 1 | 1 |
| DCNB 115 | Class1 | −1.04375 | Class1 | 0.7757 | Class1 | 0.994255632 | Class1 | 1 | 1 | 1 |
| DCNB 116 | Class1 | −0.706336 | Class1 | 0.6634 | Class1 | 0.993231128 | Class1 | 1 | 1 | 1 |
| DCNB 117 | Class1 | −1.03295 | Class1 | 0.9605 | Class1 | 0.999968562 | Class1 | 1 | 1 | 1 |
| DCNB 119 | Class1 | −0.879289 | Class1 | 0.8371 | Class1 | 0.998844675 | Class1 | 1 | 1 | 1 |
| DCNB 120 | Class2 | 0.691451 | Class2 | 0.9202 | Class2 | 0.991212613 | Class2 | 1 | 1 | 1 |
| DCNB 122 | Class2 | 0.809212 | Class2 | 0.8808 | Class2 | 0.994113411 | Class2 | 1 | 1 | 1 |
| DCNB 123 | Class2 | 1.07486 | Class2 | 0.9464 | Class2 | 0.999356444 | Class2 | 1 | 1 | 1 |
| DCNB 124 | Class2 | 1.57145 | Class2 | 0.9098 | Class2 | 0.99995096 | Class2 | 1 | 1 | 1 |
| DCNB 127 | Class1 | −0.931688 | Class1 | 0.9552 | Class1 | 0.99973936 | Class1 | 1 | 1 | 1 |
| DCNB 128 | Class2 | −0.264002 | Class1 | 0.2508 | Class1 | 0.926599421 | Class1 | 0 | 0 | 0 |
| DCNB 130 | Class2 | 0.449479 | Class2 | 0.3256 | Class2 | 0.9905784 | Class2 | 1 | 1 | 1 |
| DCNB 132 | Class2 | 1.19498 | Class2 | 1 | Class2 | 0.99931191 | Class2 | 1 | 1 | 1 |
| DCNB 134* | Class1 | −0.114799 | Class2 | 0.0994 | Class1 | 0.825010004 | Class1 | 0 | 1 | 1 |
| DCNB 136 | Class1 | −1.02633 | Class1 | 0.606 | Class1 | 0.987592172 | Class1 | 1 | 1 | 1 |
| DCNB 137 | Class2 | 1.39775 | Class2 | 1 | Class2 | 0.9998999 | Class2 | 1 | 1 | 1 |
| DCNB 138 | Class1 | −0.974764 | Class1 | 0.6879 | Class1 | 0.997773292 | Class1 | 1 | 1 | 1 |
| DCNB 139 | Class1 | −0.995455 | Class1 | 0.4845 | Class1 | 0.902704119 | Class1 | 1 | 1 | 1 |
| DCNB 140 | Class2 | 0.317682 | Class2 | 0.3089 | Class2 | 0.997164321 | Class2 | 1 | 1 | 1 |
| DCNB 141 | Class1 | −0.809194 | Class1 | 0.5327 | Class1 | 0.971046898 | Class1 | 1 | 1 | 1 |
| DCNB 142 | Class1 | −0.764945 | Class1 | 0.5518 | Class1 | 0.984915676 | Class1 | 1 | 1 | 1 |
| DCNB 143 | Class1 | −1.03427 | Class1 | 0.7945 | Class1 | 0.999984375 | Class1 | 1 | 1 | 1 |
| DCNB 144 | Class1 | −0.213574 | Class1 | 0.2131 | Class2 | 0.727503047 | Class2 | 1 | 0 | 0 |
| DCNB 145 | Class2 | 0.0975667 | Class2 | 0.0012 | Class2 | 0.635764497 | Class2 | 1 | 1 | 1 |
| DCNB 146 | Class2 | 0.241008 | Class2 | 0.2276 | Class2 | 0.978061381 | Class2 | 1 | 1 | 1 |
| DCNB 147 | Class1 | −0.0965166 | Class1 | 0.1003 | Class2 | 0.911431931 | Class2 | 1 | 0 | 0 |
| DCNB 148 | Class2 | 0.398606 | Class2 | 0.4362 | Class2 | 0.997214472 | Class2 | 1 | 1 | 1 |
| DCNB 149 | Class1 | −0.840212 | Class1 | 0.9552 | Class1 | 0.999791945 | Class1 | 1 | 1 | 1 |
| DCNB 150 | Class2 | 1.0919 | Class2 | 0.9867 | Class2 | 0.999535324 | Class2 | 1 | 1 | 1 |
| DCNB 151 | Class1 | −0.89383 | Class1 | 0.8918 | Class1 | 0.999382615 | Class1 | 1 | 1 | 1 |
| DCNB 152 | Class1 | −0.924584 | Class1 | 0.7188 | Class1 | 0.988974207 | Class1 | 1 | 1 | 1 |
| DCNB 153 | Class2 | 1.23681 | Class2 | 0.9855 | Class2 | 0.999806938 | Class2 | 1 | 1 | 1 |
| DCNB 154 | Class2 | 1.58568 | Class2 | 0.92 | Class2 | 0.999989611 | Class2 | 1 | 1 | 1 |
| DCNB 157 | Class2 | 0.702296 | Class2 | 0.9064 | Class2 | 0.995964394 | Class2 | 1 | 1 | 1 |
| DCNB 158 | Class1 | −0.218314 | Class1 | 0.045 | Class1 | 0.999978464 | Class1 | 1 | 1 | 1 |
| DCNB 159 | Class1 | −0.293086 | Class1 | 0.199 | Class1 | 0.999674017 | Class1 | 1 | 1 | 1 |
| DCNB 161 | Class2 | 0.0117648 | Class2 | 0.1546 | Class1 | 0.998165537 | Class1 | 1 | 0 | 0 |
| DCNB 162 | Class2 | 1.01012 | Class2 | 0.7826 | Class2 | 0.99938833 | Class2 | 1 | 1 | 1 |
| DCNB 163 | Class2 | 0.147494 | Class2 | 0.4308 | Class2 | 0.996561158 | Class2 | 1 | 1 | 1 |
| DCNB 164 | Class2 | 0.160407 | Class2 | 4.00E−04 | Class2 | 0.945150504 | Class2 | 1 | 1 | 1 |
| DCNB 165 | Class1 | −0.644369 | Class1 | 0.4558 | Class1 | 0.939419399 | Class1 | 1 | 1 | 1 |
| DCNB 166 | Class1 | −1.0093 | Class1 | 1 | Class1 | 0.999962124 | Class1 | 1 | 1 | 1 |
| DCNB 167 | Class2 | 0.810234 | Class2 | 0.1844 | Class2 | 0.999889846 | Class2 | 1 | 1 | 1 |

TABLE 7-continued

| Sample | SVM | Discriminant | WV | Confidence | PAM | PAM Prob | RDA | WV v SVM | PAM v SVM | RDA v SVM |
|---|---|---|---|---|---|---|---|---|---|---|
| DCNB 168 | Class1 | −0.386908 | Class1 | 0.5565 | Class2 | 0.937495443 | Class2 | 1 | 0 | 0 |
| DCNB 169* | Class1 | −0.643313 | Class1 | 0.0475 | Class2 | 0.721230926 | Class1 | 1 | 0 | 1 |
| DCNB 171 | Class1 | −0.218236 | Class1 | 0.2875 | Class2 | 0.992793436 | Class2 | 1 | 0 | 0 |
| DCNB 172 | Class1 | −0.671264 | Class1 | 0.8379 | Class1 | 0.981790922 | Class1 | 1 | 1 | 1 |
| DCNB 173 | Class1 | −0.442507 | Class1 | 0.5332 | Class2 | 0.690894888 | Class1 | 1 | 1 | 1 |
| DCNB 174 | Class1 | −0.843159 | Class1 | 0.3033 | Class1 | 0.940376755 | Class1 | 1 | 1 | 1 |
| DCNB 175 | Class2 | 0.0732303 | Class1 | 0.2662 | Class1 | 0.948918134 | Class1 | 0 | 0 | 0 |
| DCNB 176 | Class1 | −0.273352 | Class1 | 0.5437 | Class1 | 0.997693993 | Class1 | 1 | 1 | 1 |
| DCNB 177 | Class2 | 1.28114 | Class2 | 0.9769 | Class2 | 0.998893642 | Class2 | 1 | 1 | 1 |
| DCNB 178 | Class2 | 0.215147 | Class2 | 0.0737 | Class1 | 0.733501159 | Class2 | 1 | 0 | 1 |
| DCNB 179 | Class2 | 0.257464 | Class2 | 0.1377 | Class1 | 0.67395305 | Class2 | 1 | 0 | 1 |
| DCNB 180 | Class1 | −0.902271 | Class1 | 1 | Class1 | 0.999786635 | Class1 | 1 | 1 | 1 |
| DCNB 181 | Class1 | −0.865637 | Class1 | 0.9374 | Class1 | 0.999834775 | Class1 | 1 | 1 | 1 |
| DCNB 182 | Class1 | −0.899746 | Class1 | 0.9014 | Class1 | 0.99565937 | Class1 | 1 | 1 | 1 |
| DCNB 183 | Class1 | −0.724009 | Class1 | 0.4851 | Class1 | 0.992571865 | Class1 | 1 | 1 | 1 |
| DCNB 184 | Class2 | 0.5486 | Class2 | 0.7232 | Class2 | 0.965237182 | Class2 | 1 | 1 | 1 |
| DCNB 185 | Class1 | −0.836645 | Class1 | 0.8369 | Class1 | 0.998089365 | Class1 | 1 | 1 | 1 |
| DCNB 186 | Class1 | −0.654277 | Class1 | 0.6969 | Class1 | 0.979348141 | Class1 | 1 | 1 | 1 |
| DCNB 187 | Class1 | −0.755353 | Class1 | 0.9926 | Class1 | 0.9977584 | Class1 | 1 | 1 | 1 |
| DCNB 188 | Class1 | −0.841063 | Class1 | 0.4811 | Class2 | 0.702478442 | Class1 | 1 | 0 | 1 |
| DCNB 191 | Class1 | −0.869007 | Class1 | 0.9835 | Class1 | 0.930227638 | Class1 | 1 | 1 | 1 |
| DCNB 192 | Class1 | −1.01604 | Class1 | 0.9098 | Class1 | 0.947186348 | Class1 | 1 | 1 | 1 |
| DCNB 194 | Class1 | −0.522368 | Class1 | 0.413 | Class1 | 0.64943016 | Class1 | 1 | 1 | 1 |

TABLE 8

| Sample | SVM | Discriminant | WV | Confidence | PAM | PAM Prob | RDA | WV v SVM | PAM v SVM | RDA v SVM |
|---|---|---|---|---|---|---|---|---|---|---|
| JJA 001 | Class2 | 1.27737 | Class2 | 0.5783 | Class2 | 0.986099413 | Class2 | 1 | 1 | 1 |
| JJA 002 | Class2 | 0.641227 | Class2 | 0.6549 | Class2 | 0.622759932 | Class2 | 1 | 1 | 1 |
| JJA 003 | Class2 | 0.85076 | Class2 | 0.4305 | Class2 | 0.999953103 | Class2 | 1 | 1 | 1 |
| JJA 004 | Class2 | 1.2383 | Class2 | 0.7452 | Class2 | 0.999991482 | Class2 | 1 | 1 | 1 |
| JJA 005 | Class1 | −0.8258 | Class1 | 0.9692 | Class1 | 0.999597058 | Class1 | 1 | 1 | 1 |
| JJA 006 | Class2 | 1.13162 | Class2 | 1 | Class2 | 0.998562609 | Class2 | 1 | 1 | 1 |
| JJA 007 | Class1 | −1.03258 | Class1 | 0.9948 | Class1 | 0.999991148 | Class1 | 1 | 1 | 1 |
| JJA 008 | Class2 | 0.124333 | Class2 | 0.0137 | Class2 | 0.778526924 | Class2 | 1 | 1 | 1 |
| JJA 009 | Class1 | −0.78593 | Class1 | 0.7936 | Class1 | 0.993347415 | Class1 | 1 | 1 | 1 |
| JJA 010 | Class1 | −1.16291 | Class1 | 0.642 | Class1 | 0.725668259 | Class1 | 1 | 1 | 1 |
| JJA 011 | Class2 | 0.768558 | Class2 | 0.9391 | Class2 | 0.986079137 | Class2 | 1 | 1 | 1 |
| JJA 012a | Class2 | 0.481044 | Class2 | 0.6832 | Class2 | 0.972966955 | Class2 | 1 | 1 | 1 |
| JJA 013 | Class1 | −0.910024 | Class1 | 0.9937 | Class1 | 0.999882951 | Class1 | 1 | 1 | 1 |
| JJA 014 | Class1 | −1.20508 | Class1 | 0.9477 | Class1 | 0.999401721 | Class1 | 1 | 1 | 1 |
| JJA 015a | Class1 | −0.892323 | Class1 | 0.8958 | Class1 | 0.999556655 | Class1 | 1 | 1 | 1 |
| JJA 016A | Class2 | 0.407103 | Class2 | 0.5559 | Class2 | 0.999119863 | Class2 | 1 | 1 | 1 |
| JJA 017a | Class1 | −0.7893 | Class1 | 0.8209 | Class1 | 0.998501426 | Class1 | 1 | 1 | 1 |
| JJA 018t | Class2 | 0.824545 | Class2 | 0.6906 | Class2 | 0.998112235 | Class2 | 1 | 1 | 1 |
| JJA 019a | Class2 | 1.31672 | Class2 | 0.9909 | Class2 | 0.999962939 | Class2 | 1 | 1 | 1 |
| JJA 020a | Class1 | −0.30034 | Class1 | 0.2046 | Class1 | 0.781444752 | Class1 | 1 | 1 | 1 |
| JJA 021a | Class1 | −0.991805 | Class1 | 0.8063 | Class1 | 0.999713914 | Class1 | 1 | 1 | 1 |
| JJA 022a | Class2 | 0.613415 | Class2 | 0.0317 | Class2 | 0.743712066 | Class2 | 1 | 1 | 1 |
| JJA 023a | Class2 | 1.18035 | Class2 | 1 | Class2 | 0.998848027 | Class2 | 1 | 1 | 1 |
| JJA 024b | Class1 | −0.507471 | Class1 | 0.1094 | Class2 | 0.524593527 | Class1 | 1 | 0 | 0 |
| JJA 025a | Class1 | −1.52355 | Class1 | 0.9423 | Class1 | 0.999931074 | Class1 | 1 | 1 | 1 |
| JJA 026a | Class1 | −1.32137 | Class1 | 0.829 | Class1 | 0.999863071 | Class1 | 1 | 1 | 1 |
| JJA 027a | Class2 | 0.93128 | Class2 | 0.8051 | Class2 | 0.999159483 | Class2 | 1 | 1 | 1 |
| JJA 028a | Class2 | 0.36714 | Class2 | 0.9155 | Class2 | 0.934025713 | Class2 | 1 | 1 | 1 |
| JJA 029a | Class1 | −0.211109 | Class1 | 0.3092 | Class1 | 0.981267847 | Class1 | 1 | 1 | 1 |
| JJA 030a | Class1 | −0.741614 | Class1 | 0.9531 | Class1 | 0.999230128 | Class1 | 1 | 1 | 1 |
| JJA 031a | Class1 | −0.755264 | Class1 | 0.8867 | Class1 | 0.999649928 | Class1 | 1 | 1 | 1 |
| JJA 032a | Class1 | −0.936218 | Class1 | 0.867 | Class1 | 0.99817563 | Class1 | 1 | 1 | 1 |
| JJA 033a | Class1 | −0.681095 | Class1 | 0.6364 | Class1 | 0.87631126 | Class1 | 1 | 1 | 1 |
| JJA 034a | Class2 | 0.901018 | Class2 | 0.6149 | Class2 | 0.992954456 | Class2 | 1 | 1 | 1 |
| JJA 035a | Class1 | −0.847147 | Class1 | 0.7344 | Class1 | 0.999651952 | Class1 | 1 | 1 | 1 |
| JJA 036a | Class1 | −0.859055 | Class1 | 0.9805 | Class1 | 0.99897703 | Class1 | 1 | 1 | 1 |
| JJA 037a | Class1 | −0.746519 | Class1 | 1 | Class1 | 0.991943724 | Class1 | 1 | 1 | 1 |
| JJA 040b | Class2 | 1.1984 | Class2 | 0.9819 | Class2 | 0.999940814 | Class2 | 1 | 1 | 1 |
| JJA 041a | Class2 | 0.459054 | Class2 | 0.3118 | Class2 | 0.87827371 | Class2 | 1 | 1 | 1 |
| JJA 042a | Class1 | −1.13762 | Class1 | 0.7731 | Class1 | 0.986642299 | Class1 | 1 | 1 | 1 |
| JJA 043a | Class1 | −1.11328 | Class1 | 0.6349 | Class1 | 0.998818065 | Class1 | 1 | 1 | 1 |
| JJA 044 | Class2 | 0.783144 | Class2 | 0.4813 | Class2 | 0.884470798 | Class2 | 1 | 1 | 1 |
| JJA 045b | Class1 | −0.841891 | Class1 | 0.544 | Class1 | 0.996486274 | Class1 | 1 | 1 | 1 |
| JJA 046b | Class2 | 1.46445 | Class2 | 0.7964 | Class2 | 0.918758177 | Class2 | 1 | 1 | 1 |
| JJA 047 | Class1 | −0.683391 | Class1 | 0.9552 | Class1 | 0.999905196 | Class1 | 1 | 1 | 1 |

TABLE 8-continued

| Sample | SVM | Discriminant | WV | Confidence | PAM | PAM Prob | RDA | WV v SVM | PAM v SVM | RDA v SVM |
|---|---|---|---|---|---|---|---|---|---|---|
| JJA 048b | Class1 | −0.225559 | Class1 | 0.5708 | Class1 | 0.915966223 | Class1 | 1 | 1 | 1 |
| JJA 049a | Class1 | −0.923091 | Class1 | 0.7921 | Class1 | 0.99986157 | Class1 | 1 | 1 | 1 |
| JJA 050 | Class1 | −0.638053 | Class1 | 0.5451 | Class1 | 0.9870794 | Class1 | 1 | 1 | 1 |
| JJA 051a | Class1 | −0.847693 | Class1 | 0.9175 | Class1 | 0.824250216 | Class1 | 1 | 1 | 1 |
| JJA 052a | Class1 | −0.440794 | Class1 | 0.4157 | Class2 | 0.73152678 | Class2 | 1 | 0 | 0 |
| JJA 053a | Class1 | −0.791461 | Class1 | 0.9468 | Class1 | 0.788974304 | Class1 | 1 | 1 | 1 |
| JJA 054a | Class1 | −1.04466 | Class1 | 0.9535 | Class1 | 0.896444252 | Class1 | 1 | 1 | 1 |
| JJA 055a | Class1 | −0.433967 | Class1 | 0.7231 | Class1 | 0.862833264 | Class1 | 1 | 1 | 1 |
| JJA 056a | Class1 | −1.12812 | Class1 | 0.9494 | Class1 | 0.696641468 | Class1 | 1 | 1 | 1 |
| JJA 057a | Class2 | 0.987222 | Class2 | 1 | Class2 | 0.781384215 | Class2 | 1 | 1 | 1 |
| JJA 058a | Class2 | 0.961021 | Class2 | 0.4903 | Class2 | 0.838904623 | Class2 | 1 | 1 | 1 |
| JJA 059* | Class2 | 0.467496 | Class2 | 0.3669 | Class2 | 0.802294063 | Class1 | 1 | 1 | 0 |
| JJA 060a | Class2 | 1.06132 | Class2 | 0.9921 | Class2 | 0.798935341 | Class2 | 1 | 1 | 1 |
| JJA 061a | Class1 | −1.19426 | Class1 | 0.8818 | Class1 | 0.805587756 | Class1 | 1 | 1 | 1 |
| JJA 062b | Class2 | 0.882985 | Class2 | 0.761 | Class2 | 0.883932367 | Class2 | 1 | 1 | 1 |
| JJA 063a | Class1 | −0.133479 | Class1 | 0.022 | Class2 | 0.810377533 | Class2 | 1 | 0 | 0 |
| JJA 064a | Class1 | −1.20317 | Class1 | 0.8752 | Class2 | 0.727569279 | Class1 | 1 | 0 | 1 |
| JJA 065a | Class1 | −0.601065 | Class1 | 0.3456 | Class2 | 0.732672845 | Class1 | 1 | 0 | 1 |
| JJA 066a | Class2 | 0.178227 | Class2 | 0.0902 | Class1 | 0.881782547 | Class1 | 1 | 0 | 0 |
| JJA 067a | Class1 | −0.672217 | Class1 | 0.6398 | Class1 | 0.809340567 | Class1 | 1 | 1 | 1 |
| JJA 068a | Class1 | −0.635584 | Class1 | 0.6984 | Class1 | 0.906620334 | Class1 | 1 | 1 | 1 |
| JJA 069a | Class2 | 1.13878 | Class2 | 0.86 | Class2 | 0.829357777 | Class2 | 1 | 1 | 1 |
| JJA 070a | Class1 | −0.715419 | Class1 | 0.9406 | Class1 | 0.63296462 | Class1 | 1 | 1 | 1 |
| JJA 071a | Class1 | −0.796326 | Class1 | 0.969 | Class1 | 0.822343507 | Class1 | 1 | 1 | 1 |
| JJA 072a | Class1 | −1.26894 | Class1 | 0.9752 | Class1 | 0.756517327 | Class1 | 1 | 1 | 1 |
| JJA 073a | Class1 | −1.05558 | Class1 | 0.9348 | Class1 | 0.848777946 | Class1 | 1 | 1 | 1 |
| JJA 074a | Class2 | 0.60299 | Class2 | 0.5529 | Class2 | 0.92392566 | Class2 | 1 | 1 | 1 |
| JJA 075a | Class1 | −0.920513 | Class1 | 0.8222 | Class1 | 0.753787322 | Class1 | 1 | 1 | 1 |

TABLE 9

| Sample | SVM | Discriminant | WV | Confidence | PAM | PAM Prob | RDA | Wv v. SVM | PAM v SVM | RDA v SVM |
|---|---|---|---|---|---|---|---|---|---|---|
| NB 001 | Class2 | 0.960419 | Class2 | 0.7698 | Class2 | 0.998796031 | Class2 | 1 | 1 | 1 |
| NB 002 | Class1 | −0.253292 | Class1 | 0.3795 | Class1 | 0.933179497 | Class1 | 1 | 1 | 1 |
| NB 003 | Class2 | 1.69707 | Class2 | 1 | Class2 | 0.999863184 | Class2 | 1 | 1 | 1 |
| NB 004 | Class2 | 1.32803 | Class2 | 0.9601 | Class2 | 0.999966807 | Class2 | 1 | 1 | 1 |
| NB 005 | Class2 | 0.862793 | Class2 | 0.8791 | Class2 | 0.983414372 | Class2 | 1 | 1 | 1 |
| NB 006 | Class1 | −0.37904 | Class1 | 0.5401 | Class1 | 0.958364588 | Class1 | 1 | 1 | 1 |
| NB 007 | Class1 | −1.09263 | Class1 | 1 | Class1 | 0.999630332 | Class1 | 1 | 1 | 1 |
| NB 008 | Class1 | −0.388787 | Class1 | 0.5523 | Class1 | 0.999733038 | Class1 | 1 | 1 | 1 |
| NB 009 | Class1 | −0.937795 | Class1 | 0.6911 | Class1 | 0.992573275 | Class1 | 1 | 1 | 1 |
| NB 011 | Class2 | 0.518105 | Class2 | 0.4237 | Class2 | 0.972635362 | Class2 | 1 | 1 | 1 |
| NB 012 | Class2 | 0.381222 | Class2 | 0.3808 | Class2 | 0.905967179 | Class2 | 1 | 1 | 1 |
| NB 013 | Class2 | 0.74011 | Class2 | 0.5388 | Class2 | 0.990659998 | Class2 | 1 | 1 | 1 |
| NB 016 | Class2 | 1.27205 | Class2 | 0.7963 | Class2 | 0.999997211 | Class2 | 1 | 1 | 1 |
| NB 019 | Class2 | 0.626384 | Class2 | 0.5093 | Class2 | 0.949003606 | Class2 | 1 | 1 | 1 |
| NB 020 | Class1 | −0.867317 | Class1 | 0.9249 | Class1 | 0.999826316 | Class1 | 1 | 1 | 1 |
| NB 021 | Class2 | 0.607531 | Class2 | 0.4466 | Class2 | 0.983063147 | Class2 | 1 | 1 | 1 |
| NB 022 | Class1 | −0.650893 | Class1 | 0.6983 | Class1 | 0.999297708 | Class1 | 1 | 1 | 1 |
| NB 025 | Class1 | −0.898559 | Class1 | 0.973 | Class1 | 0.999946763 | Class1 | 1 | 1 | 1 |
| NB 026 | Class1 | −0.767198 | Class1 | 0.8428 | Class1 | 0.999377341 | Class1 | 1 | 1 | 1 |
| NB 027 | Class1 | −0.886666 | Class1 | 0.9388 | Class1 | 0.99990777 | Class1 | 1 | 1 | 1 |
| NB 028 | Class2 | 0.912673 | Class2 | 1 | Class2 | 0.996758216 | Class2 | 1 | 1 | 1 |
| NB 029 | Class1 | −1.03266 | Class1 | 0.8826 | Class1 | 0.998822018 | Class1 | 1 | 1 | 1 |
| NB 031 | Class2 | 1.31224 | Class2 | 1 | Class2 | 0.999832819 | Class2 | 1 | 1 | 1 |
| NB 032 | Class2 | 0.854863 | Class2 | 1 | Class2 | 0.994101973 | Class2 | 1 | 1 | 1 |
| NB 033 | Class2 | 0.171352 | Class2 | 0.315 | Class2 | 0.997958689 | Class2 | 1 | 1 | 1 |
| NB 034 | Class2 | 0.88448 | Class2 | 0.6291 | Class2 | 0.999973247 | Class2 | 1 | 1 | 1 |
| NB 035 | Class2 | 1.17804 | Class2 | 1 | Class2 | 0.999698173 | Class2 | 1 | 1 | 1 |
| NB 036 | Class2 | 1.22081 | Class2 | 1 | Class2 | 0.999759489 | Class2 | 1 | 1 | 1 |
| NB 037 | Class2 | 1.46538 | Class2 | 0.8842 | Class2 | 0.999409155 | Class2 | 1 | 1 | 1 |
| NB 038 | Class1 | −1.00294 | Class1 | 0.9503 | Class1 | 0.999679393 | Class1 | 1 | 1 | 1 |
| NB 039 | Class2 | 0.865438 | Class2 | 0.7387 | Class2 | 0.983846425 | Class2 | 1 | 1 | 1 |
| NB 042 | Class2 | 0.678319 | Class2 | 0.7241 | Class2 | 0.990905293 | Class2 | 1 | 1 | 1 |
| NB 043 | Class1 | −0.99871 | Class1 | 0.9205 | Class1 | 0.999263399 | Class1 | 1 | 1 | 1 |
| NB 044A | Class1 | −0.244319 | Class1 | 0.4027 | Class2 | 0.855069025 | Class2 | 1 | 0 | 0 |
| NB 044B | Class2 | 0.507911 | Class2 | 0.9556 | Class2 | 0.990376255 | Class2 | 1 | 1 | 1 |
| NB 045 | Class2 | 0.852048 | Class2 | 0.4097 | Class2 | 0.999946135 | Class2 | 1 | 1 | 1 |
| NB 046 | Class1 | −0.548455 | Class1 | 0.5518 | Class1 | 0.961862856 | Class1 | 1 | 1 | 1 |
| NB 047 | Class2 | 1.05675 | Class2 | 0.8568 | Class2 | 0.999894505 | Class2 | 1 | 1 | 1 |
| NB 048 | Class2 | 0.876976 | Class2 | 1 | Class2 | 0.998160264 | Class2 | 1 | 1 | 1 |
| NB 049 | Class2 | 0.303263 | Class2 | 0.5224 | Class2 | 0.905602908 | Class2 | 1 | 1 | 1 |

TABLE 9-continued

| Sample | SVM | Discriminant | WV | Confidence | PAM | PAM Prob | RDA | Wv v. SVM | PAM v SVM | RDA v SVM |
|---|---|---|---|---|---|---|---|---|---|---|
| NB 050 | Class1 | −0.859379 | Class1 | 0.9352 | Class1 | 0.997288147 | Class1 | 1 | 1 | 1 |
| NB 051 | Class1 | −0.591264 | Class1 | 0.5518 | Class1 | 0.983792273 | Class1 | 1 | 1 | 1 |
| NB 052 | Class1 | −0.646411 | Class1 | 0.8503 | Class1 | 0.992451996 | Class1 | 1 | 1 | 1 |
| NB 053 | Class1 | −0.385843 | Class1 | 0.6714 | Class1 | 0.999259317 | Class1 | 1 | 1 | 1 |
| NB 055 | Class1 | −0.921191 | Class1 | 0.9127 | Class1 | 0.998615026 | Class1 | 1 | 1 | 1 |
| NB 056 | Class2 | 0.777825 | Class2 | 0.9173 | Class2 | 0.998750013 | Class2 | 1 | 1 | 1 |
| NB 057 | Class1 | −0.425043 | Class1 | 0.4672 | Class1 | 0.983761331 | Class1 | 1 | 1 | 1 |
| NB 058 | Class2 | 0.263717 | Class2 | 0.2719 | Class2 | 0.685714589 | Class2 | 1 | 1 | 1 |
| NB 059 | Class1 | −0.275363 | Class1 | 0.4707 | Class1 | 0.992868587 | Class1 | 1 | 1 | 1 |
| NB 061 | Class1 | −0.635098 | Class1 | 0.7821 | Class1 | 0.985794635 | Class1 | 1 | 1 | 1 |
| NB 062 | Class2 | 0.639771 | Class2 | 0.7548 | Class2 | 0.969168395 | Class2 | 1 | 1 | 1 |
| NB 063 | Class1 | −0.799788 | Class1 | 0.6424 | Class1 | 0.98533142 | Class1 | 1 | 1 | 1 |
| NB 064 | Class1 | −1.16072 | Class1 | 0.9905 | Class1 | 0.999493868 | Class1 | 1 | 1 | 1 |
| NB 065 | Class2 | 0.853104 | Class2 | 1 | Class2 | 0.992058185 | Class2 | 1 | 1 | 1 |
| NB 066 | Class2 | 0.922212 | Class2 | 1 | Class2 | 0.998514497 | Class2 | 1 | 1 | 1 |
| NB 067A | Class1 | −0.989357 | Class1 | 0.967 | Class1 | 0.999884235 | Class1 | 1 | 1 | 1 |
| NB 068 | Class2 | 0.749477 | Class2 | 0.9595 | Class2 | 0.993155294 | Class2 | 1 | 1 | 1 |
| NB 069 | Class1 | −0.50009 | Class1 | 0.8165 | Class1 | 0.944999138 | Class1 | 1 | 1 | 1 |
| NB 070 | Class1 | −1.03506 | Class1 | 0.923 | Class1 | 0.998875958 | Class1 | 1 | 1 | 1 |
| NB 071 | Class2 | 1.16291 | Class2 | 1 | Class2 | 0.999597924 | Class2 | 1 | 1 | 1 |
| NB 072 | Class1 | −0.738465 | Class1 | 0.9125 | Class1 | 0.992933099 | Class1 | 1 | 1 | 1 |
| NB 073 | Class2 | 1.51662 | Class2 | 1 | Class2 | 0.999974605 | Class2 | 1 | 1 | 1 |
| NB 074 | Class2 | 0.937633 | Class2 | 0.9762 | Class2 | 0.999052541 | Class2 | 1 | 1 | 1 |
| NB 075 | Class2 | 0.0769161 | Class1 | 0.1715 | Class1 | 0.879917918 | Class1 | 0 | 0 | 0 |
| NB 076 | Class1 | −0.910177 | Class1 | 0.487 | Class1 | 0.894517507 | Class1 | 1 | 1 | 1 |
| NB 078 | Class1 | −0.909596 | Class1 | 0.9853 | Class1 | 0.999946234 | Class1 | 1 | 1 | 1 |
| NB 081 | Class2 | 0.00498798 | Class1 | 0.0937 | Class2 | 0.735674662 | Class2 | 0 | 1 | 1 |
| NB 082 post | Class2 | 0.926065 | Class2 | 0.822 | Class2 | 0.995736019 | Class2 | 1 | 1 | 1 |
| NB 082A | Class2 | 0.579883 | Class2 | 0.9524 | Class2 | 0.989536758 | Class2 | 1 | 1 | 1 |
| NB 085 | Class2 | 0.0173483 | Class1 | 0.1016 | Class2 | 0.50434202 | Class2 | 0 | 1 | 1 |
| NB 086 | Class2 | 1.34949 | Class2 | 1 | Class2 | 0.99996361 | Class2 | 1 | 1 | 1 |
| NB 087 | Class2 | 1.09605 | Class2 | 1 | Class2 | 0.998900338 | Class2 | 1 | 1 | 1 |
| NB 089** | Class2 | 0.588579 | Class2 | 0.4274 | Class2 | 0.999008358 | Class2 | 1 | 1 | 1 |
| NB 090 | Class2 | 0.22548 | Class2 | 0.0705 | Class2 | 0.949381275 | Class2 | 1 | 1 | 1 |
| NB 091 | Class2 | 1.19526 | Class2 | 0.9515 | Class2 | 0.999963157 | Class2 | 1 | 1 | 1 |
| NB 092 | Class1 | −0.654492 | Class1 | 0.8734 | Class1 | 0.995346659 | Class1 | 1 | 1 | 1 |
| NB 093 | Class1 | −0.852299 | Class1 | 0.9121 | Class1 | 0.999478741 | Class1 | 1 | 1 | 1 |
| NB 094 | Class2 | 0.834943 | Class2 | 0.5367 | Class2 | 0.991354801 | Class2 | 1 | 1 | 1 |
| NB 096 | Class1 | −0.850806 | Class1 | 0.9121 | Class1 | 0.999928705 | Class1 | 1 | 1 | 1 |
| NB 097 | Class2 | 0.593952 | Class2 | 0.2078 | Class2 | 0.978481107 | Class2 | 1 | 1 | 1 |
| NB 098 | Class2 | 1.33821 | Class2 | 1 | Class2 | 0.999964276 | Class2 | 1 | 1 | 1 |
| NB 099 | Class1 | −1.05924 | Class1 | 0.8295 | Class1 | 0.999563238 | Class1 | 1 | 1 | 1 |
| NB 100 | Class1 | −1.18371 | Class1 | 0.7928 | Class1 | 0.9976735 | Class1 | 1 | 1 | 1 |
| NB 101 | Class1 | −0.656301 | Class1 | 0.8909 | Class1 | 0.998374852 | Class1 | 1 | 1 | 1 |
| NB 102 | Class1 | −0.910164 | Class1 | 0.7712 | Class1 | 0.997808723 | Class1 | 1 | 1 | 1 |
| NB 103 | Class1 | −0.84389 | Class1 | 0.9655 | Class1 | 0.996693591 | Class1 | 1 | 1 | 1 |
| NB 104 | Class1 | −0.20035 | Class1 | 0.2772 | Class1 | 0.985740548 | Class1 | 1 | 1 | 1 |
| NB 107 | Class1 | −0.908397 | Class1 | 0.9406 | Class1 | 0.999753344 | Class1 | 1 | 1 | 1 |
| NB 108 | Class1 | −0.902297 | Class1 | 0.9944 | Class1 | 0.999776518 | Class1 | 1 | 1 | 1 |
| NB 109 | Class1 | −1.03783 | Class1 | 0.8362 | Class1 | 0.999415069 | Class1 | 1 | 1 | 1 |
| NB 111 | Class1 | −0.955505 | Class1 | 0.5359 | Class1 | 0.952779382 | Class1 | 1 | 1 | 1 |
| NB 112 | Class1 | −0.969156 | Class1 | 0.6606 | Class1 | 0.981564998 | Class1 | 1 | 1 | 1 |
| NB 113 | Class1 | −0.923373 | Class1 | 0.9963 | Class1 | 0.999161058 | Class1 | 1 | 1 | 1 |
| NB 114 | Class1 | −0.564734 | Class1 | 0.1615 | Class1 | 0.743718949 | Class1 | 1 | 1 | 1 |
| NB 115 | Class1 | −1.20199 | Class1 | 1 | Class1 | 0.999954758 | Class1 | 1 | 1 | 1 |
| NB 116 | Class1 | −1.22422 | Class1 | 0.8845 | Class1 | 0.999968789 | Class1 | 1 | 1 | 1 |
| NB 117 | Class2 | 0.0741798 | Class2 | 0.1342 | Class2 | 0.955469856 | Class2 | 1 | 1 | 1 |
| NB 118* | Class1 | −0.550099 | Class1 | 0.4616 | Class2 | 0.938306408 | Class2 | 1 | 0 | 0 |
| NB 119 | Class1 | −0.838984 | Class1 | 0.9898 | Class1 | 0.999956644 | Class1 | 1 | 1 | 1 |
| NB 120 | Class1 | −0.793206 | Class1 | 0.9086 | Class1 | 0.999741717 | Class1 | 1 | 1 | 1 |
| NB 121 | Class2 | 0.850564 | Class2 | 0.8068 | Class2 | 0.994788595 | Class2 | 1 | 1 | 1 |
| NB 122 | Class1 | −0.738526 | Class1 | 0.8644 | Class1 | 0.999611744 | Class1 | 1 | 1 | 1 |
| NB 125 | Class1 | −0.709254 | Class1 | 0.9164 | Class1 | 0.999638333 | Class1 | 1 | 1 | 1 |
| NB 126 | Class1 | −0.773793 | Class1 | 0.8957 | Class1 | 0.99997402 | Class1 | 1 | 1 | 1 |
| NB 127 | Class2 | 1.50753 | Class2 | 1 | Class2 | 0.999975237 | Class2 | 1 | 1 | 1 |
| NB 128 | Class1 | −0.908214 | Class1 | 0.8049 | Class1 | 0.993646478 | Class1 | 1 | 1 | 1 |
| NB 129 | Class2 | 0.911665 | Class2 | 1 | Class2 | 0.998327936 | Class2 | 1 | 1 | 1 |
| NB 130 | Class2 | 1.21714 | Class2 | 1 | Class2 | 0.999927522 | Class2 | 1 | 1 | 1 |
| NB 132 A | Class2 | 0.294757 | Class2 | 0.176 | Class2 | 0.975930288 | Class2 | 1 | 1 | 1 |
| NB 132 B | Class1 | −0.908295 | Class1 | 0.7951 | Class1 | 0.994026023 | Class1 | 1 | 1 | 1 |
| NB 133 A | Class2 | 0.576505 | Class2 | 0.8919 | Class2 | 0.991440895 | Class2 | 1 | 1 | 1 |
| NB 133 B | Class2 | 0.884664 | Class2 | 1 | Class2 | 0.998646727 | Class2 | 1 | 1 | 1 |
| NB 134 | Class2 | 0.407353 | Class2 | 0.3507 | Class2 | 0.88818491 | Class2 | 1 | 1 | 1 |
| NB 135 | Class2 | 1.01598 | Class2 | 0.9837 | Class2 | 0.995952803 | Class2 | 1 | 1 | 1 |
| NB 136 | Class2 | 1.15437 | Class2 | 1 | Class2 | 0.999278229 | Class2 | 1 | 1 | 1 |
| NB 137 | Class2 | 0.378148 | Class2 | 0.7304 | Class2 | 0.856035012 | Class2 | 1 | 1 | 1 |
| NB 138 | Class2 | 0.0192144 | Class2 | 0.0051 | Class2 | 0.630786724 | Class2 | 1 | 1 | 1 |

TABLE 9-continued

| Sample | SVM | Discriminant | WV | Confidence | PAM | PAM Prob | RDA | Wv v. SVM | PAM v SVM | RDA v SVM |
|---|---|---|---|---|---|---|---|---|---|---|
| NB 139 | Class1 | −0.902041 | Class1 | 0.9335 | Class1 | 0.999558526 | Class1 | 1 | 1 | 1 |
| NB 140 | Class1 | −1.14887 | Class1 | 0.9773 | Class1 | 0.99967606 | Class1 | 1 | 1 | 1 |
| NB 142 | Class1 | −0.999116 | Class1 | 0.7726 | Class1 | 0.997697849 | Class1 | 1 | 1 | 1 |
| NB 143 | Class1 | −0.979782 | Class1 | 0.6881 | Class1 | 0.998645648 | Class1 | 1 | 1 | 1 |
| NB 144 | Class2 | 0.0560605 | Class2 | 0.0427 | Class2 | 0.954692359 | Class2 | 1 | 1 | 1 |
| NB 145 | Class1 | −0.795812 | Class1 | 0.8335 | Class1 | 0.999166373 | Class1 | 1 | 1 | 1 |
| NB 146 | Class1 | −0.484342 | Class1 | 0.7408 | Class1 | 0.999288263 | Class1 | 1 | 1 | 1 |
| NB 148 | Class1 | −1.09712 | Class1 | 0.9809 | Class1 | 0.999185163 | Class1 | 1 | 1 | 1 |
| NB 149 | Class1 | −0.888749 | Class1 | 0.7985 | Class1 | 0.995076271 | Class1 | 1 | 1 | 1 |
| NB 150 | Class1 | −0.976575 | Class1 | 0.9773 | Class1 | 0.999275438 | Class1 | 1 | 1 | 1 |
| NB 151 | Class1 | −1.06987 | Class1 | 0.995 | Class1 | 0.999944675 | Class1 | 1 | 1 | 1 |
| NB 152 | Class1 | −1.09499 | Class1 | 0.9094 | Class1 | 0.801627844 | Class1 | 1 | 1 | 1 |
| NB 153 | Class2 | 1.1334 | Class2 | 0.9891 | Class2 | 0.88373757 | Class2 | 1 | 1 | 1 |
| NB 154 | Class2 | 0.287674 | Class2 | 0.3706 | Class2 | 0.702928873 | Class2 | 1 | 1 | 1 |
| NB 155 | Class1 | −0.994347 | Class1 | 0.9972 | Class1 | 0.808699828 | Class1 | 1 | 1 | 1 |
| NB 156 | Class1 | −0.573379 | Class1 | 0.6289 | Class1 | 0.799263552 | Class1 | 1 | 1 | 1 |
| NB 157 | Class1 | −0.575431 | Class1 | 0.7529 | Class1 | 0.894358329 | Class1 | 1 | 1 | 1 |
| NB 158 | Class1 | −0.397711 | Class1 | 0.6704 | Class1 | 0.894394715 | Class1 | 1 | 1 | 1 |

Example 4

Risk Analysis from Ocular Melanoma Biopsy

Molecular data on 155 biopsied cases were developed prospectively on ocular melanoma collected at Washington University. Median follow-up for these cases is 14.4 months; longest follow-up is 5 years. Of the 155, 16 cases have reported metastatic disease (median f/u=14.6 mo), and 9 of the 16 have died as a result of their disease (median f/u=19.5 mo). 15 of the 16 cases showing metastatic spread were identified as "Class 2" tumors and one was identified as "Class 1". All four analytical algorithms tested gave the same results for these 16 tumors. FIG. 7A-D show the Kaplan-Meier Survival Analyses based on the most recent follow-up data for each of the four algorithms currently in use. The analytical algorithms used for this study are Support Vector Machine (SVM; Gist ver. 2.3), Weighted Voting (WV; part of the GenePattern Suite), Regularized Discriminant Analysis (RDA; on the R-platform), and Prediction Analysis of Microarrays (PAM; on the R-platform).

Figure 8:
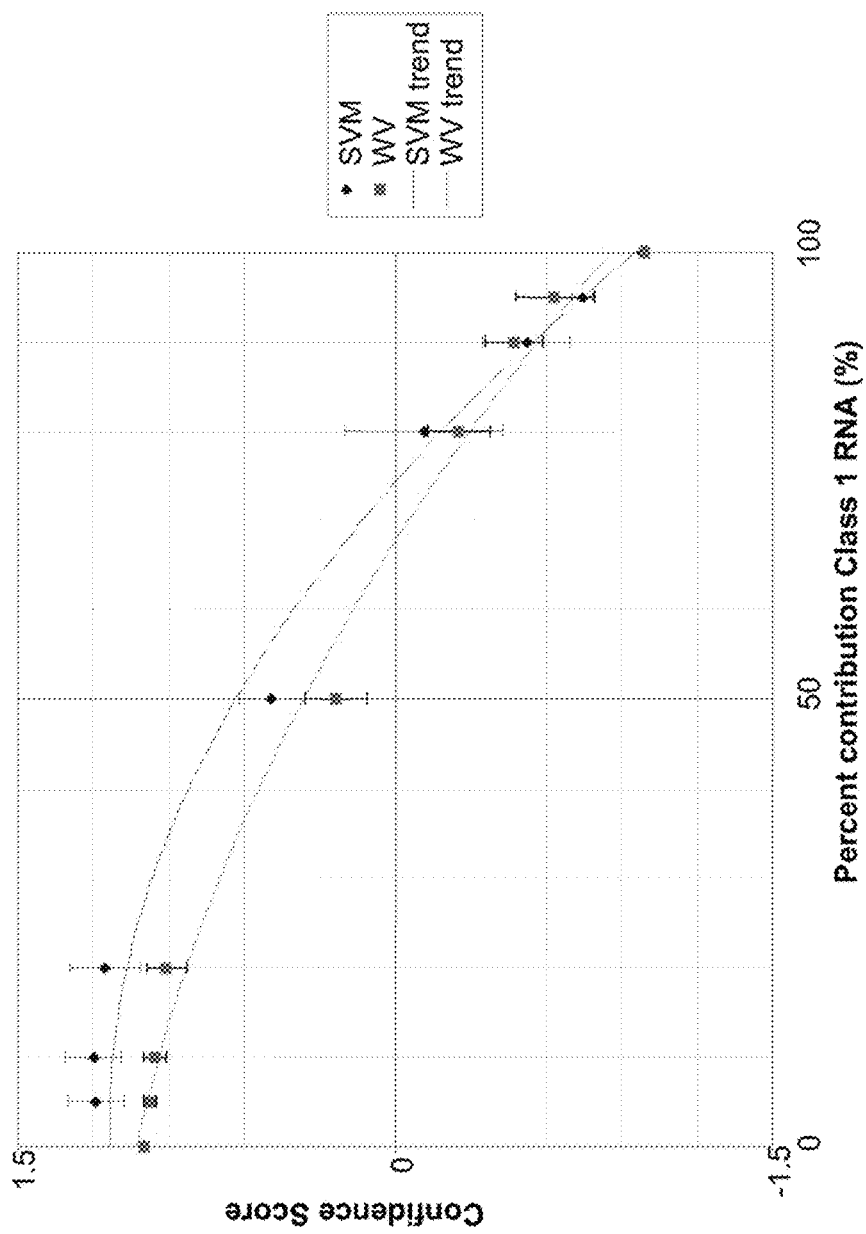
FIG. 8 depicts the results of an experiment in which RNA from three class 1 tumors and three class 2 tumors was admixed at various ratios to determine where the assay switches from calling a tumor class 1 to class 2. SVM and WV both detect the class 2 profile with as little as 25% RNA contributed from class 2 cells. This is thought to explain the very low rate of false negatives observed with this assay.

Ocular melanoma samples have been reported to yield less accurate predictive results when there is a high degree of heterogeneity of cells populating the tumor. This has been especially confounding in identifying chromosomal changes, such as monosomy 3, in mixed tumors. To see whether the molecular classification of the invention could identify potentially aggressive Class 2 cells in the context of heterogeneous tumor samples, RNA extracts from known Class 1 and Class 2 samples were combined in dilution series and then the mixed samples were analyzed. SVM and WV could identify tumors with Class 2 RNA contributions down to 20% and 30%, respectively, at acceptable confidence levels, while RDA became unconfident around 50% and PAM showed less confidence but higher sensitivity to any contribution of Class 2 RNA tested. (FIG. 8).

Example 5

Cutaneous Melanoma Risk Analysis

Figure 9:
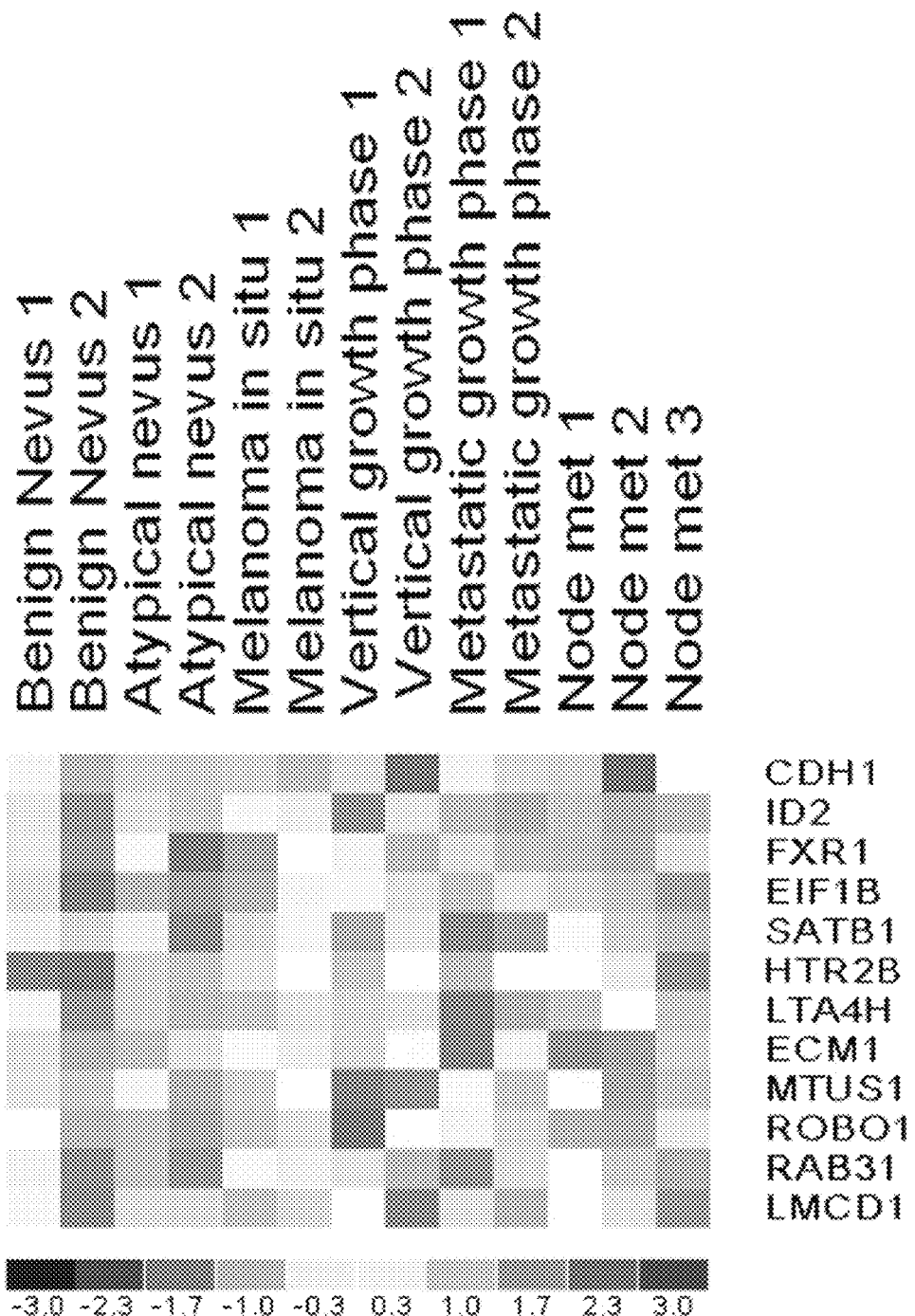
FIG. 9 depicts a heatmap in which the 12 discriminating genes are evaluated for expression in a published series of cutaneous melanocytic neoplasms ranging from low grade benign nevi, atypical nevi and melanoma in situ to high grade vertical growth phase, metastatic growth phase and lymph node metastatic tumors. The genes discriminated well between the low grade and high grade tumors. Red=upregulated, blue=downregulated.
Figure 10:
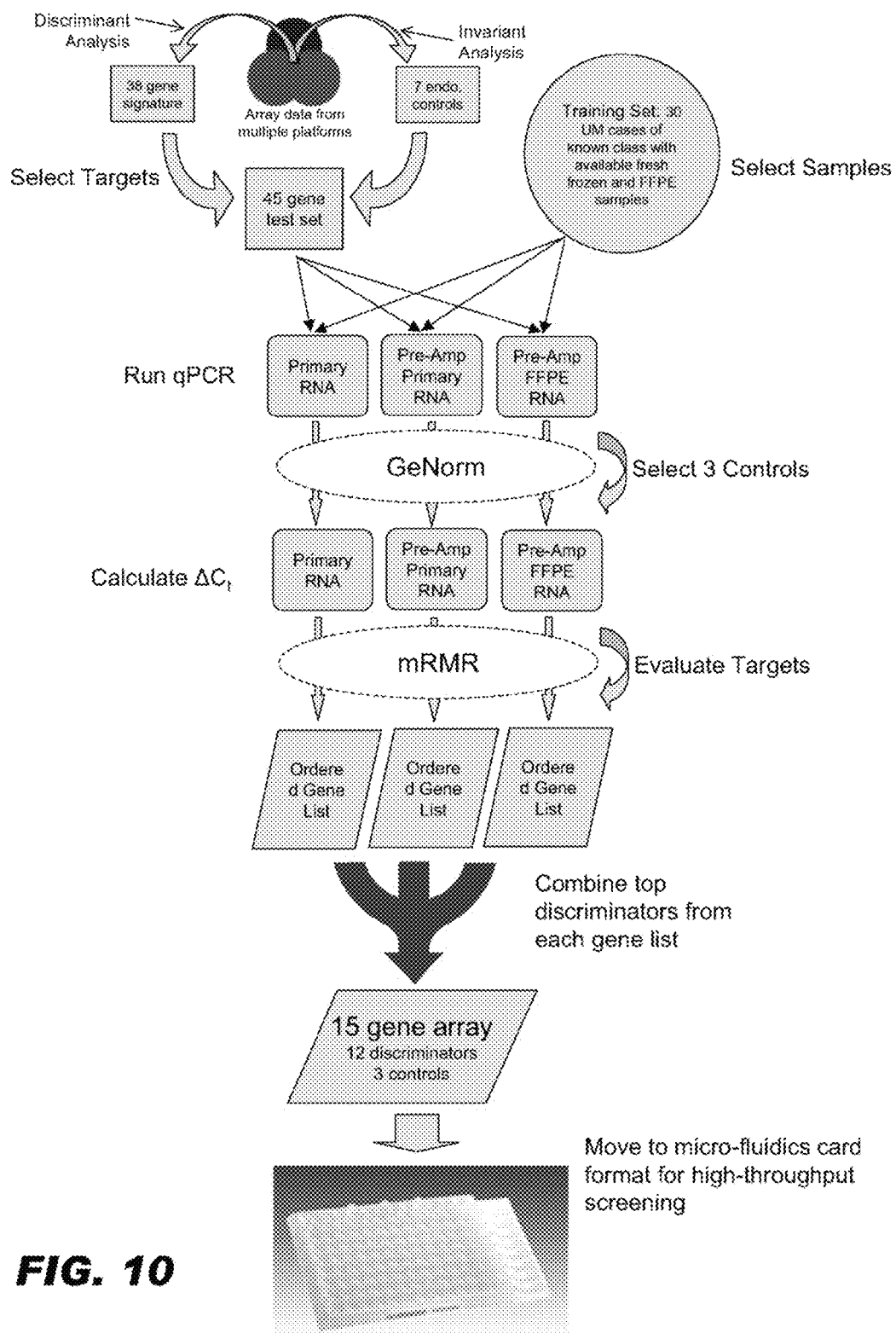
FIG. 10 depicts a flow chart of an assay protocol.

The nucleic acid sequence expression data from CDH1, ECM1, EIF1B, FXR1, HTR2B, ID2, LMCD1, LTA4H, MTUS1, RAB31, ROBO1, and SATB1 were used to classify the risk of metastasis in cutaneous melanoma samples. The data is shown in the heatmap illustrated in FIG. 9. Of thirteen samples tested, the expression data classified six samples as low risk. These samples correlated with low grade tumors with low risk for metastasis according to traditional histopathology. The expression data classified seven as high risk for metastasis, and these samples were identified as high grade primary tumors or actual metastastic tumors. Genes expressed at low levels are indicated by blue, and those highly expressed in red.

Example 6

Development of qPCR Assay

The metastatic spread of tumor cells from primary tumors to distant organs represents the source of most cancer mortalities. As such, identifying which primary tumors will metastasize, or have already, will have a greater impact on patient survival and the use of therapeutic anti-cancer agents than identifying oncogenes common to malignant and benign tumors. Uveal melanoma offers an unique opportunity to study metastatic spread to distant organs, since it can only spread hematogenously and almost half of uveal melanoma cases result in metastatic disease that is uniformly fatal. We have identified a gene expression profile that distinguishes uveal melanomas with the potential to metastasize from their less aggressive counterparts, and we have shown that this signature is the most accurate prognostic factor in predicting metastatic spread of uveal melanomas. Here we describe the translation of our microarray-based gene expression profiling to an inexpensive microfluidics platform based on simultaneously collecting the expressions of 15 genes by quantitative PCR (qPCR). We have validated the ability of our assay to classify accurately several large independent sets of uveal melanoma (UM) from around the globe, and have extended its use to primary tumor samples, needle biopsy samples, and formalin-fixed, paraffin embedded samples collected from different centers.

Results

Previously, we identified a gene expression signature comprising 51 targets that could accurately classify UM tumors. As part of that study, we showed that further analysis for minimum redundancy/maximum relevance (mRMR) could reduce the number of required genes in the signature to less than 10 while maintaining accurate classification of tumor samples. This included sample RNA isolated from fresh frozen tumor tissue, formalin-fixed paraffin embedded (FFPE) tumor tissue and fine-needle aspirate biopsies (FNAB). For this study, we combined the discriminating gene lists from our published microarray data collected on the Affymetrix U133A and U133Av2 GeneChips® and the Illumina Ref8 Beadchip® to identify 38 discriminating genes (15 upregulated in Class 2; 23 downregulated in Class 2) that represented the best candidates for qPCR, based on their ability to discriminate molecular class across different microarray platforms. To identify genes that displayed minimal changes in expression among all of the samples analyzed, we used GeNorm software on the microarray data collected from the Affymetrix U133A genechips and chose the seven genes that demonstrated the least variance. Predesigned TaqMan® Gene Expression Assays were then selected for each of the 38 discriminating genes and each of the seven endogenous control genes.

To determine the predictive value of each of the qPCR assays, we first selected 21 UM cases that matched the following criteria: available fresh frozen tumor tissue, available FFPE tumor tissue blocks, and known molecular class based on gene expression microarray data. We first analyzed the activities of the 45 Assays in our 21 primary UM tissue samples. We then identified three genes, MRPS21, RBM23, and SAP130, out of the seven potential endogenous controls that showed the most stability among test samples as determined by geNorm. The geometric means of the expression of these genes were calculated for each sample and used as a normalizer for calculating $\Delta$Ct values for the 38 target Assays. Direct comparison of expressions of each target gene among the 21 samples identified 16 targets whose expression patterns did not correlate with sample class. These 16 Assays were not included for the remainder of the study.

We expected the RNA extracted from FFPE samples to be of lower quality than our primary samples due to degradation. Likewise, we expected the RNA extracted from FNAB samples to be of lower quantity than our primary samples due to the limitations of the procedure. To overcome both of these potential problems, cDNAs generated from our low quality FFPE samples and low quantity Pre-Amp samples would need to be pre-amplified for 14 cycles using a pool of all of the probes that were to be tested in the subsequent qPCR assays. To identify those genes of the 22 discriminators that potentially could be used on these samples, we diluted our training set RNA samples to less than 100 ng per sample, and then pre-amplified these samples using the Applied Biosystems Pre-Amp protocol. Pre-amplified training set samples were then analyzed by qPCR using our set of 22 genes. Following this, RNA was extracted from FFPE blocks corresponding to the training set samples and analyzed with our 22 gene array. Of the 22 FFPE samples tested, 19 yielded material of sufficient quality and quantity to test, and two of these had multiple targets fail such that they could not be analyzed accurately.

After the 22 discriminating genes were run using the three UM endogenous controls on each set of primary, pre-amplified and FFPE "training set" samples, the resulting expression data were analyzed by Statistical Analysis of Microarrays (SAM), Weighted Voting (WV) and mRMR to identify the subset of genes that could properly classify each of the groups of the training set samples. 12 genes were identified that could discriminate tumor class in the primary, pre-amplified, and FFPE sample sets, and these were then paired with the three endogenous controls to form a fifteen (15) gene array that could be transitioned onto a TaqMan microfluidics card. (FIG. 11) Once these cards were received, the training sets were re-run on the microfluidics cards to confirm the integrity of the new platform. Expression results from each group of sample types were then used to constitute three "training sets" that were used for all subsequent analyses of unknown samples.

We have collected 383 FNAB samples from several centers around the nation and analyzed them on the TaqMan array platform. Of the 383 samples analyzed for this study, 29 (7.6%) had one or more probes show expression below detectable limits, and of these only 16 (3.1%) had two or more undetectable targets. We used these unknown samples to determine the best algorithm for classifying individual tumors with our new platform. Four independent algorithms that have shown great recent interest within the microarray community for classifying datasets are Weighted Voting (WV), Support Vector Machine (SVM), Prediction Analysis for Microarrays (PAM) and Regularized Discriminant Analysis (RDA). We performed tumor classification analysis using each of these algorithms to compare the strengths of each algorithm at predicting metastatic spread based on the TaqMan array data. Of the 383 samples tested on our platform, 34 (8.9%) yielded conflicting classification results among the four algorithms tested. Similarly, an independent set of primary UM samples were tested and out of 26 samples, 2 (7.7%) showed discordance among the four algorithms. In all samples giving discordant results, the confidence scores of one or more of the algorithms were below acceptable limits for significant classification. Of the 12 samples with two or more failed targets, 10 (83.3%) gave discordant results depending upon how the missing values were handled.

Many tumor samples are heterogeneous regarding the collection of tumor and normal cells. Further, karyotypic studies of UM tumors have identified varying degrees of heterogeneity in the populations of cancer cells comprising the tumor. Because sample heterogeneity is often cited as a confounding factor in tumor characterization in UM, we designed an experiment to test the effects of sample heterogeneity on our assay. We selected three class 1 and three class 2 tumors from our training set and prepared three series of samples, in which RNA extracted from a class 2 tumor was mixed with RNA extracted from a class 1 tumor at different dilutions. These samples were processed to cDNA and assayed on the microfluidics array. Each of the four algorithms could classify accurately the pure samples, and remarkably, all four classified as class 2 samples containing less than 50% contribution of class 2 cells.

Preparation of RNA Samples.

All studies were approved by the Human Studies Committee at Washington University, and informed consent was obtained from each subject. Fine needle biopsies were performed using a 25-gauge needle on uveal melanomas prior to radiotherapy as previously described. Fine needle aspirates were divided into samples for cytologic diagnosis and molecular analysis. The samples for RNA analysis were expelled into an empty RNase-free tube in the operating room. The empty syringe was filled with 200 µl of extraction buffer (XB) from the PicoPure® RNA isolation kit (Molecular Devices, Sunnyvale, Calif.), which was then transferred to the same tube to collect any additional tumor cells lodged in the needle hub. The collection tube was then snap frozen in liquid nitrogen in the operating room prior to transportation. On arrival in the laboratory, the samples were logged and the contents of the tubes were incubated at 42° C. for 30 minutes. RNA was isolated using the PicoPure® kit (including the optional DNase step), which yielded about 100 ng to 1.5 µg total RNA per aspirate using the NanoDrop 1000 system (Wilmington, Del.). For fresh tumors, total RNA was obtained using TRIzol (Invitrogen), including the optional isolation step (Appendix B), which is performed to rid the sample of any insoluble material, and purified using RNeasy kits (Qiagen) according to manufacturers' instructions. RNA quality was assessed on the NanoDrop 1000 system. For formalin-fixed paraffin-embedded (FFPE) samples, five 20 µm sections were obtained from tissue blocks, and tumor tissue was dissected away from surrounding normal material. Total RNA was isolated using the RecoverAll™ Total Nucleic Acid Isolation kit (Ambion) following the manufacturer's protocol. RNA samples were stored at −80° C. until needed. For specimens sent to St. Louis from other centers, tubes were placed on dry ice and mailed by overnight courier, after which they were incubated at 42° C. for 30 minutes and handled as described for the other biopsy samples. No RNA degradation was observed for these samples.

Gene Expression Profiling.

Gene expression profiling was performed previously on one or more of the following microarray platforms: Affymetrix U133A GeneChip® (28 cases), U133Av2 GeneChip® (11 cases), and Illumina Ref8 Beadchip® array (26 cases). Analysis of these profiles, including identification of discriminating gene lists, has been published elsewhere.

Real-Time PCR Analysis.

All RNA samples were converted to cDNA using the High Capacity cDNA Reverse Transcription kit from Applied Biosystems and following the manufacturer's protocol. For samples of sufficient quantity, 1 µg of RNA was converted to cDNA. For less concentrated samples, for instance RNA collected from FNAB or FFPE samples, the entire 10 µL of RNA was used. Complete conversion of RNA to cDNA was assumed. For samples of low RNA quantity (FNAB) or quality (FFPE), cDNA was amplified for 14 cycles with pooled TaqMan Gene Expression Assays and TaqMan Pre-Amp Master Mix following manufacturer's protocol. Pre-amplified samples were diluted 20-fold into sterile TE buffer and stored at −20° C. until needed. Expression of mRNA for individual genes was quantified using the 7900HT Real-Time PCR System with Applied Biosystems TaqMan® Gene Expression Assays and Gene Expression Master Mix following manufacturer's protocol. For samples of very low RNA quantity (FNAB) or quality (FFPE), cDNA was amplified for 14 cycles with pooled TaqMan Gene Expression Assays and TaqMan Pre-Amp Master Mix following manufacturer's protocol prior to gene expression analysis. TaqMan Microfluidics Expression Arrays were custom ordered to include our 12 class discriminating genes, 3 endogenous control genes, and 18S rRNA as a manufacturers control, so that each assay would be run in triplicate for each sample loaded. Ct values were calculated using the manufacturer's software, and mean Ct values were calculated for all triplicate sets. ΔCt values were calculated by subtracting the mean Ct of each discriminating gene from the geometric mean of the mean Ct values of the three endogenous control genes (Vandesompele J, et al. 2002 Genome Biology).

Biostatistical Analyses.

Selection of endogenous control genes was performed using geNorm software (http://medgen.ugent.be/genorm), which identifies stable combinations of genes from a pool of potential controls. Rank order of discriminating probesets to be entered stepwise into the predictive test for cross validation were determined with mRMR software (http://miracle.lbl.gov/proj/mRMR/), using mutual information difference as the feature selection scheme and +/−0.5 standard deviations as a threshold for discretizing expression values. Significance of discriminating probeset overlap was determined using hypergeometric probability using the PROBHYBR function of SAS 9.0 statistical software as previously described. Molecular class was predicted by entering the 12 ΔCt profile of each sample into the Gist 2.3 Support Vector Machine algorithm (http://bioinformatics.ubc.ca/svm), which had been trained with the profiles of 30 cases of UM with independently verified molecular class and known outcome. Discriminant scores were calculated by the software. Kaplan-Meier analysis was used to assess time-dependent association with metastasis for GEP class. Sensitivity, specificity, likelihood ratios, and predictive values were assessed for all clinical, pathologic and molecular factors. All statistical analyses were performed using MedCalc software, version 9.0.0.1 (http://www.medcalc.be).

Discussion

We have previously identified a gene expression profile that accurately predicts metastatic spread in uveal melanoma. We have also shown that samples collected form fine-needle aspirate biopsies and formalin-fixed paraffin-embedded samples yield sufficient material to classify using our gene expression profile. Here we detail the transfer of this prognostic tool to a high-throughput microfluidics array that maintains the prognostic accuracy of the origin profile, while making the assay available to clinical laboratories unequipped to perform complex microarray experiments. The need for an accurate, inexpensive, widely available prognostic test for identifying the risk of metastasis in patients with UM is paramount to controlling this deadly disease.

What is claimed is:

1. A method of detecting expression levels of nucleic acid sequences in a melanoma tumor in a subject, the method comprising contacting a tumor sample obtained from the subject with a nucleic acid array consisting of nucleic acid sequences that hybridize specifically to at least eight nucleic acid nucleic acid sequences and up to twelve nucleic acid sequences, wherein the at least eight nucleic acid nucleic acid sequences and up to twelve nucleic acid sequences include MTUS1 and at least seven sequences selected from the group of nucleic acids consisting of CDH1, ECM1, EIF1 B, FXR1, HTR2B, ID2, LMCD1, LTA4H, RAB31, ROBO1, and SATB1 and detecting the level of expression of the at least eight nucleic acid sequences and up to twelve nucleic acid sequences nucleic acid sequences in the tumor sample from the subject.

2. The method of claim 1, wherein the array consists of nucleic acid sequences that hybridize specifically to the group of nucleic acids consisting of HTR2B, LMCD1, MTUS1, ROBO1, and SATB1 and at least three sequences selected from the group of nucleic acids consisting of CDH1, ECM1, EIF1 B, FXR1, ID2, LTA4H, and RAB31.

3. The method of claim 1, wherein the tumor sample is from a biopsy sample.

4. The method of claim 1, wherein the tumor sample is from a fine needle biopsy.

5. The method of claim 1, further comprising detecting the level of expression of one or more control genes selected from the group consisting of MRPS21, SAP130, and RBM23.

6. The method of claim 1, wherein the array consists of nucleic acid sequences capable of hybridizing to at least ten nucleic acid sequences, wherein the ten nucleic acid sequences include MTUS1 and at least nine sequences selected from the group of nucleic acids consisting of CDH1, ECM1, EIF1 B, FXR1, HTR2B, ID2, LMCD1, LTA4H, RAB31, ROBO1, and SATB1.

7. The method of claim 1, wherein the array consists of nucleic acid sequences capable of hybridizing to the group of nucleic acids consisting of MTUS1, CDH1, ECM1, EIF1B, FXR1, HTR2B, ID2, LMCD1, LTA4H, RAB31, ROBO1, and SATB1.

\* \* \* \* \*